United States Patent [19]

Broadhurst et al.

[11] Patent Number: 5,045,566

[45] Date of Patent: Sep. 3, 1991

[54] IMIDATE INSECTICIDES

[75] Inventors: Michael D. Broadhurst, Novato; Thomas H. Cromartie, Albany; Karl J. Fisher, Fairfax; William G. Haag, Martinez, all of Calif.

[73] Assignee: ICI Americas Inc., Wilmington, Del.

[21] Appl. No.: 343,552

[22] Filed: Apr. 27, 1989

Related U.S. Application Data

[63] Continuation-in-part of Ser. No. 263,605, Oct. 31, 1988, abandoned, and a continuation-in-part of Ser. No. 264,746, Oct. 31, 1988, abandoned, each is a continuation-in-part of Ser. No. 122,877, Nov. 17, 1987, abandoned.

[51] Int. Cl.$^5$ .............................................. A61K 37/52
[52] U.S. Cl. ................................... 514/508; 514/351; 514/357; 514/466; 558/9; 549/439; 549/366; 549/491; 546/300; 546/290
[58] Field of Search .............. 514/508, 361, 357, 466; 558/9; 549/366, 439, 491; 546/290, 300

[56] References Cited

U.S. PATENT DOCUMENTS

| | | | |
|---|---|---|---|
| 3,832,351 | 8/1974 | Tanaka et al. | 71/107 |
| 3,847,988 | 11/1974 | Gold | 71/105 |
| 3,899,582 | 8/1975 | Tanaka et al. | 71/107 |
| 4,254,264 | 3/1981 | Kohn et al. | 546/291 |
| 4,256,893 | 3/1981 | Malhotra | 546/301 |
| 4,261,920 | 4/1981 | Fuchs et al. | 200/465 |
| 4,272,449 | 6/1981 | Kohn et al. | 200/453.99 |
| 4,285,879 | 8/1981 | Kohn et al. | 200/453.7 |
| 4,288,621 | 9/1981 | Kohn et al. | 564/190 |
| 4,329,518 | 5/1982 | Plummer | 568/807 |
| 4,370,346 | 1/1983 | Punia | 424/305 |
| 4,512,989 | 4/1985 | Ohyama et al. | 71/107 |
| 4,594,355 | 6/1986 | Elliott et al. | 514/521 |
| 4,692,187 | 9/1987 | Kiehs et al. | 71/107 |

FOREIGN PATENT DOCUMENTS

| | | | |
|---|---|---|---|
| 6155 | 1/1980 | European Pat. Off. | 71/107 |
| 196156 | 10/1986 | European Pat. Off. | 71/107 |
| 211561 | 2/1987 | European Pat. Off. | 71/107 |
| 239535 | 9/1987 | European Pat. Off. | 546/301 |
| 271240 | 6/1988 | European Pat. Off. | 71/107 |
| 2944849 | 6/1981 | Fed. Rep. of Germany | 71/107 |
| 23775 | 2/1989 | Iran | 71/107 |
| 4927331 | 7/1974 | Japan | 71/106 |
| 5094133 | 7/1975 | Japan | 71/107 |
| 549342 | 5/1974 | Switzerland | 71/106 |
| 1189238 | 4/1970 | United Kingdom | 71/107 |
| 2122616 | 1/1984 | United Kingdom | 71/107 |

OTHER PUBLICATIONS

Elliott et al., J. Chem. Soc. (C) (1971) pp. 2551–2554.
Elliott et al., J. Sci. Food & Agricultural, vol. 18, pp. 167–171 (1967).
Plummer et al., Pesticide Science, vol. 14, pp. 560–570 (1983).
Tanaka et al., Agricultural & Biological Chemistry, vol. 41, pp. 1953–1959 (1977).
Naumann, Chemie der Pflanzenschutzund Schadlings-bekampfungsmittel, vol. 7, pp. 70–74, 76–77, 82–83 (1981).

Primary Examiner—James H. Reamer
Attorney, Agent, or Firm—Joel G. Ackerman

[57] ABSTRACT

A series of novel imidate insecticides distinguished by the general formula

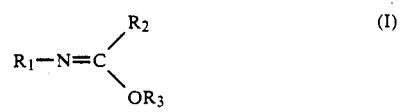

in which $R_1$ is an optionally substituted aryl group in which the substituents are halo, $C_1$-$C_4$ alkyl, $C_1$-$C_4$ haloalkoxy, $C_1$-$C_4$ alkoxy, $C_1$-$C_4$ haloalkylthio, $C_3$-$C_6$ cycloalkyl, nitro, $C_1$-$C_4$ haloalkyl, $C_2$-$C_5$ carboalkoxy, $C_1$-$C_4$ alkylthio, cyano, $C_1$-$C_4$ alkylsulfonyl, $C_2$-$C_4$ haloalkylsulfonyl; $C_2$-$C_5$ alkylcarbonyl, $C_2$-$C_4$ alkyleneoxy, $C_1$-$C_2$ perhaloalkyleneoxy; $C_1$-$C_4$ alkylendioxy, $C_1$-$C_3$ halo-substituted alkylenedioxy, phenyl, mono-substituted phenyl, pyridyloxy, $C_2$-$C_4$ alkylene, $C_2$-$C_4$ alkenyl, $C_3$-haloalkenoxy; and/or amido;

$R_2$ is $C_1$-$C_7$ alkyl, $C_1$-$C_6$ haloalkyl, cyclopropyl, cyclobutyl, mono- or poly- halo- or methyl-substituted cyclopropyl, cyano, $C_2$-$C_4$ alkoxyalkyl, $C_2$-$C_6$ haloalkenyl or $C_2$-$C_6$ alkenyl; and $R_3$ is (a) an optionally substituted 3-phenoxyphenalkyl, 3-phenoxypyridylalkyl, 3-(pyridyloxy)phenalkyl, 3-phenylaminophenalkyl, 3-benzylphenalkyl or benzyloxyphenalkyl moiety; (b) a benzylfuranylmethyl moiety; (c) a 3- or 4-substituted benzyl or tetrafluorobenzyl moiety; (d) 4-phenoxy-2-butyn-2-yl; (e) 2-methyl-3-phenylbenzyl, or (f) 4-(4-trifluoromethyl-2-pyridyloxy)benzyl.

134 Claims, No Drawings

IMIDATE INSECTICIDES

CROSS-REFERENCE TO RELATED APPLICATIONS

This is a continuation-in-part of Application Ser. No. 263,605, filed Oct. 31, 1988, and of Application Ser. No. 264,746, filed Oct. 31, 1988, both of which are continuations-in-part of Application Ser. No. 122,877, filed Nov. 17, 1987 all now abandoned.

This invention relates to a series of novel imidate insecticides distinguished by the general formula $$R_1-N=C\begin{matrix}R_2\\OR_3\end{matrix} \quad (I)$$

in which

R$_1$ is an optionally substituted aryl group in which the substituents are halo, C$_1$-C$_4$ alkyl, C$_1$-C$_4$ haloalkoxy, C$_1$-C$_4$ alkoxy, C$_1$-C$_4$ haloalkylthio, C$_3$-C$_6$ cycloalkyl, nitro, C$_1$-C$_4$ haloalkyl, C$_2$-C$_5$ carboalkoxy, C$_1$-C$_4$ alkylthio, cyano, C$_1$-C$_4$ alkylsulfonyl, C$_1$-C$_4$ haloalkylsulfonyl, C$_2$-C$_5$ alkylcarbonyl, C$_2$-C$_4$ alkyleneoxy, C$_1$-C$_2$ perhaloalkyleneoxy, C$_1$-C$_4$ alkylenedioxy, C$_1$-C$_3$ halo-substituted alkylenedioxy, phenyl, mono-substituted phenyl, pyridyloxy, C$_2$-C$_4$ alkylene, C$_2$-C$_4$ alkenyl, C$_3$-haloalkenoxy, and/or amido;

R$_2$ is C$_1$-C$_7$ alkyl, C$_1$-C$_6$ haloalkyl, cyclopropyl, cyclobutyl, mono- or poly- halo- or methyl-substituted cyclopropyl, cyano, C$_2$-C$_4$ alkoxyalkyl, C$_2$-C$_6$ haloalkenyl or C$_2$-C$_6$ alkenyl; and R$_3$ is (a) an optionally substituted 3-phenoxyphenalkyl, 3-phenoxypyridylalkyl, 3-(pyridyloxy)phenalkyl, 3-phenylaminophenalkyl, 3-benzylphenalkyl or benzyloxyphenalkyl moiety; (b) a benzylfuranylmethyl moiety; (c) a 3- or 4-substituted benzyl or tetrafluorobenzyl moiety; (d) 4-phenoxy-2-butyn-2-yl; (e) 2-methyl-3-phenylbenzyl; or (f) 4-(4-trifluoromethyl-2-pyridyloxy)benzyl.

Compounds of this invention demonstrate activity in controlling various types of insects, including lepidoptera, hemiptera and coleoptera, particularly in foliar application.

Another aspect of this invention involves insecticidal compositions comprising an insecticidally effective amount of a compound of the invention with an insecticidally suitable diluent or carrier.

In another aspect, this invention involves a method for controlling insects by administration of an insecticidally effective amount of a compound or composition of this invention to a locus where control is desired.

The term "insects" as used herein refers to the broad and commonly understood usage rather than to those creatures which in the strict biological sense are classified as insects. In addition to those belonging to the class Insecta, this term includes some classes of acarids such as mites and the like.

More particularly, the compounds of formula (I) are those in which:

R$_1$ is naphthyl, optionally substituted by up to 2 halogens; or phenyl, optionally substituted by one or more of the following: C$_2$-C$_5$ carboalkoxy, C$_1$-C$_4$ alkylsulfonyl, C$_1$-C$_4$ haloalkylsulfonyl, C$_2$-C$_5$ alkylcarbonyl, C$_2$-C$_4$ alkenyl, C$_3$-haloalkenoxy, C$_1$-C$_4$ haloalkylthio, C$_3$-C$_6$ cycloalkyl, phenyl, monosubstituted phenyl, pyridyloxy, C$_2$-C$_4$ alkyleneoxy, C$_1$-C$_2$ perhaloalkyleneoxy, C$_1$-C$_4$ alkylenedioxy, C$_1$-C$_3$ haloalkylenedioxy, C$_2$-C$_4$ alkylene, amido, nitro, cyano, up to two C$_1$-C$_4$ alkylthio groups, up to three C$_1$-C$_4$ alkoxy groups, up to three C$_1$-C$_4$ haloalkoxy groups, up to three C$_1$-C$_4$ alkyl groups, up to three C$_1$-C$_4$ haloalkyl groups, or up to five halogens;

R$_2$ is methyl; ethyl; n-propyl; C$_3$-C$_7$ branched alkyl; C$_1$-C$_6$ haloalkyl, cyclopropyl optionally substituted by up to 4 methyl groups or up to 2 halogens, cyclobutyl, cyano, C$_2$-C$_4$ alkoxyalkyl, C$_2$-C$_6$ alkenyl or C$_2$-C$_6$ haloalkenyl; and R$_3$ is (a)

$$-\overset{R_6}{\underset{}{CH}}-(CH_2)_m\underset{B\overset{}{\underset{R_4}{\diagdown}}C}{\overset{A}{\diagup}}R_7$$

in which m is 0 or 1;

A, B and C are each carbon or nitrogen, provided that A, B and C are not all nitrogen and if two of A, B and C are nitrogen, then A and C are nitrogen;

R$_4$ is hydrogen, monohalo or dihalo;

R$_6$ is hydrogen, methyl, fluoro or ethynyl; and

R$_7$ is (i)

$$-O\underset{R_5}{\diagup}\overset{D}{\underset{}{\diagdown}}E$$

in which D and E are each carbon or nitrogen provided that both D and E are not nitrogen, and further provided that if any of A, B or C is nitrogen, then D and E are both carbon; and R$_5$ is hydrogen, C$_1$-C$_4$ alkyl, C$_1$-C$_4$ alkoxy, trifluoromethyl, cyano, C$_1$-C$_4$ alkylthio, C$_1$-C$_4$ alkylsulfonyl, or mono- or polyhalo;

(ii)

$$-NH-\phantom{X}-R_8;$$

$$-CH_2-\phantom{X}-R_8;$$

$$-OCH_2-\phantom{X}-R_8;$$

in which R$_8$ is hydrogen or halogen; or (iii) —O—CH$_2$—CH=CH$_2$;

(b)

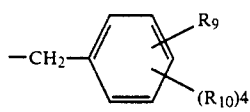

in which
(i) $R_9$ is 4-fluoro, 4-methoxymethyl, or 4-propargyl, and $R_{10}$ is fluoro or
(ii) $R_9$ is 3- or 4-allyl, 3- or 4-propargyl, or 3- or 4-(mono- or dihalo)allyl, and $R_{10}$ is hydrogen or fluoro;

(c)

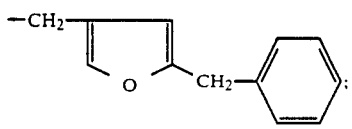

(d) 4-phenoxy-2-butyn-2-yl;
(e) 3-bromo-4-fluorobenzyl;
(f) 4-(benzyloxy)benzyl;
(g) 4-(4-fluorobenzyloxy)benzyl;
(h) 4-(4-trifluromethyl-2-pyridyloxy)benzyl; or
(j)

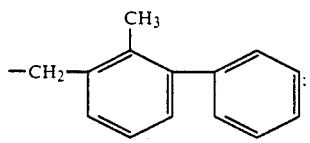

provided that:
(i) $R_1$ is not 2,3-dichlorophenyl, 2,6-difluorophenyl, 2,6-di(C1-C4 alkyl)phenyl, 2,4,6-tribromophenyl or 2,4,6-tri($C_1$-$C_4$ alkoxy)phenyl;
(ii) when $R_2$ is tertiary butyl, $R_1$ is not phenyl, 3-methyl-phenyl, 4-(n-butyl)phenyl or 4-(t-butyl)phenyl; and
(iii) when $R_2$ is a $C_5$ alkyl group, then $R_1$ is not 4-isopropylphenyl.

A more preferred class of compounds are those in which $R_1$ does not contain substituents at both ortho positions on the phenyl ring, i.e., in which $R_1$ does not contain a 2,6-disubstitution, 2,3,6-trisubstitution, or a 2,4,6-trisubstitution on the phenyl ring.

An even more preferred class is that in which the phenyl ring of $R_1$ is substituted at the 3-, 4-, and/or 5-positions, including mono-, di- and tri-substituted phenyl compounds, as well as phenyl compounds having a 3,4-alkylene, alkeneoxy, perhaloalkyeneoxy, alkylenedioxy, or haloalkylenedioxy substitution. Such compounds more particularly have the formula

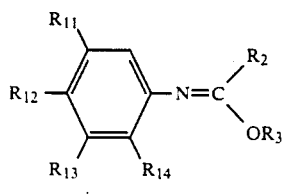

in which $R_2$ and $R_3$ are as defined above; $R_{11}$ is hydrogen, halogen, $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, $C_1$-$C_4$ haloalkylthio, $C_2$-$C_5$ carboalkoxy, $C_2$-$C_5$ alkylcarbonyl, nitro or cyano; $R_{12}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_3$-haloalkenoxy, nitro, cyano, $C_2$-$C_5$ alkylcarbonyl, $C_1$-$C_4$ alkylsulfonyl or $C_2$-$C_5$ carboalkoxy; and $R_{13}$ is hydrogen, halogen, $C_1$-$C_4$ haloalkyl or $C_1$-$C_4$ alkoxy, or $R_{11}$ and $R_{12}$ taken together are $C_2$-$C_4$ alkylene, $C_2$-$C_4$ alkyleneoxy, $C_1$-$C_2$ perhaloalkenenoxy, $C_1$-$C_4$ alkylenedioxy or halo-$C_1$-$C_3$ alkylenedioxy; and $R^{14}$ is hydrogen or fluoro; provided that $R_{11}$, $R_{12}$ and $R_{13}$ are not all hydrogens.

One especially preferred subclass of such compounds are those in which $R_{11}$ is as defined above, and most preferably is halogen, $C_1$-$C_4$ alkyl, $C_1$-$C_4$ haloalkyl, $C_1$-$C_4$ alkoxy or $C_1$-$C_4$ haloalkoxy; $R_{12}$ is a $C_1$-$C_2$ polyhaloalkoxy group containing at least one fluorine atom; and $R_{13}$ is hydrogen or halogen. Examples of such polyhaloalkoxy groups are difluoromethoxy, trifluoromethoxy, difluorochloromethoxy, difluorobromomethoxy, and 1,1,2,2-tetrafluoroethoxy. In one such type of compound, $R_{11}$ is chloro, $R_{12}$ is trifluoromethoxy and $R_{13}$ is hydrogen.

Still another preferred class of compounds is that in which $R_1$ is 3- or 4-trifluoromethylphenyl and $R_3$ is 2,3,5,6-tetrafluoro-4-propargylbenzyl.

Also of interest are compounds having a 2,5-, 2,3,4- or 2,4,5-substitution pattern.

As used herein, these terms have the following meanings:

"Alkyleneoxy" and "alkylenedioxy" refer to linking groups having 1 or 2 oxygen atoms, respectively, and at least one carbon atom (optionally substituted) in a chain. The alkyleneoxy moieties have 1-4, preferably 2-4, carbon atoms in this chain and include, for instance, ethyleneoxy (—O—$C_2H_4$—), dihalomethyleneoxy, dihaloethyleneoxy, and the like. Alkylenedioxy moieties include methylenedioxy (—O—$CH_2$—O—), 1,2-ethylenedioxy (—O—$C_2H_4$—O—), mono- or di-halomethylenedioxy (a methylenedioxy group in which one or both hydrogens are replaced by a halogen) and isopropylenedioxy (—O—$C(CH_3)_2$—O—).

The term "carboalkoxy" refers to a group having the formula

in which $R_{15}$ is an alkyl group. The carbon atom content of the carboalkoxy group is meant to include the carbon atom of the carbonyl moiety in that group. Thus, $C_2$-carboalkoxy refers to carbomethoxy, etc. Similarly, the carbon atom content of an alkylcarbonyl group includes the carbon atom in the carbonyl moiety. The simplest member of this group is thus acetyl, $CH_3C(O)$—.

When $R_1$ represents a phenyl ring substituted by a second phenyl ring, the second phenyl ring may be unsubstituted or mono-substituted in which the substituent is halogen, $C_1$-$C_4$ alkyl, $C_1$-$C_4$ haloalkyl, nitro, cyano, $C_1$-$C_4$ alkylsulfonyl, $C_1$-$C_4$ haloalkylsulfonyl, or $C_1$-$C_4$ alkylenedioxy (optionally further substituted by up to 2 halogens).

. Terms defining halogenated groups such as "haloalkyl", "haloalkoxy", "haloalkenyl", "haloalkenoxy" and the like include mono- and polyhalogenated groups of the indicated number of carbon atoms. In polyhalogenated groups the halogens may be the same or different.

"Propargyl" refers to the 2-propynyl group —CH$_2$—C≡CH and "allyl" refers to the 2-propenyl group —CH$_2$—CH=CH$_2$.

Cyclopropyl groups for R$_2$ may be substituted by up to 4 methyl groups or alternatively up to 2 halogen atoms.

For the various subgroups falling within the general definition of R$_3$, preferred types are:

For R$_4$: hydrogen and 2-, 4- or 6-monohalo, particularly monochloro or monofluoro;

For R$_5$: 2-, 3- or 4-halo, 2,4-, 3,4- or 3,5-dihalo, particularly difluoro, pentahalo, particularly pentafluoro, 4-methyl, 4-trifluoromethyl, 4-methoxy, 4-methylthio and 4-methylsulfonyl.

The following are examples of specific embodiments of groups falling within the definition of R$_3$. For convenience in specifying positions of substitution of compounds of the type

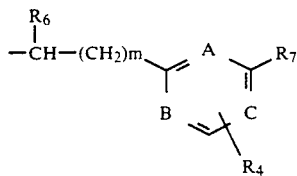

the position of attachment of the group

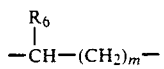

was given the number 1 and the position of attachment of group R$_7$, the number 3. When A, B or C was a nitrogen atom, the compounds were designated pyrid-2-yl, pyrid-6-yl or pyrid-4-yl, respectively.

3-phenoxybenzyl,
3-phenoxy-(alpha-methyl)benzyl,
3-phenoxyphenethyl,
3-(4-pyridyloxy)benzyl,
3-(4-fluorophenoxy)benzyl,
3-(4-chlorophenoxy)benzyl,
3-(4-bromophenoxy)benzyl,
3-(4-iodophenoxy)benzyl,
3-(2,4-difluorophenoxy)benzyl,
3-(3,4-difluorophenoxy)benzyl,
3-(3,5-difluorophenoxy)benzyl,
3-(2,3,4,5,6-pentafluorophenoxy)benzyl,
3-(4-fluorophenoxy)-4-fluorobenzyl,
3-(4-fluorophenoxy)-4-chlorobenzyl,
3-(4-chlorophenoxy)-4-fluorobenzyl,
3-phenoxy-4-fluorobenzyl,
3-(4-fluorophenoxy)-6-chlorobenzyl,
3-(4-fluorophenoxy)-5-fluorobenzyl,
3-(4-fluorophenoxy)-4,6-difluorobenzyl,
3-(4-fluorophenoxy)-6-fluorobenzyl,
3-(4-fluorophenoxy)-2-fluorobenzyl,
3-(4-cyanophenoxy)benzyl,
3-(4-methylphenoxy)benzyl,
3-(4-methoxyphenoxy)benzyl,
3-(3,4-difluorophenoxy)-4-fluorobenzyl,
3-(3-fluorophenoxy)benzyl,
3-(2-fluorophenoxy)benzyl,
3-(3-chlorophenoxy)benzyl,
3-(4-trifluoromethylphenoxy)benzyl,
3-(4-methylthiophenoxy)benzyl,
3-(4-fluorophenoxy)-(alpha-fluoro)benzyl,
3-phenoxy-pyrid-2-yl-methyl,
3-phenoxy-pyrid-4-yl-methyl,
3-phenoxy-pyrid-6-yl-methyl,
3-(4-fluorophenoxy)pyrid-2-ylmethyl,
3-(4-chlorophenoxy)pyrid-2-ylmethyl,
3-(4-fluorophenoxy)pyrid-4-ylmethyl,
3-(4-chlorophenoxy)pyrid-2-ylmethyl,
3-(4-chlorophenoxy)pyrid-4-ylmethyl,
3-(4-chlorophenoxy)pyrid-6-ylmethyl,
3-(3,4-difluorophenoxy)pyrid-2-ylmethyl,
3-(4-methylphenoxy)pyrid-2-ylmethyl,
3-(4-fluorophenoxy)pyrid-6-ylmethyl,
3-(pyrid-2-yloxy)benzyl,
3-(4-chloropyrid-2-yloxy)benzyl,
2,3,4,5,6-tetrafluorobenzyl,
4-methoxymethyl-2,3,5,6-tetrafluorobenzyl,
4-propargyl-2,3,5,6-tetrafluorobenzyl,
3-allyloxybenzyl,
3-(benzyl)benzyl,
3-(benzyloxy)benzyl,
3-(4-fluorobenzyloxy)benzyl,
3-(phenylamino)benzyl,
3-(4-fluorophenylamino)benzyl,
1-(3-phenoxyphenyl)prop-2-ynyl,
3-bromo-4-fluorobenzyl,
4-phenoxy-2-butyn-2-yl,
4-(benzyloxy)benzyl,
4-(4-fluorobenzyloxy)benzyl,
4-(4-trifluoromethyl-2-pyridyloxy)benzyl
2-methyl-3-phenylbenzyl,
5-benzyl-3-furanylmethyl.

PROCESSES FOR PREPARATION OF COMPOUNDS OF THIS INVENTION

Process (A)

Compounds of this invention in general are prepared by reaction of an imidoyl halide (preferably chloride) with an alkali metal alkoxide according to the general reaction:

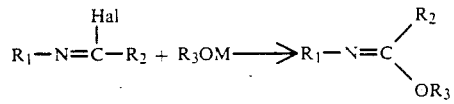

in which M is an alkali metal, preferably sodium or potassium and Hal is a halogen, particularly chloro or bromo.

This reaction is conducted at a temperature of from about −70° C. to about +65° C., most preferably at about room temperature, for a time which may range from about 5 minutes to about 24 hours. The reaction is conducted in the presence of a solvent, for example, an aromatic hydrocarbon such as benzene, toluene, or xylene or an ether, such as diethyl ether, diisopropyl ether, diisoamyl ether, dibutyl ether, furan, 1,2-dimethoxyethane, or tetrahydrofuran (preferably tetrahydrofuran). In some instances, apparent to those skilled in the art, it is advantageous to add the solution of the alkali metal alkoxide to a solution of the imidoyl halide or to use substantial excesses of alkoxide. The resulting product may be recovered by conventional techniques.

The alkoxide R$_3$OM is produced by reaction of an appropriate alcohol, such as 3-phenoxybenzyl alcohol, with an alkali metal-containing base, for instance, an alkali metal hydride (e.g., potassium or preferably sodium hydride) in the presence of a solvent such as that used in reaction of the alkali metal alkoxide with the imidoyl halide. In general, this reaction is conducted at reflux temperature under an inert atmosphere for a time which may range up to about 2 hours.

The alcohols, if not commercially available, can be prepared according to known methods such as those described in the following references: U.S. Pat. Nos. 4,256,893; 4,261,920; and 4,329,518, and Volume 7 of the text "Chemie der Pflanzenschutz und Schadlingsbekampfungsmittel" (phenoxybenzyl, phenoxypyridylmethyl and pyridyloxy type alcohols); Elliott et al, *J. Chem Soc.* (C), 1971, pp. 2551–1554 (5-benzyl-2-furanylmethanol); *Pesticide Science* 14, 560–570 (1983) (2-methyl-3-phenylbenzyl alcohol); U.S. Pat. Nos. 4,370,346 and 4,594,355; British patent 2,122,616; European patent applications 196,156 and 271,240; and *J. Sci. Food & Agriculture* 18, 167 (1967) for various substituted benzyl alcohols; European patent application 211,561 for 3-phenylaminobenzyl alcohols; Swiss patent 549,342 for 4-phenoxy-2-butyn-1-ol; and Japanese patent 49-27331 for 1-(3-phenoxyphenyl)-2-propyn-1-ol.

The imidoyl halide may be prepared from a starting amine having the formula $R_1NH_2$ or amide having the formula

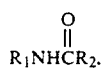

depending on availability. The amines are either generally available or may be prepared by procedures known in the art, for example, those described in "Compendium of Organic Synthetic Methods", Harrison et al. (Wiley-Interscience, New York, 1971).

The amides, if not available, may be produced by reaction of the amine with an appropriate acid chloride having the formula

The temperature of this reaction ranges from about $-40°$ C. to about $+80°$ C. Suitable solvents include hydrocarbon solvents such as toluene and chlorinated hydrocarbon solvents such as methylene chloride, chloroform, carbon tetrachloride, ethylene dichloride, tetrachloroethane and the like, preferably methylene chloride. This reaction is conducted in the presence of a base, preferably a tertiary amine. Suitable bases include triethylamine, quinoline, dimethylaniline, diethylaniline, and pyridine. Triethylamine is the preferred base. The resulting amide is recovered and purified by conventional means.

The imidoyl halide may be prepared from the amide by reacting it with a halogenating agent such as phosphorus pentachloride or phosgene in an organic solvent such as that utilized in the amide production (preferably methylene chloride) or alternatively using phosphorus oxychloride as the solvent. The reaction is carried out under an inert atmosphere for a time which may be up to 24 hours, preferably from 1 to 24 hours, at a temperature of from about 0° C. to about 110° C. Before the imidoyl chloride-containing product is passed to the final step, all substances, such as phosphorus oxychloride or hydrogen chloride, which can react with the alkoxide in the final step, should be removed. This can generally be accomplished by evaporation or distillation.

Alternatively, the compounds of this invention may be prepared by a two-step process indicated as follows:

Process (B)

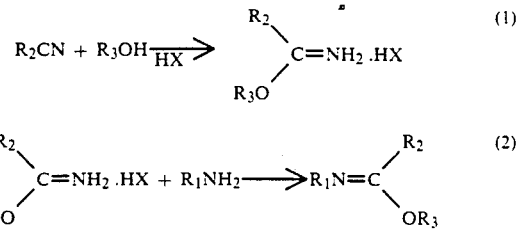

in which "HX" represents a mineral acid.

In the first step, the appropriate alcohol (for instance a phenoxybenzyl alcohol) is mixed with a nitrile having the formula $R_2CN$ at a temperature of from about $-20°$ C. to about $+40°$ C. Then, a solution of a mineral acid such as hydrochloric, hydrobromic, sulfuric or phosphoric acid (preferably hydrochloric acid) dissolved in a suitable organic solvent is added at temperatures from about $-5°$ to about 40° C., preferably 0° C., then stirred at room temperature, to produce the corresponding imidate salt. Suitable solvents for this reaction include aromatic hydrocarbons such as benzene, toluene, or xylene and ethers such as diethyl ether, diisopropyl ether, diamyl ether, furan, tetrahydrofuran and dioxane (preferably dioxane). Time for the reaction may be up to 52 hours. The imidate salts are novel and constitute an aspect of this invention.

In the second step, the imidate salt is suspended in an organic solvent such as that utilized in the previous step, preferably benzene, and reacted with an amine having the formula $R_1NH_2$. The mixture is reacted, optionally with stirring, at a temperature of between about $-50°$ and $+80°$ C., most preferably at room temperature, for a period of time necessary to conduct the reaction, which may be up to 120 hours. The final imidate product may be recovered as in process (A).

Process (C)

A third process may be used for producing many of the compounds of this invention, with the exception of those in which $R_2$ is a group having no alpha-hydrogen, such as cyano, tertiary butyl, vinyl or halovinyl. This process proceeds by way of an intermediate ketenimine, which may be prepared from the amide or from the imidoyl halide. In the first case, the amide (prepared for instance, as described in process A) is reacted with an inexpensive base and a trivalent phosphorus compound, preferably triphenylphosphine. The base is preferably a tertiary amine such as triethylamine. The reaction is carried out at a temperature of from about $-10°$ C. to 40° C. in the presence of a halogen, preferably chlorine or bromine, and an aromatic or chlorinated hydrocarbon solvent such as benzene, toluene, xylene, methylene chloride, ethylene dichloride, chloroform, carbon tetrachloride, tetrachloroethane and the like, preferably methylene chloride. The reaction may then be conducted under reflux temperature of the solvent and the ketenimine recovered according to methods known in the art.

Alternatively, the ketenimine may be prepared by reaction of the imidoyl halide with a base, as just described, but no halogen or trivalent phosphorus compound present.

In the second step of this process, the ketenimine is reacted with an alcohol having the formula R₃OH in the presence of a solvent, preferably an ether solvent, such as diethyl ether, dipropyl ether, diisopropyl ether, dibutyl ether, tetrahydrofuran or 1,2-dimethoxyethane and an alkali metal base such as potassium or sodium hydride, preferably sodium hydride. This reaction is conducted under reflux for a time as necessary which may be up to 48 hours, preferably from about 2 to about 10 hours, at the end of which the reaction mixture is cooled and the imidate product recovered as described above.

This process can be depicted by the general scheme:

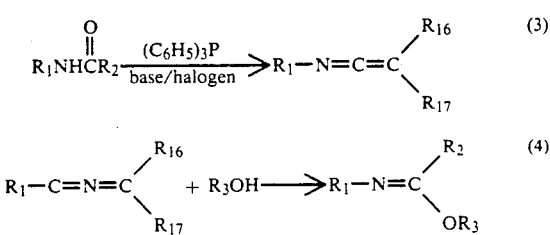

in which $R_1$, $R_2$ and $R_3$ are as previously described and $R_{16}$ and $R_{17}$ are independently hydrogen, $C_1$-$C_6$ alkyl, halo, $C_1$-$C_5$ haloalkyl, $C_1$-$C_3$ alkoxy, $C_2$-$C_5$ alkenyl or $C_2$-$C_5$ haloalkenyl, or $R_{17}$ and $R_{18}$ taken together are a $C_2$-$C_3$ alkylene chain optionally substituted by up to 4 methyl groups or up to 2 halogens.

Ketenimines

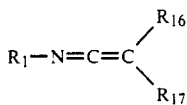

are novel.

Process (D)

This process may be used as an alternative to process (A) for preparation of compounds of this invention from alcohols (R₃OH) which are sensitive to, and could be adversely affected (e.g. decomposed) by, strong bases such as the alkali metal-containing bases (e.g. alkali metal hydrides) used to prepare the alkoxides (R₃OM). Alcohols which may be sensitive to such strong bases include phenoxypyridyl alkanols, alpha-ethynyl alcohols (R₆ is ethynyl) such as 1-(3-phenoxyphenyl)-2-propyn-1-ol and tetrafluoropropargylbenzyl alcohol.

Compounds of this type may be made by direct reaction of the alcohol with the imidoyl chloride in the presence of a tertiary amine base and a reaction-promoting amount of a 4-di(lower alkyl)aminopyridine, preferably 4-dimethylaminopyridine.

Tertiary amines which may be used in this process include trialkylamines such as trimethyl-, triethyl-, tri-n-butylamine and the like, including tertiary amines having mixed alkyl groups, N,N-dialkylanilines such as N,N-dimethylaniline, pyridine and various substituted pyridines.

Preferred tertiary amines, primarily for economic reasons, are triethylamine, N,N-dimethylaniline, and pyridine. The tertiary amine may even be an additional amount of the promoter 4-di(lower alkyl)aminopyridine, over and above that amount needed for promoting the reaction.

The tertiary amine is preferably used in a stoichiometric amount with respect to the alcohol, but may be used in excess of that amount. The promoter 4-di(lower alkyl)aminopyridine may be used in an amount from about 0.05 to about 1 equivalent per equivalent of alcohol, preferably from about 0.05 to about 0.15 equivalent per equivalent, most preferably about 0.1.

This process is preferably conducted at temperatures of from about 10° C. to about 50° C. Lower temperatures may be used, but the reaction rate would be much slower. The process is carried out in the presence of an inert solvent such as an aromatic hydrocarbon (for instance, benzene, toluene or xylene), a chlorinated solvent (such as methylene chloride, ethylene dichloride or chlorobenzene) or an ether (such as diethyl ether, dioxane or tetrahydrofuran).

While this process is particularly suitable for producing compounds from base-sensitive alcohols, it may be used to produce compounds of this invention in general from other alcohols as described.

Alpha-fluorophenoxybenzyl compounds are made from the alpha-fluorobenzyl halide (preferably bromide) rather than the alcohol by reaction with an amide, $R_1NHCOR_2$, in the presence of a halide ion binding agent such as silver oxide or a silver salt, and an inert solvent. Reaction temperatures are from about −20° C. to about 100° C.

The following are representative examples of the preparation of compounds of this invention according to the processes described above.

EXAMPLE 1

Preparation of N-(3-Chloro-4-fluorophenyl)-O-(3-phenoxybenzyl)isobutyrylimidate (Compound 88 herein) (Process A)

(a) Preparation of the Anilide

To a stirred solution of 3-chloro-4-fluoroaniline (10.0 g, 0.069 mol) and triethylamine (11.2 ml, 0.08 mol) in 100 ml methylene chloride was added isobutyryl chloride (7.8 ml, 0.075 mol) dropwise, with cooling, in an ice bath. After the addition, the reaction mixture was permitted to reach room temperature at which point 100 ml of water was added. The aqueous and organic layers were separated; the organic layer was dried over anhydrous sodium sulfate and the solvent evaporated to provide 15.2 g (103% of theoretical yield) of a tan solid, spectroscopically identified as 3-chloro-4-fluoroisobutyrylanilide, m.p. 114°-117° C.

(b) Preparation of the Imidoyl Chloride

To a solution of the anilide prepared in step (a) (2.1 g, 9.3 mmol) in 50 ml methylene chloride under an argon atmosphere there was added phosphorus pentachloride (1.93 g, 9.3 mmol). After two hours, the solvent was evaporated at 20 mmHg and the resulting brown oil was further evaporated at 40° C. and less than 1 mmHg. The product, N-(1-chloro-2-methylpropylidene)-3-chloro-4-fluoroaniline, was transferred to the next step without further purification.

(c) Preparation of the Sodium Alkoxide

A suspension of sodium hydride (0.26 g, 11 mmol) in tetrahydrofuran (40 ml) was prepared and stirred under an argon atmosphere. To this suspension there was added 3-phenoxybenzyl alcohol (1.75 ml, 10 mmol). The resulting mixture was heated to reflux 0.5 hour and then cooled. There was obtained a pale yellow solution of sodium 3-phenoxybenzylalkoxide which contained a small amount of gray solid.

(d) Preparation of the Imidate

To the alkoxide solution produced in step (c) there was added the imidoyl chloride prepared in step (b), dissolved in about 10 ml tetrahydrofuran, at room temperature with cooling over several minutes. At the end of one hour, the product mixture was poured into about 200 ml hexanes and filtered through a pad of silica gel. The solvent was evaporated to produce 3.0 g (82% of theoretical yield) of a tan oil, which was further purified by chromatography over silica gel. Evaporation of the solvent from the product fraction gave 2.4 g (65% of theoretical yield) of a nearly colorless, viscous oil, identified spectroscopically as the desired product.

EXAMPLE 2

(Process B)

This example illustrates the preparation of the compound of Example 1 by the second described process, through the intermediate imidate salt.

(a) A solution of 3-phenoxybenzyl alcohol (10 ml, 57.4 mmol) and isobutyronitrile (5.2 ml, 57.88 mmol) was cooled to 0° C. There was then added 12.5 ml of a 4.1 molar solution of anhydrous HCl (62.5 mmol) in dioxane, dropwise, followed by stirring at 25° C. for 16 hours. The product, O-(3-phenoxybenzyl)isobutyrylimidate hydrochloride, separated out as a white solid.

(b) The imidate hydrochloride salt obtained above (0.99 g, 3.2 mmol) was suspended in 15 ml benzene and 0.60 g (4.1 mmol) 3-chloro-4-fluoroaniline was added. The mixture was then stirred at 25° C. for 72 hours and filtered through silica gel. The combined filtrates were concentrated at reduced pressure and purified on silica gel using 5% ethylacetate in hexanes as eluent. There was obtained 0.78 g of the desired product of 77% purity.

EXAMPLE 3

Preparation of N-(3,4-Difluorophenyl)-O-(4'-fluoro-3-phenoxybenzyl)isobutyrylimidate (Compound 66 herein) (Process C)

This example illustrates production of a compound of this invention according to the third process, through an intermediate ketenimine.

(a) A mixture was prepared which contained 3,4-difluoroisobutyrylanilide (4.0 g, 20.1 mmol, prepared analogously to Example 1, step (a)), triethylamine (6 ml, 43 mmol) and triphenylphosphine (5.3 g, 20.2 mmol) and 50 ml methylene chloride. The mixture was cooled to 0° C.; then bromine (1.0 ml, 20 mmol) was added dropwise. The mixture was then refluxed for 2 hours, cooled to room temperature and concentrated at reduced pressure. The residue was extracted with 50 ml hexanes; the extract was filtered and concentrated at reduced pressure to yield 3.84 g of the crude ketenimine.

(b) The ketenimine thus prepared was combined with 3-(4-fluorophenoxy)benzyl alcohol (obtained, for instance, by the method of Fuchs et al., U.S. Pat. No. 4,242,357) (0.80 g, 3.7 mmol) and the resulting mixture dissolved in 50 ml 1,2-dimethoxyethane. Sodium hydride (0.10 g, 4.2 mmol) was added and the mixture heated at reflux for 2 hours. The resulting mixture was allowed to cool, filtered, and concentrated. The crude product was purified by chromatography on silica gel using 5% ethyl acetate in hexanes as eluent. There was obtained 1.05 g (72% of theoretical yield) of the desired product.

EXAMPLE 4

Preparation of N-(4-Chlorophenyl)-O-(3-phenoxybenzyl)cyclopropylcarboximidate (Compound 35 herein) (Process A)

N-(4-chlorophenyl)cyclopropane carboxamide (4.0 g, 20.4 mmol), prepared from 4-chloroaniline and cyclopropane carboxylic acid chloride analogously to Example 1, step (a)) was dissolved in 50 ml methylene chloride and treated with $PCl_5$ (4.25 g, 20.4 mmol) all at once, under an argon atmosphere. After 20 minutes, n-pentane was added and the solid was filtered. The solvents were evaporated at 50° C. yielding a residual light brown oil, the desired imidoyl chloride. This was taken up in a small amount of dry tetrahydrofuran.

The imidoyl chloride thus prepared was then added to a solution of sodium 3-phenoxybenzyl alkoxide prepared using 4.1 g of 3-phenoxybenzyl alcohol and 0.5 g of sodium hydride as in Example 1, step (c). The mixture was let stand for 4 hours at room temperature then briefly heated to reflux and cooled. Water and hexanes were added and the aqueous and organic phases separated. The organic layer was washed with water, dried over magnesium sulfate and evaporated. The residue was redissolved in hexanes and filtered through silica gel. Evaporation gave a colorless oil, identified spectroscopically as the desired product.

EXAMPLE 5

Preparation of N-(3-Trifluoromethylphenyl)-O-(3-phenoxybenzyl)dichloroacetimidate (Compound 72 herein) (Process A)

In a flask were combined 4.2 g (20.2 mol) phosphorus pentachloride, 3-trifluoromethyldichloroacetanilide [5.4 g, 19.8 mole, prepared analogously to Example 1, step (a)] and phosphorus oxychloride (solvent) under argon. The mixture was heated to 60° C. for several hours; then hexanes were added and the resulting solution filtered. The filtrate was evaporated and the product imidoyl chloride, an oil, was taken up in a small amount of dry tetrahydrofuran.

The imidoyl chloride thus prepared was added to a solution of sodium 3-phenoxybenzyl alkoxide (prepared analogously to Example 1 step (c) from 4.0 g 3-phenoxybenzyl alcohol and 0.5 g sodium hydride).

The resulting mixture was stirred overnight at ambient temperature; then water and hexanes were added, the mixture was phase separated, washed with 5% HCl and saturated sodium bicarbonate solution, dried over magnesium sulfate and evaporated to produce an oil. This oil was then purified by chromatography over silica gel to give a pale yellow oil, identified spectroscopically as the desired product.

EXAMPLE 6

Preparation of N-(3,4-Methylenedioxyphenyl)-O-(3-phenoxybenzyl)-propionimidate (Compound 189 herein) (Process A)

This compound was prepared analogously to Example 1 from 2.0 g (10.4 mmol) 3,4-methylenedioxypropionanilide (itself prepared from 3,4-methylenedioxyaniline and propionyl chloride), 2.26 g 3-phenoxybenzyl alcohol and 0.29 g sodium hydride. There was obtained 1.9 g (50% of theoretical yield) of a colorless viscous oil, identified spectroscopically as the desired product.

EXAMPLE 7

Preparation of
N-(3-chloro-4-fluorophenyl)-O-[1-(3-phenoxyphenyl)-2-propyn-1-yl]isobutyrimidate (Compound 533 herein) (Process D)

(a) Preparation of the alcohol

A solution was prepared containing 2.4 g (24 mmol) trimethylsilylacetylene in 50 ml tetrahydrofuran. The temperature was kept at −78° C. with stirring. Then 10.0 ml of a 2.5M solution of n-butyllithium in hexanes was slowly added. After further stirring for 15 minutes, 3.5 ml (4.0 g, 20 mmol) 3-phenoxybenzaldehyde was added. The solution was stirred at −78° C. for 10 minutes and was allowed to warm to room temperature over 30 minutes.

The reaction was quenched with 5% sodium bicarbonate. The tetrahydrofuran was removed in vacuo, the aqueous phase was extracted with methylene chloride and the organic layers combined and dried to produce a light oil.

A solution of the light oil in methanol was stirred with potassium carbonate, then concentrated, dissolved in water and extracted with ether. The desired alcohol, 1-(3-phenoxyphenyl)-2-propyn-1-ol (4.3 g, 96% of theoretical yield), a light yellow oil, was obtained from the ether extracts.

(b) Preparation of the imidate

To a solution of 0.7 g (3.0 mmol) of N-3-chloro-4-fluorophenyl isobutyrimidoyl chloride [prepared as in Example 1 (a)-(b)] was added triethylamine (0.63 ml, 0.45 g, 4.5 mmol), 1-(3-phenoxyphenyl)-2-propyn-1-ol (prepared as above) (1.0 g, 4.5 mmol) and 4-dimethylaminopyridine (50 mg, 0.4 mmol). The mixture was stirred for 24 hours at room temperature, concentrated and diluted with 100 ml hexanes. The resulting slurry was filtered through alumina and concentrated to give 0.90 g (70% of theoretical yield) of the desired compound.

Tables 1 and 2 depict representative compounds of this invention, prepared according to a method as described above. Table 1 contains compounds in which $R_3$ is a substituted or unsubstituted 3-phenoxybenzyl moiety. Table 2 contains compounds in which $R_3$ represents other moieties. Nearly all compounds were produced as oils; all structures were confirmed by spectroscopic analysis.

For convenience, since nearly all compounds in the tables are of the type in which $R_1$ is a substituted or unsubstituted phenyl ring, the tables only depict the substituents (if any) on that ring, with H = unsubstituted phenyl, 3-Cl = 3-chlorophenyl, 3-Cl,4F = 3-chloro-4-fluorophenyl, and the like. Naphthyl compounds are indicated as such.

TABLE 1

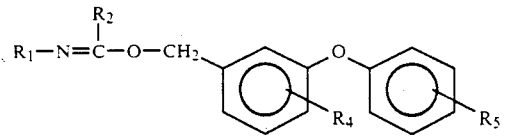

($R_1$ = unsubstituted or substituted phenyl)

| Cmpd. No. | Phenyl Subst. | $R_2$ | $R_4$ | $R_5$ |
|---|---|---|---|---|
| 1 | 3-Cl | CHCl$_2$ | H | H |
| 2 | 4-Cl | i-C$_3$H$_7$ | H | H |
| 3 | 4-Cl | —CCl$_2$CH$_3$ | H | H |
| 4 | 2,4-Cl | CHCl$_2$ | H | H |
| 5 | 4-Cl | CH$_3$-cyclopropyl | H | H |
| 6 | 4-Cl | CH$_3$—C=CH$_2$ | H | H |
| 7 | 3-Cl | i-C$_3$H$_7$ | H | H |
| 8 | 4-Cl | cyclobutyl | H | H |
| 9 | 3,4-Cl | i-C$_3$H$_7$ | H | H |
| 10 | 3,5-Cl | i-C$_4$H$_9$ | H | H |
| 11 | 4-Cl | C$_2$H$_5$ | H | H |
| 12 | 3-Cl | t-C$_4$H$_9$ | H | H |
| 13 | 2,5-Cl | i-C$_3$H$_7$ | H | H |
| 14 | 3,4-Cl | i-C$_3$H$_7$ | H | H |
| 15 | 4-Cl | cyclopropyl-CH$_3$ | H | H |
| 16 | 3,5-Cl | i-C$_3$H$_7$ | H | H |

TABLE 1-continued

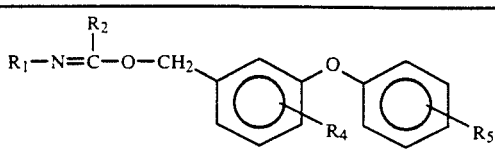

($R_1$ = unsubstituted or substituted phenyl)

| Cmpd. No. | Phenyl Subst. | $R_2$ | $R_4$ | $R_5$ |
|---|---|---|---|---|
| 17 | 2-Cl | i-$C_3H_7$ | H | H |
| 18 | 2,4,5-Cl | i-$C_3H_7$ | H | H |
| 19 | 2,4,6-Cl | i-$C_3H_7$ | H | H |
| 20 | 3,4,5-Cl | i-$C_3H_7$ | H | H |
| 21 | 4-Cl | —CN | H | H |
| 22 | 4-Cl | —CH($CH_3$)$OCH_3$ | H | H |
| 23 | 4-Cl | i-$C_3H_7$ | 4-F | H |
| 24 | 3-Cl | ◁ | H | H |
| 25 | 3,4-Cl | t-$C_4H_9$ | H | H |
| 26 | 4-Cl | sec-$C_4H_9$ | H | H |
| 27 | 3,4-Cl | —CHCl$CH_3$ | H | H |
| 28 | 2,3-Cl | $C_2H_5$ | H | H |
| 29 | 4-Cl | $CHCl_2$ | H | H |
| 30 | 4-Cl | t-$C_4H_9$ | H | H |
| 31 | 4-Cl | $CH_2Cl$ | H | H |
| 32 | 4-Cl | ◁ | H | H |
| 33 | 4-Cl | —CHCl$CH_3$ | H | H |
| 34 | 2-Cl | $CHCl_2$ | H | H |
| 35 | 4-Cl | $CF_3$ | H | H |
| 36 | 3,4-Cl | $C_2H_5$ | H | H |
| 37 | 3,4-Cl | i-$C_3H_7$ | H | 4-F |
| 38 | 3,4-Cl | n-$C_3H_7$ | H | H |
| 39 | 3,4-Cl | sec-$C_4H_9$ | H | H |
| 40 | 3,4-Cl | i-$C_3H_7$ | H | 3-F |
| 41 | H | $CHCl_2$ | H | H |
| 42 | H | $CH_3$ | H | H |
| 43 | H | i-$C_3H_7$ | H | H |
| 44 | 4-F | $CHCl_2$ | H | H |
| 45 | 4-F | ◁ | H | H |
| 46 | 4-F | i-$C_3H_7$ | H | H |
| 47 | 3-F | i-$C_3H_7$ | H | H |
| 48 | 4-F | t-$C_4H_9$ | H | H |
| 49 | 4-F | —C=$CCl_2$<br>Cl | H | H |
| 50 | 4-F | $CHF_2$ | H | H |
| 51 | 2,3,4,5,6-F | i-$C_3H_7$ | H | H |
| 52 | 2,4-F | i-$C_3H_7$ | H | H |
| 53 | 4-F | i-$C_3H_7$ | 4-F | H |
| 54 | 3,4-F | i-$C_3H_7$ | H | H |
| 55 | 3,5-F | i-$C_3H_7$ | H | H |
| 56 | 2,5-F | i-$C_3H_7$ | H | H |
| 57 | 2,3,5,6-F | i-$C_3H_7$ | H | H |
| 58 | 2,4,5-F | i-$C_3H_7$ | H | H |
| 59 | 2,4-F | $C_2H_5$ | H | H |
| 60 | 3,4-F | i-$C_3H_7$ | H | 4-F |
| 61 | 4-$CF_3$ | $CHCl_2$ | H | H |
| 62 | 4-$CF_3$ | ◁ | H | H |
| 63 | 4-$OCF_3$ | ◁ | H | H |

TABLE 1-continued

($R_1$ = unsubstituted or substituted phenyl)

| Cmpd. No. | Phenyl Subst. | $R_2$ | $R_4$ | $R_5$ |
|---|---|---|---|---|
| 64 | 4-OCF$_3$ | CHCl$_2$ | H | H |
| 65 | 2-Cl,4-CF$_3$ |  | H | H |
| 66 | 3-CF$_3$ | CHCl$_2$ | H | H |
| 67 | 3-CF$_3$ | i-C$_3$H$_7$ | H | H |
| 68 | 4-CF$_3$ | i-C$_3$H$_7$ | H | H |
| 69 | 2,5-OCH$_3$ | i-C$_3$H$_7$ | H | H |
| 70 | 4-OCF$_3$ | i-C$_3$H$_7$ | H | H |
| 71 | 3-CF$_3$,4-Cl | i-C$_3$H$_7$ | H | H |
| 72 | 2-CF$_3$ | i-C$_3$H$_7$ | H | H |
| 73 | 2-CH$_3$,3-F | i-C$_3$H$_7$ | H | H |
| 74 | 2-CH$_3$,5-F | i-C$_3$H$_7$ | H | H |
| 75 | 3-F,4-CH$_3$ | i-C$_3$H$_7$ | H | H |
| 76 | 3-OCH$_3$,5-CF$_3$ | i-C$_3$H$_7$ | H | H |
| 77 | 3-CF$_3$,5-F | i-C$_3$H$_7$ | H | H |
| 78 | 3,5-CF$_3$ | i-C$_3$H$_7$ | H | H |
| 79 | 2-F,4-Br | i-C$_3$H$_7$ | H | H |
| 80 | 3-CF$_3$ | i-C$_3$H$_7$ | 4-F | H |
| 81 | 3-Cl,4-F | i-C$_3$H$_7$ | H | H |
| 82 | 3-Cl,4-F | i-C$_3$H$_7$ | 4-F | H |
| 83 | 3-Cl,4-CF$_3$ | i-C$_3$H$_7$ | H | H |
| 84 | 2-F,5-CF$_3$ | i-C$_3$H$_7$ | H | H |
| 85 | 3-Cl,4-F | C$_2$H$_5$ | H | H |
| 86 | 3-CF$_3$ | 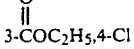 | H | H |
| 87 | 3-CH$_3$,4-F | i-C$_3$H$_7$ | H | H |
| 88 | 3-CF$_3$ | t-C$_4$H$_9$ | H | H |
| 89 | 3-Cl,4-F | i-C$_3$H$_7$ | H | 4-F |
| 90 | 3-Cl,4-CH$_3$ | i-C$_3$H$_7$ | H | H |
| 91 | 3,5-Cl,4-OCH$_3$ | i-C$_3$H$_7$ | H | H |
| 92 | 2,6-Cl,4-NO$_2$ | i-C$_3$H$_7$ | H | H |
| 93 | 2-Cl,5-CH$_3$ | i-C$_3$H$_7$ | H | H |
| 94 | 2-Cl,4-CH$_3$ | i-C$_3$H$_7$ | H | H |
| 95 | 3-Cl,4-OCH$_3$ | i-C$_3$H$_7$ | H | H |
| 96 | 2-CH$_3$,4-Cl | i-C$_3$H$_7$ | H | H |
| 97 | 2-CH$_3$,3-Cl | CHCl$_2$ | H | H |
| 98 | (4-chloro-alpha-naphthyl) | CHCl$_2$ | H | H |
| 99 | 2,5-OCH$_3$,4-Cl | i-C$_3$H$_7$ | H | H |
| 100 | 2-Cl,3,6-OCH$_3$ | i-C$_3$H$_7$ | H | H |
| 101 | 3,5-Cl,4-CH$_3$ | i-C$_3$H$_7$ | H | H |
| 102 | 3-COC$_2$H$_5$,4-Cl (O=) | i-C$_3$H$_7$ | H | H |
| 103 | 3-Cl,4-SC$_2$H$_5$ | i-C$_3$H$_7$ | H | H |
| 104 | 3-Cl,4-COC$_2$H$_5$ (O=) | i-C$_3$H$_7$ | H | H |
| 105 | 3-NO$_2$,4-Cl | t-C$_4$H$_9$ | H | H |
| 106 | 3-Cl,4-Br | t-C$_4$H$_9$ | H | H |
| 107 | 3-Cl,4-CH$_3$ | t-C$_4$H$_9$ | H | H |
| 108 | 3-Cl,4-CN | —C(CH$_3$)$_2$Cl | H | H |
| 109 | 2-CH$_3$,4-Cl | t-C$_4$H$_9$ | H | H |
| 110 | 3-Cl,4-OCH$_3$ | i-C$_3$H$_7$ | H | 4-F |
| 111 | (4-chloro-alpha-naphthyl) | —C(CH$_3$)$_2$Cl | H | H |
| 112 | 3-Cl,4-SO2C$_2$H$_5$ | i-C$_3$H$_7$ | H | H |
|  |  |  | H | H |

TABLE 1-continued

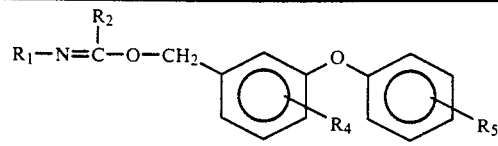

($R_1$ = unsubstituted or substituted phenyl)

| Cmpd. No. | Phenyl Subst. | $R_2$ | $R_4$ | $R_5$ |
|---|---|---|---|---|
| 113 | 3-Cl,4-F | cyclopropyl | H | H |
| 114 | 3-(pyrid-2-yloxy) | i-$C_3H_7$ | H | H |
| 115 | 3-Cl,4-F | $C_2H_5$ | H | 4-F |
| 116 | 3-Cl,4F | cyclopropyl | H | 4-F |
| 117 | 3-Cl,4-F | $C_2F_5$ | H | H |
| 118 | 3-Cl,4-F | $CHBrCH_3$ | H | H |
| 119 | 3-Cl,4-F | i-$C_3H_7$ | H | 2-F |
| 120 | 3-$CF_3$,4-F | i-$C_3H_7$ | H | 4-F |
| 121 | 3-Cl,4-F | n-$C_4H_9$ | H | H |
| 122 | 3-Cl,4-F | sec-$C_4H_9$ | H | H |
| 123 | 3-Cl,4-F | n-$C_3H_7$ | H | H |
| 124 | 3-Cl,4-F | tetramethylcyclopropyl | H | H |
| 125 | 3-Cl,4-F | i-$C_3H_7$ | H | 3-F |
| 126 | 3-CN | i-$C_3H_7$ | H | H |
| 127 | 3-$CH_3$,4-Br | i-$C_3H_7$ | H | H |
| 128 | 3-Br | i-$C_3H_7$ | H | H |
| 129 | 2,4-F,6-Br | i-$C_3H_7$ | H | H |
| 130 | 2,6-Br,4-F | i-$C_3H_7$ | H | H |
| 131 | 4-Br | i-$C_3H_7$ | H | H |
| 132 | 2-Br | i-$C_3H_7$ | H | H |
| 133 | 2-$CH_3$,4-Br | i-$C_3H_7$ | H | H |
| 134 | 3-Br | t-$C_4H_9$ | H | H |
| 135 | 4-Br | t-$C_4H_9$ | H | H |
| 136 | 3-I | i-$C_3H_7$ | H | H |
| 137 | 4-I | i-$C_3H_7$ | H | H |
| 138 | 4-$OC_2H_5$ | $CHCl_2$ | H | H |
| 139 | 4-$CH_3$ | $CHCl_2$ | H | H |
| 140 | 4-(t-$C_4H_9$) | $CHCl_2$ | H | H |
| 141 | 4-$SCH_3$ | $CHCl_2$ | H | H |
| 142 | 4-$SCH_3$ | i-$C_3H_7$ | H | H |
| 143 | 3-$OCH_3$ | i-$C_3H_7$ | H | H |
| 144 | 4-(i-$C_3H_7$) | i-$C_3H_7$ | H | H |
| 145 | 2-$OCH_3$ | i-$C_3H_7$ | H | H |
| 146 | 2,4-$OCH_3$ | i-$C_3H_7$ | H | H |
| 147 | 4-C(=O)-$CH_3$ | i-$C_3H_7$ | H | H |
| 148 | 2,3-$CH_3$ | i-$C_3H_7$ | H | H |
| 149 | 2-$CH_3$,4-$OCH_3$ | i-$C_3H_7$ | H | H |
| 150 | 2-$OCH_3$,5-$CH_3$ | i-$C_3H_7$ | H | H |
| 151 | 4-$COCH_3$ (C=O) | i-$C_3H_7$ | H | H |
| 152 | 4-(n-$C_4H_9$) | i-$C_3H_7$ | H | H |
| 153 | 4-(t-$C_4H_9$) | i-$C_3H_7$ | H | H |
| 154 | 3-$C_2H_5$ | i-$C_3H_7$ | H | H |
| 155 | 3-$CH_3$ | i-$C_3H_7$ | H | H |
| 156 | 4-$CH_3$ | i-$C_3H_7$ | H | H |
| 157 | 4-$C_2H_5$ | $C_2H_5$ | H | H |
| 158 | 3,4-$CH_3$ | i-$C_3H_7$ | H | H |
| 159 | 4-$C_2H_5$ | i-$C_3H_7$ | H | 4-F |
| 160 | 4-$OCH_3$ | i-$C_3H_7$ | H | H |
| 161 | 4-$C_2H_5$ | i-$C_3H_7$ | H | H |
| 162 | 3-$C_2H_5$ | t-$C_4H_9$ | H | H |

TABLE 1-continued

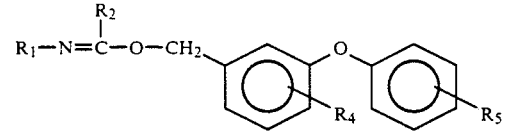

(R₁ = unsubstituted or substituted phenyl)

| Cmpd. No. | Phenyl Subst. | $R_2$ | $R_4$ | $R_5$ |
|---|---|---|---|---|
| 163 | 4-$C_2H_5$ | t-$C_4H_9$ | H | H |
| 164 | 4-$OC_2H_5$ | t-$C_4H_9$ | H | H |
| 165 | 4-(i-$C_3H_7$) | t-$C_4H_9$ | H | H |
| 166 | 3-$SCH_3$ | i-$C_3H_7$ | H | H |
| 167 | 3,4-$CH_3$ | t-$C_4H_9$ | H | H |
| 168 | 3-$COC_2H_5$ (O=) | t-$C_4H_9$ | H | H |
| 169 | 3,4-$OCH_3$ | i-$C_3H_7$ | H | H |
| 170 | 3-$\overset{O}{\overset{\|}{C}}$—$CH_3$ | i-$C_3H_7$ | H | H |
| 171 | 3-$OC_2H_5$ | i-$C_3H_7$ | H | H |
| 172 | 4-CN | i-$C_3H_7$ | H | H |
| 173 | 4-$NO_2$ | $CHCl_2$ | H | H |
| 174 | 3-$NO_2$ | $CHCl_2$ | H | H |
| 175 | 3-$NO_2$ | t-$C_4H_9$ | H | H |
| 176 | 3,4-(—$OCH_2O$—) | i-$C_3H_7$ | H | 4-F |
| 177 | 3,4-(—$OCH_2O$—) | 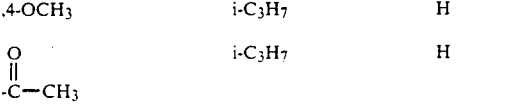 | H | H |
| 178 | 3,4-(—$OCH_2O$—) | $C_2H_5$ | H | H |
| 179 | 3,4-($OC_2H_4O$—) | i-$C_3H_7$ | H | H |
| 180 | 3,4-(—$OCH_2O$—) | i-$C_3H_7$ | H | H |
| 181 | 3,4-(—$OCH_2O$—) | i-$C_3H_7$ | 4-F | H |
| 182 | 3,4-[—$OC(CH_3)_2O$—] | i-$C_3H_7$ | H | H |
| 183 | 3,4-($OCH_2O$—) | i-$C_3H_7$ | H | 2-F |
| 184 | 4-$OCH_3$ | n-$C_3H_7$ | H | H |
| 185 | 3,4-($OCH_2O$—) | sec-$C_4H_9$ | H | H |
| 186 | 4-$C_6H_5$ | i-$C_3H_7$ | H | H |
| 187 | 3,4-(—$CH_2CH_2CH_2$—) | i-$C_3H_7$ | H | H |
| 188 | 3-4-(—$OCH_2O$—) | n-$C_3H_7$ | H | H |
| 189 | 4-Cl | i-$C_3H_7$ | H | 4-F |
| 190 | 3,4-(—$OCH_2O$—) | i-$C_3H_7$ | H | 2-F |
| 191 | 3-Cl,4-F | i-$C_3H_7$ | H | 2,4-F |
| 192 | 3-$CF_3$ | i-$C_3H_7$ | H | 3-F |
| 193 | 3-$CF_3$,4-Cl | i-$C_3H_7$ | H | 4-F |
| 194 | 3-Cl | i-$C_3H_7$ | H | 4-F |
| 195 | 3-$CF_3$,4-Cl | i-$C_3H_7$ | H | 3-F |
| 196 | 3-Cl,4-F | i-$C_3H_7$ | H | 4-CN |
| 197 | 4-F | i-$C_3H_7$ | H | 4-F |
| 198 | 2,3,4,5,6-F | i-$C_3H_7$ | H | 4-F |
| 199 | 3,5-F | i-$C_3H_7$ | H | 4-F |
| 200 | 3-F | i-$C_3H_7$ | H | 4-F |
| 201 | 3-$OCH_3$ | i-$C_3H_7$ | H | 4-F |
| 202 | 3-$CF_3$ | i-$C_3H_7$ | H | 4-F |
| 203 | 3-Cl,4-F | i-$C_3H_7$ | H | 3-Cl |
| 204 | 3-Cl,4-F | t-$C_4H_9$ | H | 4-F |
| 205 | 4-F | i-$C_3H_7$ | H | 3-Cl |
| 206 | 4-F | i-$C_3H_7$ | H | 2,4-F |
| 207 | 3,4-Cl | i-$C_3H_7$ | H | 3-Cl |
| 208 | 4-CN | i-$C_3H_7$ | H | 3-Cl |
| 209 | 2,4-F | i-$C_3H_7$ | H | 4-F |
| 210 | 3-Cl,4-F | sec-$C_4H_9$ | H | 4-F |
| 211 | 3,4-Cl | sec-$C_4H_9$ | H | 4-F |
| 212 | 3,4-F | i-$C_3H_7$ | H | 4-CN |
| 213 | 3,4-Cl | i-$C_3H_7$ | H | 2,4-F |
| 214 | 3,4-F | i-$C_3H_7$ | H | 2,4-F |
| 215 | 3-Cl,4-F | i-$C_3H_7$ | H | 3,5-F |
| 216 | 3-Cl,4-F | i-$C_3H_7$ | 4-F | 4-F |
| 217 | 3-Cl,4-F | i-$C_3H_7$ | H | 3,4-F |
| 218 | 3,4-Cl | i-$C_3H_7$ | H | 3,4-F |
| 219 | 3-4-[—$OC(CH_3)_2O$—] | i-$C_3H_7$ | H | 4-F |
| 220 | 4-F | i-$C_3H_7$ | H | 4-$OCH_3$ |

TABLE 1-continued

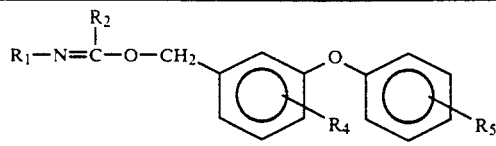

($R_1$ = unsubstituted or substituted phenyl)

| Cmpd. No. | Phenyl Subst. | $R_2$ | $R_4$ | $R_5$ |
|---|---|---|---|---|
| 221 | 3-Cl,4-F | i-$C_3H_7$ | H | 4-$OCH_3$ |
| 222 | 3-F,4-CN | i-$C_3H_7$ | H | 4-F |
| 223 | 3,4-Cl | i-$C_3H_7$ | H | 4-$OCH_3$ |
| 224 | 3-Cl,4-F | —C($CH_3$)$_2$Cl | H | 4-F |
| 225 | 3-Cl,4-F | i-$C_3H_7$ | H | 4-$CH_3$ |
| 226 | 4-Br | i-$C_3H_7$ | H | 4-F |
| 227 | 4-CN | i-$C_3H_7$ | H | 4-F |
| 228 | 4-(i-$C_3H_7$) | i-$C_3H_7$ | H | 4-F |
| 229 | 3-Br | i-$C_3H_7$ | H | 4-F |
| 230 | 3-Cl,4-F | i-$C_3H_7$ | 6-F | 4-F |
| 231 | 4-F | i-$C_3H_7$ | H | 4-$CH_3$ |
| 232 | 2,3,4,5,6-F | i-$C_3H_7$ | H | 2,4-F |
| 233 | 3-F,4-CN | i-$C_3H_7$ | H | H |
| 234 | 4-I | i-$C_3H_7$ | H | 4-F |
| 235 | 4-(t-$C_4H_9$) | i-$C_3H_7$ | H | 4-F |
| 236 | 3-$CH_3$,4-F | i-$C_3H_7$ | H | 4-F |
| 237 | 4-Cl | i-$C_3H_7$ | H | 4-Br |
| 238 | 3-Cl,4-F | i-$C_3H_7$ | H | 4-Br |
| 239 | 3-Cl,4-F | i-$C_3H_7$ | H | 4-Cl |
| 240 | 3,4-(—$OCH_2O$—) | i-$C_3H_7$ | H | 4-Cl |
| 241 | 3,4-[—OC($CH_3$)$_2$O—] | i-$C_3H_7$ | H | 4-Cl |
| 242 | 3,4-[—OC($CH_3$)$_2$O—] | i-$C_3H_7$ | 4-F | H |
| 243 | 3,4-(—$CH_2CH_2O$—) | i-$C_3H_7$ | H | H |
| 244 | 3,4-(—$OCF_2O$—) | i-$C_3H_7$ | H | 4-F |
| 245 | 3,4-(—$OCF_2O$—) | i-$C_3H_7$ | H | H |
| 246 | 3,4-(—$OCH_2O$—) | i-$C_3H_7$ | H | 4-$CF_3$ |
| 247 | 3-Cl,4-F | i-$C_3H_7$ | H | 4-$CF_3$ |
| 248 | 3,4,5-$OCH_3$ | i-$C_3H_7$ | H | H |
| 249 | 2,3-$CH_3$ | i-$C_3H_7$ | H | H |
| 250 | 2,5-$CH_3$ | i-$C_3H_7$ | H | H |
| 251 | 3,4-Br | i-$C_3H_7$ | H | 4-F |
| 252 | 3,4-Br | i-$C_3H_7$ | H | H |
| 253 | 3-Br,4-F | i-$C_3H_7$ | H | 4-F |
| 254 | 3-Br,4-F | i-$C_3H_7$ | H | H |
| 255 | 3-I | i-$C_3H_7$ | H | 4-F |
| 256 | 3-Cl,4-F | i-$C_3H_7$ | H | 4-$SCH_3$ |
| 257 | 4-F | i-$C_3H_7$ | H | 4-$SCH_3$ |
| 258 | 3-Cl,4-F | $C_2F_5$ | H | 4-F |
| 259 | 4-F | i-$C_3H_7$ | H | 4-Br |
| 260 | 3-Cl | i-$C_3H_7$ | H | 4-Br |
| 261 | 3-Cl,4-F | sec-$C_4H_9$ | 4-F | H |
| 262 | 3-Cl,4-F | i-$C_3H_7$ | 2-F | 4-F |
| 263 | 2-$CH_3$,5-Cl | i-$C_3H_7$ | H | H |
| 264 | 2-$OCH_3$,5-Cl | i-$C_3H_7$ | H | H |
| 265 | 4-F | i-$C_3H_7$ | H | 3,4-F |
| 266 | 3-$CF_3$ | i-$C_3H_7$ | 4-F | 4-Cl |
| 267 | 3-Cl,4-F | i-$C_3H_7$ | 4-F | 4-Cl |
| 268 | 3-$CF_3$ | i-$C_3H_7$ | 4-F | 4-F |
| 269 | 4-Cl | i-$C_3H_7$ | H | 4-Cl |
| 270 | 3-Cl | i-$C_3H_7$ | H | 4-Cl |
| 271 | 3-$NO_2$ | i-$C_3H_7$ | H | 4-Cl |
| 272 | 3-$SCF_3$ | i-$C_3H_7$ | H | 4-F |
| 273 | 3-Br,4-F | i-$C_3H_7$ | 4-F | 4-F |
| 274 | 3,4-(—$OCH_2O$—) | i-$C_3H_7$ | 6-Cl | 4-F |
| 275 | 3,4-F | i-$C_3H_7$ | H | 4-Br |
| 276 | 3-Br,4-F | i-$C_3H_7$ | H | 4-Br |
| 277 | 3-$CF_3$,4-F | i-$C_3H_7$ | 4-F | 4-F |
| 278 | 3,4-F | i-$C_3H_7$ | 4-F | 4-F |
| 279 | 3-I | i-$C_3H_7$ | 4-F | 4-F |
| 280 | 4-[cyclohexyl-S] | i-$C_3H_7$ | H | 4-F |
| 281 | 3-I,4-F | i-$C_3H_7$ | 4-F | 4-F |
| 282 | 3-F,4-Br | i-$C_3H_7$ | 4-F | 4-F |
| 283 | 3,4-[OC($CH_3$)$_2$O—] | i-$C_3H_7$ | 4-F | 4-F |
| 284 | 3,4-(—$OCF_2O$—) | i-$C_3H_7$ | 4-F | 4-F |

TABLE 1-continued $$R_1-N=\underset{R_2}{C}-O-CH_2-\underset{R_4}{\bigcirc}-O-\underset{R_5}{\bigcirc}$$

($R_1$ = unsubstituted or substituted phenyl)

| Cmpd. No. | Phenyl Subst. | $R_2$ | $R_4$ | $R_5$ |
|---|---|---|---|---|
| 285 | 3,4-(—OCF$_2$O—) | i-C$_3$H$_7$ | 4-F | H |
| 286 | 4-OCF$_3$ | i-C$_3$H$_7$ | 4-F | 4-F |
| 287 | 4-CF$_3$ | i-C$_3$H$_7$ | 4-F | 4-F |
| 288 | 3-OCF$_2$CHF$_2$ | i-C$_3$H$_7$ | H | 4-F |
| 289 | 3,4-Cl | i-C$_3$H$_7$ | 4-F | 4-F |
| 290 | 4-Cl | —CH(C$_2$H$_5$)$_2$ | H | 4-F |
| 291 | 3-CF$_3$ | —CH(C$_2$H$_5$)$_2$ | H | 4-F |
| 292 | 2,4-Cl,5-F | i-C$_3$H$_7$ | 4-F | 4-F |
| 293 | 3-NO$_2$,4-F | i-C$_3$H$_7$ | H | H |
| 294 | 3-CF$_3$ |  | H | 4-F |
| 295 | 3,4-F | i-C$_3$H$_7$ | 4-F | 4-Cl |
| 296 | 3,4-Cl | i-C$_3$H$_7$ | 4-F | 4-Cl |
| 297 | 3-CF$_3$,4-F | i-C$_3$H$_7$ | 4-F | 4-Cl |
| 298 | 3-Br,4-F | i-C$_3$H$_7$ | 4-F | 4-Cl |
| 299 | 3-Br,4-F | i-C$_3$H$_7$ | 4-F | H |
| 300 | 3-CF$_3$,4-F | i-C$_3$H$_7$ | 4-F | H |
| 301 | 4-(t-C$_4$H$_9$) | i-C$_3$H$_7$ | 4-F | 4-Cl |
| 302 | 3-NO$_2$ | i-C$_3$H$_7$ | H | H |
| 303 | 2-Cl,5-F | i-C$_3$H$_7$ | 4-F | 4-F |
| 304 | 2,3,5,6-F | i-C$_3$H$_7$ | H | 4-F |
| 305 | 3-Cl,4-F | CHBrCH$_3$ | H | 4-F |
| 306 | 3,4-(OCH$_2$O—) | CHBrCH$_3$ | H | H |
| 307 | 3-CF$_3$,4-NO2 | i-C$_3$H$_7$ | H | H |
| 308 | 3-Cl,4-(t-C$_4$H$_9$) | i-C$_3$H$_7$ | H | 4-F |
| 309 | 3-Cl,4-F | CF(CH$_3$)$_2$ | H | 4-F |
| 310 | 3-Cl,4-F | CF(CH$_3$)$_2$ | 4-F | 4-F |
| 311 | 2,4-Cl | i-C$_3$H$_7$ | H | H |
| 312 | 2,4-Cl | i-C$_3$H$_7$ | H | 4-F |
| 313 | 3,4-(—OCH$_2$O—) | i-C$_3$H$_7$ | 4-F | 4-Cl |
| 314 | 4-CF$_3$ | i-C$_3$H$_7$ | 4-F | 4-F |
| 315 | 3-Cl,4-F | CF(CH$_3$)$_2$ | H | 2,4-F |
| 316 | 3-Cl,4-F | CF(CH$_3$)$_2$ | 6-F | 4-F |
| 317 | 4-(i-C$_3$H$_7$) | sec-C$_4$H$_9$ | H | H |
| 318 | 3,4-F | CF(CH$_3$)$_2$ | H | 4-F |
| 319 | 3-CF$_3$ | CF(CH$_3$)$_2$ | H | 4-F |
| 320 | 4-(i-C$_3$H$_7$) | C$_2$H$_5$ | H | 4-F |
| 321 | 4-(i-C$_3$H$_7$) | CH(C$_2$H$_5$)$_2$ | H | H |
| 322 | 4-(i-C$_3$H$_7$) | t-C$_4$H$_9$ | H | 4-F |
| 323 | 4-OCF$_3$ | i-C$_3$H$_7$ | 4-F | 4-Cl |
| 324 | 4-CF$_3$ | i-C$_3$H$_7$ | 4-F | 4-Cl |
| 325 | 4-F | i-C$_3$H$_7$ | 4-F | 4-Cl |
| 326 | 3-I,4-F | i-C$_3$H$_7$ | 4-F | 4-Cl |
| 327 | 3-Cl,4-F | i-C$_3$H$_7$ | 5-F | 4-F |
| 328 | 3-Cl,4-CF$_3$ | i-C$_3$H$_7$ | 5-F | 4-F |
| 329 | 4-(i-C$_3$H$_7$) | i-C$_4$H$_9$ | H | 4-F |
| 330 | 2,4-F,3-Cl | i-C$_3$H$_7$ | 4-F | 4-F |
| 331 | 2,4-F,3-Cl | i-C$_3$H$_7$ | H | 4-Cl |
| 332 | 2,4-F,3-Cl | i-C$_3$H$_7$ | H | H |
| 333 | 4-Br | i-C$_3$H$_7$ | 4-F | 4-F |
| 334 | 3-I,4-F | i-C$_3$H$_7$ | 4-F | H |
| 335 | 4-I | i-C$_3$H$_7$ | 4-F | 4-F |
| 336 | 3,4-F | i-C$_3$H$_7$ | 4-F | H |
| 337 | 4-CF$_3$ | i-C$_3$H$_7$ | 4-F | H |
| 338 | 4-OCF$_3$ | i-C$_3$H$_7$ | 4-F | H |
| 339 | 4-(i-C$_3$H$_7$) | 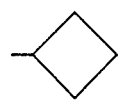 | H | H |
| 340 | 3-CF$_3$,4-Cl | i-C$_3$H$_7$ | 4-F | 4-F |
| 341 | 3-Cl | i-C$_3$H$_7$ | 4-F | 4-F |
| 342 | 3-F | i-C$_3$H$_7$ | 4-F | 4-F |
| 343 | 3-Cl,4-F | i-C$_3$H$_7$ | 4,6-F | 4-F |
| 344 | 4-(t-C$_4$H$_9$) | i-C$_3$H$_7$ | H | 4-CH$_3$ |

TABLE 1-continued

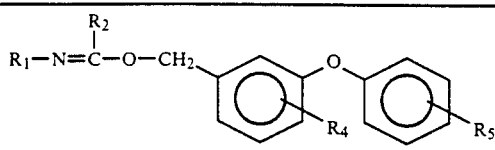

($R_1$ = unsubstituted or substituted phenyl)

| Cmpd. No. | Phenyl Subst. | $R_2$ | $R_4$ | $R_5$ |
|---|---|---|---|---|
| 345 | 4-(t-$C_4H_9$) | i-$C_3H_7$ | H | 4-$OCH_3$ |
| 346 | 3-Cl,4-F | i-$C_3H_7$ | 4-F | 3,4-F |
| 347 | 4-$OCF_3$ | i-$C_3H_7$ | 4-F | 3,4-F |
| 348 | 2,3,4-F | i-$C_3H_7$ | H | 4-F |
| 349 | 2,3,4-F | i-$C_3H_7$ | 4-F | 4-F |
| 350 | 3-(t-$C_4H_9$) | i-$C_3H_7$ | H | 4-F |
| 351 | 2-F,4-Br | i-$C_3H_7$ | H | 4-F |
| 352 | 2,4-F,3-Cl | i-$C_3H_7$ | H | 4-F |
| 353 | 4-$SCH_3$ | i-$C_3H_7$ | 4-F | H |
| 354 | 3-F,4-$CH_3$ | i-$C_3H_7$ | 4-F | H |
| 355 | 3-F,4-$CH_3$ | i-$C_3H_7$ | 4-F | 4-F |
| 356 | 3-Cl,4-$CH_3$ | i-$C_3H_7$ | 4-F | H |
| 357 | 3-Cl,4-$CH_3$ | i-$C_3H_7$ | 4-F | 4-F |
| 358 | 3-$CH_3$,4-Br | i-$C_3H_7$ | 4-F | H |
| 359 | 3-$CH_3$,4-Br | i-$C_3H_7$ | 4-F | 4-F |
| 360 | 4-$C_2H_5$ | i-$C_3H_7$ | 4-F | H |
| 361 | 4-$C_2H_5$ | i-$C_3H_7$ | 4-F | 4-F |
| 362 | 3-$SCH_3$ | i-$C_3H_7$ | 4-F | H |
| 363 | 3,4-$OCH_3$ | i-$C_3H_7$ | 4-F | 4-F |
| 364 | 3-$CF_3$,4-Br | i-$C_3H_7$ | 4-F | 4-F |
| 365 | 4-$CF_3$ | i-$C_3H_7$ | H | 4-Cl |
| 366 | 3,4-(—$OCH_2O$—) | i-$C_3H_7$ | 4-F | 4-Cl |
| 367 | 3,4-(—$OCH_2O$—) | i-$C_3H_7$ | H | 4-(t-$C_4H_9$) |
| 368 | 3-Cl,4-$OC_2H_5$ | i-$C_3H_7$ | H | H |
| 369 | 3-Cl,4-$OC_2H_5$ | i-$C_3H_7$ | 4-F | 4-Cl |
| 370 | 3-Cl,4-$OC_2H_5$ | i-$C_3H_7$ | 4-F | H |
| 371 | 4-$OC_2H_5$ | i-$C_3H_7$ | H | H |
| 372 | 4-$OC_2H_5$ | i-$C_3H_7$ | 4-F | 4-Cl |
| 373 | 4-$OC_2H_5$ | i-$C_3H_7$ | 4-F | H |
| 374 | 3-Cl,4-I | i-$C_3H_7$ | H | 4-F |
| 375 | 3-F | i-$C_3H_7$ | 4-F | 4-Cl |
| 376 | 3,4-Cl | i-$C_3H_7$ | 4-F | H |
| 377 | 3-Br,4-$CF_3$ | i-$C_3H_7$ | 4-F | 4-Cl |
| 378 | 4-Br | i-$C_3H_7$ | 4-F | 4-Cl |
| 379 | 3-Br,4-F | i-$C_3H_7$ | 4-F | 4-Cl |
| 380 | 3-Cl,4-Br | 1-$C_3H_7$ | H | 4-Cl |
| 381 | 3-Cl,4-Br | i-$C_3H_7$ | 4-F | 4-Cl |
| 382 | 3-Cl,4-Br | i-$C_3H_7$ | 4-F | 4-F |
| 383 | 3,4-Br | i-$C_3H_7$ | 4-F | 4-F |
| 384 | 3,4-Br | i-$C_3H_7$ | 4-F | H |
| 385 | 3-Cl,4-I | i-$C_3H_7$ | 4-F | 4-F |
| 386 | 3-Br | i-$C_3H_7$ | 4-F | 4-Cl |
| 387 | 3-Br | i-$C_3H_7$ | 4-F | H |
| 388 | 3-$CF_3$,4-Cl | i-$C_3H_7$ | 4-F | H |
| 389 | 3-I | i-$C_3H_7$ | H | 4-Cl |
| 390 | 3-Cl | i-$C_3H_7$ | 4-F | 4-Cl |
| 391 | 4-Cl | i-$C_3H_7$ | 4-F | 4-Cl |
| 392 | 4-CN | i-$C_3H_7$ | 4-F | 4-Cl |
| 393 | 4-CN | i-$C_3H_7$ | H | 4-Cl |
| 394 | 4-CN | i-$C_3H_7$ | 4-F | 4-F |
| 395 | 2,4-F,3-Cl | i-$C_3H_7$ | 4-F | 4-Cl |
| 396 | 3-$CH_3$,4-F | i-$C_3H_7$ | 4-F | 4-F |
| 397 | 3-$CH_3$,4-F | i-$C_3H_7$ | H | 4-Cl |
| 398 | 3-Br,4-F | i-$C_3H_7$ | H | 4-Cl |
| 399 | 3-$CH_3$,4-F | i-$C_3H_7$ | 4-F | 4-Cl |
| 400 | 3-$CH_3$,4-F | i-$C_3H_7$ | 4-F | H |
| 401 | 3-$CH_3$ | i-$C_3H_7$ | 4-F | 4-Cl |
| 402 | 3-Cl,4-$CH_3$ | i-$C_3H_7$ | H | 4-F |
| 403 | 3-Cl,4-$CH_3$ | i-$C_3H_7$ | H | 4-Cl |
| 404 | 3-Cl,4-$CH_3$ | i-$C_3H_7$ | 4-F | 4-Cl |
| 405 | 3-$CH_3$ | i-$C_3H_7$ | H | 4-F |
| 406 | 3,4-$CH_3$ | i-$C_3H_7$ | 4-F | 4-Cl |
| 407 | 3-$CH_3$,4-Br | i-$C_3H_7$ | 4-F | 4-Cl |
| 408 | 3-Cl,4-$OCH_3$ | i-$C_3H_7$ | 4-F | 4-F |
| 409 | 3-Cl,4-$OCH_3$ | i-$C_3H_7$ | 4-F | H |
| 410 | 3-Cl,4-$OCH_3$ | i-$C_3H_7$ | 4-F | 4-Cl |
| 411 | 2-$C_2H_5$ | i-$C_3H_7$ | H | 4-F |
| 412 | 4-$OCH_3$ | i-$C_3H_7$ | 4-F | 4-Cl |
| 413 | 3-I,4-F | i-$C_3H_7$ | H | 4-Cl |
| 414 | 4-$SO_2CH_3$ | i-$C_3H_7$ | 4-F | 4-F |

TABLE 1-continued $$R_1-N=\underset{\underset{R_2}{|}}{C}-O-CH_2-\phenyl(R_4)-O-\phenyl(R_5)$$

($R_1$ = unsubstituted or substituted phenyl)

| Cmpd. No. | Phenyl Subst. | $R_2$ | $R_4$ | $R_5$ |
|---|---|---|---|---|
| 415 | 3-Cl,4-F | —C(CH$_3$)=CH$_2$ | 4-F | 4-Cl |
| 416 | 3-Cl,4-F | —C(CH$_3$)=CH$_2$ | 4-F | H |
| 417 | 3-Cl,4-F | —C(CH$_3$)=CH$_2$ | H | H |
| 418 | 4-OCF$_2$CHFCl | i-C$_3$H$_7$ | H | H |
| 419 | 4-OCF$_2$CHFCl | i-C$_3$H$_7$ | 4-F | H |
| 420 | 3-Cl,4-OCH$_2$CF$_3$ | i-C$_3$H$_7$ | H | 4-F |
| 421 | 3-Cl,4-OCH$_2$CF$_3$ | i-C$_3$H$_7$ | H | 4-Cl |
| 422 | 4-OCH$_2$CF$_3$ | i-C$_3$H$_7$ | 4-F | H |
| 423 | 4-OCH$_2$CF$_3$ | i-C$_3$H$_7$ | H | H |
| 424 | 3-Cl,4-OCH$_2$CF$_3$ | i-C$_3$H$_7$ | 4-F | H |
| 425 | 3-Cl,4-OCH$_2$CF$_3$ | i-C$_3$H$_7$ | H | H |
| 426 | 3-OC$_2$H$_5$ | i-C$_3$H$_7$ | 4-F | 4-F |
| 427 | 2-Cl,4-CF$_3$ | i-C$_3$H$_7$ | H | 4-F |
| 428 | 2-Cl,4-CF$_3$ | i-C$_3$H$_7$ | 4-F | H |
| 429 | 3-F,4-OCH$_2$CF$_3$ | i-C$_3$H$_7$ | H | Cl |
| 430 | 4-CF$_3$ | —C(CH$_3$)=CH$_2$ | H | H |
| 431 | 4-CF$_3$ | —C(CH$_3$)=CH$_2$ | 4-F | H |
| 432 | 4-CF$_3$ | —C(CH$_3$)=CH$_2$ | 4-F | 4-Cl |
| 433 | 3-Br,4-CF$_3$ | i-C$_3$H$_7$ | 4-F | 4-Cl |
| 434 | 3-Br,4-CF$_3$ | i-C$_3$H$_7$ | 4-F | H |
| 435 | 3-F,4-OCH$_3$ | i-C$_3$H$_7$ | 4-F | H |
| 436 | 3-OCF$_3$ | i-C$_3$H$_7$ | 4-F | 4-Cl |
| 437 | 3-OCF$_3$ | i-C$_3$H$_7$ | 4-F | H |
| 438 | 3-Cl,4-C2H5 | i-C$_3$H$_7$ | H | 4-F |
| 439 | 3-F,4-OC2H5 | i-C$_3$H$_7$ | 4-F | H |
| 440 | 4-n-C$_3$H$_7$ | i-C$_3$H$_7$ | 4-F | 4-F |
| 441 | 3-F,4-Cl | i-C$_3$H$_7$ | 4-F | 4-F |
| 442 | 4-CF$_3$ | —C(CH$_3$)=CH$_2$ | H | 4-F |
| 443 | 4-CF$_3$ | cyclopropyl | 4-F | H |
| 444 | 4-CF$_3$ | cyclopropyl | 4-F | 4-Cl |
| 445 | 2-NO$_2$,4-CF$_3$ | i-C$_3$H$_7$ | 4-F | H |
| 446 | 3-Br,4-OC$_2$H$_5$ | i-C$_3$H$_7$ | H | 4-F |
| 447 | 3-Cl,4-F | i-C$_3$H$_7$ | H | 4-I |
| 448 | 3-Cl,4-F | i-C$_3$H$_7$ | 4-Cl | 4-F |
| 449 | 3-I,4-F | i-C$_3$H$_7$ | H | 4-F |
| 450 | 3,4-(—OCF$_2$O—) | i-C$_3$H$_7$ | H | 4-Cl |
| 451 | 2,4-F,3-Cl | i-C$_3$H$_7$ | 4-F | H |
| 452 | 3-OCH$_2$CF$_3$,4-Cl | i-C$_3$H$_7$ | 4-F | 4-Cl |

TABLE 2

$$R_1-N=C\begin{matrix}R_2\\OR_3\end{matrix}$$

($R_1$ = unsubstituted or substituted phenyl)

| Cmpd. No. | Phenyl Subst. | $R_2$ | $R_3$ |
|---|---|---|---|
| 453 | 4-Cl | CHCl$_2$ | 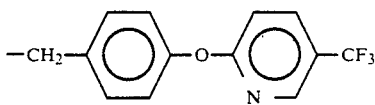 |

TABLE 2-continued $$R_1-N=C\begin{matrix}R_2\\OR_3\end{matrix}$$

($R_1$ = unsubstituted or substituted phenyl)

| Cmpd. No. | Phenyl Subst. | $R_2$ | $R_3$ |
|---|---|---|---|
| 454 | 2,3-Cl | CHCl$_2$ | —CH$_2$—(2,3,4,5,6-pentafluorophenyl) |
| 455 | 4-Cl | i-C$_3$H$_7$ | —CH$_2$—(2-methyl-biphenyl) |
| 456 | 4-F | i-C$_3$H$_7$ | —C$_2$H$_4$—(3-phenoxyphenyl) |
| 457 | 4-Cl | i-C$_3$H$_7$ | —CH(CH$_3$)—(3-phenoxyphenyl) |
| 458 | 4-F | i-C$_3$H$_7$ | —CH$_2$—(2-methyl-biphenyl) |
| 459 | 3-CF$_3$ | i-C$_3$H$_7$ | —CH(CH$_3$)—(3-phenoxyphenyl) |
| 460 | 3-Cl,4-F | i-C$_3$H$_7$ | —CH$_2$—phenyl-O-(2,3,4,5-tetrafluorophenyl) |
| 461 | 3-Cl,4-F | i-C$_3$H$_7$ | —CH$_2$—(pyridyl)-O-(4-fluorophenyl) |
| 462 | 3-Cl,4-F | i-C$_3$H$_7$ | —CH$_2$—(pyridyl)-O-phenyl |
| 463 | 3-Cl,4-F | i-C$_3$H$_7$ | —CH$_2$—(pyridyl)-O-(4-chlorophenyl) |

TABLE 2-continued
$$R_1-N=C\begin{matrix}R_2\\OR_3\end{matrix}$$
($R_1$ = unsubstituted or substituted phenyl)
| Cmpd. No. | Phenyl Subst. | $R_2$ | $R_3$ |
|---|---|---|---|
| 464 | 3,4-(OCH$_2$O—) | i-C$_3$H$_7$ | 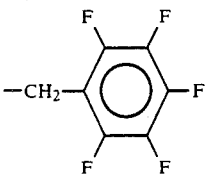 —CH$_2$—C$_6$F$_5$ |
| 465 | 3,4-(OCH$_2$O—) | i-C$_3$H$_7$ | 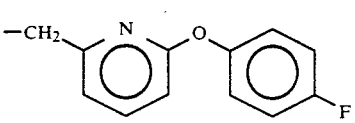 |
| 466 | 3,4-(OCH$_2$O—) | i-C$_3$H$_7$ | 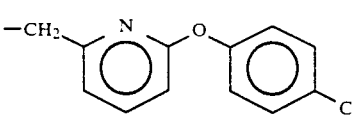 |
| 467 | 3,4-(OCH$_2$O—) | i-C$_3$H$_7$ | 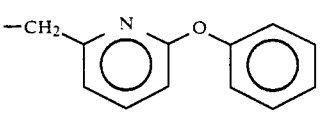 |
| 468 | 3,4-[OC(CH$_3$)2O—] | i-C$_3$H$_7$ | 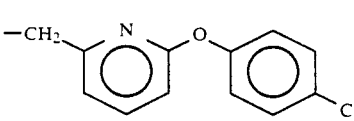 |
| 469 | 3-CF$_3$ | i-C$_3$H$_7$ | 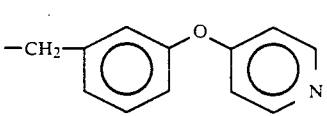 |
| 470 | 3-Cl,4-F | i-C$_3$H$_7$ | 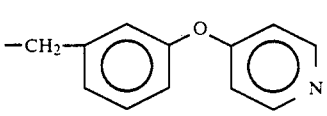 |
| 471 | 3-Cl,4-I | i-C$_3$H$_7$ | 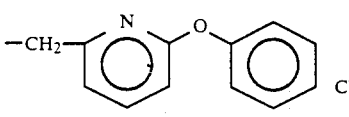 |
| 472 | 3-Cl,4-F | i-C$_3$H$_7$ | 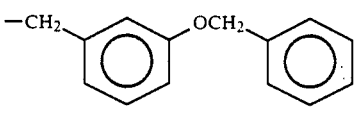 |
| 473 | 3-Cl,4-F | i-C$_3$H$_7$ | 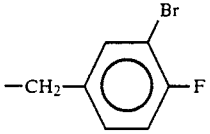 |
| 474 | 3-Cl,4-F | i-C$_3$H$_7$ | 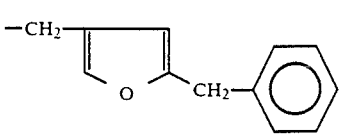 |

TABLE 2-continued
$$R_1-N=C\begin{array}{c}R_2\\ \\OR_3\end{array}$$
($R_1$ = unsubstituted or substituted phenyl)
| Cmpd. No. | Phenyl Subst. | $R_2$ | $R_3$ |
|---|---|---|---|
| 475 | 3-Cl,4-F | i-$C_3H_7$ | 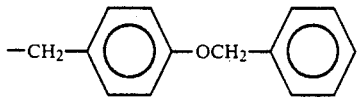 |
| 476 | 3-$CF_3$ | i-$C_3H_7$ | 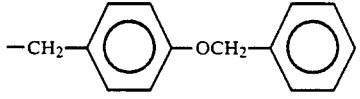 |
| 477 | 3-$CF_3$ | i-$C_3H_7$ | 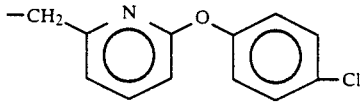 |
| 478 | 4-Br | i-$C_3H_7$ | 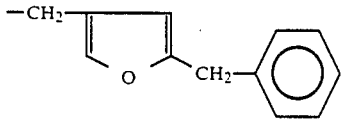 |
| 479 | 3-Cl-4-F | i-$C_3H_7$ | 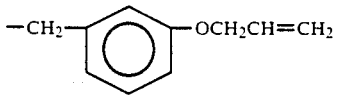 |
| 480 | 3-$CF_3$ | i-$C_3H_7$ | 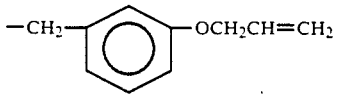 |
| 481 | 3,4-Cl | i-$C_3H_7$ | 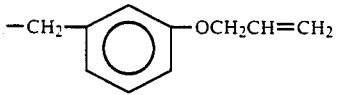 |
| 482 | 3-$CF_3$ | i-$C_3H_7$ | 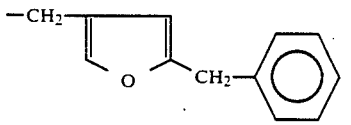 |
| 483 | 3,4-(-OCH$_2$O-) | i-$C_3H_7$ | 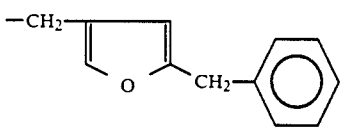 |
| 484 | 4-Cl | i-$C_3H_7$ | 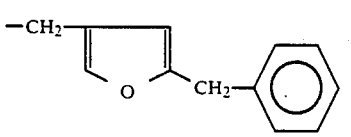 |
| 485 | 3,4-F | i-$C_3H_7$ | 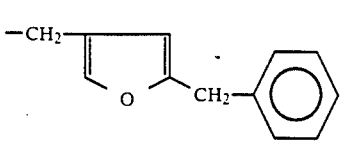 |

TABLE 2-continued
$$R_1-N=C\begin{matrix}R_2\\OR_3\end{matrix}$$
(R$_1$ = unsubstituted or substituted phenyl)
| Cmpd. No. | Phenyl Subst. | R$_2$ | R$_3$ |
|---|---|---|---|
| 486 | 2,4-F | i-C$_3$H$_7$ | 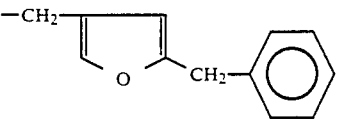 |
| 487 | 3-Cl,4-F | i-C$_3$H$_7$ | 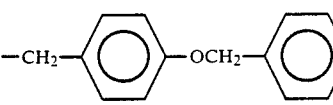 |
| 488 | 3-CF$_3$ | i-C$_3$H$_7$ | 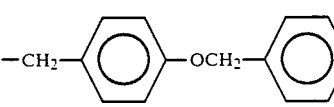 |
| 489 | 3-CF$_3$ | i-C$_3$H$_7$ | 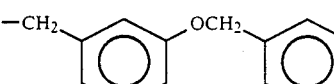 |
| 490 | 3-Cl,4-F | i-C$_3$H$_7$ | 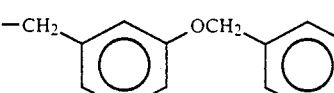 |
| 491 | 4-F | i-C$_3$H$_7$ | 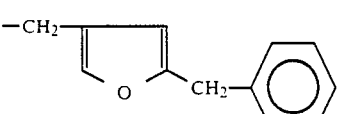 |
| 492 | 3-Cl,4-F | i-C$_3$H$_7$ | 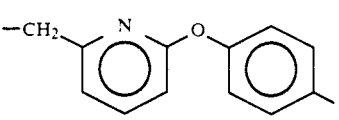 |
| 493 | 3-CF$_3$ | i-C$_3$H$_7$ | 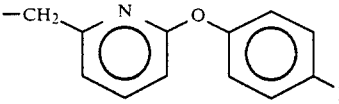 |
| 494 | 3-Cl,4-F | i-C$_3$H$_7$ | 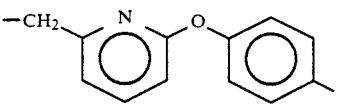 |
| 495 | 3-CF$_3$ | i-C$_3$H$_7$ | 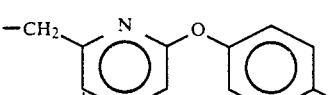 |
| 496 | 4-(t-C$_4$H$_9$) | i-C$_3$H$_7$ | 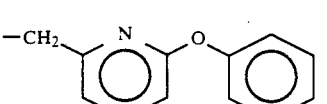 |
| 497 | 4-(t-C$_4$H$_9$) | i-C$_3$H$_7$ | 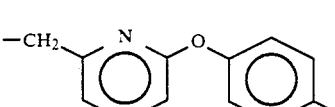 |

TABLE 2-continued $$R_1-N=C\begin{matrix}R_2\\OR_3\end{matrix}$$

($R_1$ = unsubstituted or substituted phenyl)

| Cmpd. No. | Phenyl Subst. | $R_2$ | $R_3$ |
|---|---|---|---|
| 498 | 3-Cl,4-F | i-$C_3H_7$ | —$CH_2$—(6-(1-methylethyl)-2-phenoxypyridin-... ) [CH(CH_3)-pyridyl-O-phenyl] |
| 499 | 3-$CF_3$ | i-$C_3H_7$ | [CH(CH_3)-pyridyl-O-phenyl] |
| 500 | 2,4-F,3-Cl | i-$C_3H_7$ | —$CH_2$-pyridyl-O-(4-Cl-phenyl) |
| 501 | 3,4-(—$OCH_2O$—) | i-$C_3H_7$ | —$CH_2$-(tetrafluorophenyl)-$CH_2OCH_3$ |
| 502 | 3-Cl,4-F | i-$C_3H_7$ | —CHF-phenyl-O-(4-F-phenyl) |
| 503 | 3-$CF_3$ | i-$C_3H_7$ | —$CH_2$-(tetrafluorophenyl)-$CH_2OCH_3$ |
| 504 | 4-$CF_3$ | i-$C_3H_7$ | —$CH_2$-pyridyl-O-phenyl |
| 505 | 3-Cl,4-F | i-$C_3H_7$ | —$CH_2$-(tetrafluorophenyl)-$CH_2OCH_3$ |
| 506 | 3-$CF_3$ | i-$C_3H_7$ | —$CH_2$-pyridyl-O-phenyl |
| 507 | 3-$CF_3$ | i-$C_3H_7$ | —$CH_2$-pyridyl-O-phenyl |

TABLE 2-continued $$R_1-N=C\begin{matrix}R_2\\OR_3\end{matrix}$$

($R_1$ = unsubstituted or substituted phenyl)

| Cmpd. No. | Phenyl Subst. | $R_2$ | $R_3$ |
|---|---|---|---|
| 508 | 3-$CF_3$ | i-$C_3H_7$ | $-CH_2-$(2-pyridyl)-O-(4-fluorophenyl) |
| 509 | 3-$CF_3$ | i-$C_3H_7$ | $-CH_2-$(2-pyridyl)-O-(4-chlorophenyl) |
| 510 | 3-Cl,4-F | i-$C_3H_7$ | $-CH_2-$(2-pyridyl)-O-phenyl |
| 511 | 3-Cl,4-F | i-$C_3H_7$ | $-CH_2-$(2-pyridyl)-O-(4-fluorophenyl) |
| 512 | 3-Cl,4-F | i-$C_3H_7$ | $-CH_2-$phenyl-NH-(4-fluorophenyl) |
| 513 | 3-$CF_3$ | i-$C_3H_7$ | $-CH_2-$phenyl-NH-(4-fluorophenyl) |
| 514 | 3,4-Cl | i-$C_3H_7$ | $-CH_2-$phenyl-NH-(4-fluorophenyl) |
| 515 | 3,4-($OCH_2O-$) | i-$C_3H_7$ | $-CH_2-$(2-pyridyl)-O-(4-fluorophenyl) |
| 516 | 3-Cl,4-F | i-$C_3H_7$ | $-CH_2-$(2-pyridyl)-O-(4-chlorophenyl) |
| 517 | 3-$CF_3$ | i-$C_3H_7$ | $-CH_2-$(2-pyridyl)-O-(4-chlorophenyl) |
| 518 | 3-$CF_3$ | i-$C_3H_7$ | $-CH_2-$phenyl-O-(2-pyridyl-5-chloro) |

TABLE 2-continued
$$R_1-N=C\begin{smallmatrix}R_2\\\\OR_3\end{smallmatrix}$$
($R_1$ = unsubstituted or substituted phenyl)
| Cmpd. No. | Phenyl Subst. | $R_2$ | $R_3$ |
|---|---|---|---|
| 519 | 3-$CF_3$ | i-$C_3H_7$ | 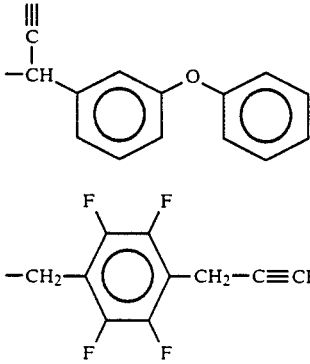 |
| 520 | 3-Cl,4-F | i-$C_3H_7$ | 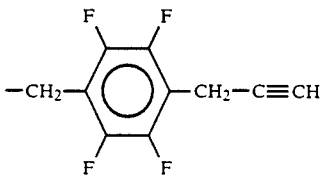 |
| 521 | 2,4-F,3-Cl | i-$C_3H_7$ | 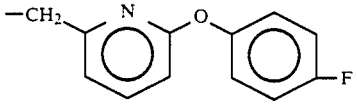 |
| 522 | 2,4-F,3-Cl | i-$C_3H_7$ | 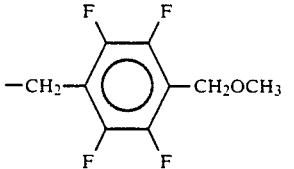 |
| 523 | 3,4-Cl | i-$C_3H_7$ | 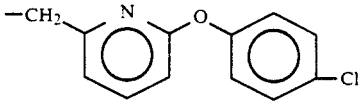 |
| 524 | 3,4-F | $C_2H_5$ | 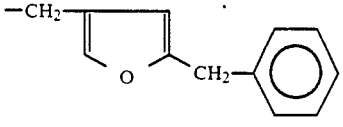 |
| 525 | 3,4-F | t-$C_4H_9$ | 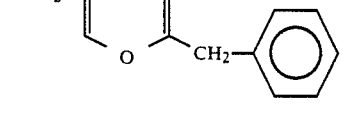 |
| 526 | 3,4-F | $CH_3$ | 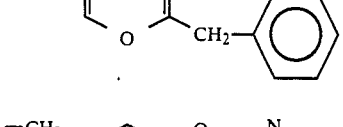 |
| 527 | 3-Cl,4-F | i-$C_3H_7$ |  |
| 528 | 3-$CF_3$ | i-$C_3H_7$ | 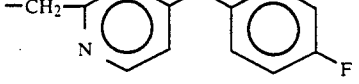 |

TABLE 2-continued $$R_1-N=C\begin{matrix}R_2\\OR_3\end{matrix}$$

($R_1$ = unsubstituted or substituted phenyl)

| Cmpd. No. | Phenyl Subst. | $R_2$ | $R_3$ |
|---|---|---|---|
| 529 | 3-Cl,4-F | i-$C_3H_7$ | —$CH_2$—(2-pyridyl)—O—(4-F-phenyl) |
| 530 | 4-$CF_3$ | i-$C_3H_7$ | —CH—(pyridyl)—O—(4-Cl-phenyl) |
| 531 | 3-Cl,4-F | i-$C_3H_7$ | —$CH_2$—(pyridyl)—O—(3,4-diF-phenyl) |
| 532 | 3,4-(—O$CH_2$O—) | i-$C_3H_7$ | —$CH_2$—(phenyl)—O—(Cl-pyridyl) |
| 533 | 3-Cl,4-F | i-$C_3H_7$ | —CH(C≡CH)—(phenyl)—O—(phenyl) |
| 534 | 3-Cl,4-F | i-$C_3H_7$ | —$CH_2$—C≡C—$CH_2$O—(phenyl) |
| 535 | 4-$CF_3$ | i-$C_3H_7$ | —$CH_2$—(phenyl)—$CH_2$—(phenyl) |
| 536 | 4-(t-$C_4H_9$) | i-$C_3H_7$ | —$CH_2$—(2-$CH_3$-phenyl)—(phenyl) |
| 537 | 3-Cl,4-F | i-$C_3H_7$ | —$CH_2$—(phenyl)—$CH_2$—(phenyl) |
| 538 | 4-O$CF_3$ | i-$C_3H_7$ | —$CH_2$—(phenyl)—$CH_2$—(phenyl) |
| 539 | 4-$NO_2$ | i-$C_3H_7$ | —$CH_2$—(furyl)—$CH_2$—(phenyl) |

TABLE 2-continued $$R_1-N=C\begin{matrix}R_2\\\\OR_3\end{matrix}$$

($R_1$ = unsubstituted or substituted phenyl)

| Cmpd. No. | Phenyl Subst. | $R_2$ | $R_3$ |
|---|---|---|---|
| 540 | 3,4-(OCH$_2$O—) | i-C$_3$H$_7$ | —CH$_2$—(pyridyl)—O—phenyl |
| 541 | 3-Cl,4-F | i-C$_3$H$_7$ | —CH$_2$—phenyl—CH$_2$—phenyl |
| 542 | 4-OCF$_3$ | i-C$_3$H$_7$ | —CH$_2$—phenyl—CH$_2$—phenyl |
| 543 | 4-CF$_3$ | i-C$_3$H$_7$ | —CH$_2$—phenyl—CH$_2$—phenyl |
| 544 | 4-(t-C$_4$H$_9$) | i-C$_3$H$_7$ | —CH$_2$—(tetrafluorophenyl)—CH$_2$OCH$_3$ |
| 545 | 3-CH$_3$ | i-C$_3$H$_7$ | —CH$_2$—(pyridyl)—O—(4-Cl-phenyl) |
| 546 | 3-CF$_3$ | i-C$_3$H$_7$ | —CH$_2$—(tetrafluorophenyl)—CH$_2$—C≡CH |
| 547 | 3,4-(OCH$_2$O—) | i-C$_3$H$_7$ | —CH$_2$—(tetrafluorophenyl)—CH$_2$C≡CH |
| 548 | 3-CF$_3$ | i-C$_3$H$_7$ | —CH$_2$—C≡C—CH$_2$—O—phenyl |
| 549 | 3-Cl,4-F | i-C$_3$H$_7$ | —CH$_2$—phenyl—O—(pyridyl) |
| 550 | 4-OCF$_3$ | i-C$_3$H$_7$ | —CH$_2$—(pyridyl)—O—phenyl |

TABLE 2-continued $$R_1-N=C\begin{matrix}R_2\\OR_3\end{matrix}$$

($R_1$ = unsubstituted or substituted phenyl)

| Cmpd. No. | Phenyl Subst. | $R_2$ | $R_3$ |
|---|---|---|---|
| 551 | 3-F,4-Br | i-$C_3H_7$ | —$CH_2$-(pyridinyl)-O-(phenyl)-Cl |
| 552 | 4-$C_2H_5$ | i-$C_3H_7$ | —$CH_2$-(pyridinyl)-O-(phenyl)-Cl |
| 553 | 4-Cl | i-$C_3H_7$ | —$CH_2$-(pyridinyl)-O-(phenyl) |
| 554 | 4-Cl | i-$C_3H_7$ | —$CH_2$-(pyridinyl)-O-(phenyl)-Cl |
| 555 | 3-$CF_3$,4-Cl | i-$C_3H_7$ | —$CH_2$-(pyridinyl)-O-(phenyl) |
| 556 | 3,4-$OCF_2O$ | i-$C_3H_7$ | —$CH_2$-(pyridinyl)-O-(phenyl) |
| 557 | 3-Br | i-$C_3H_7$ | —$CH_2$-(pyridinyl)-O-(phenyl)-Cl |
| 558 | 3-Br,4-F | i-$C_3H_7$ | —$CH_2$-(pyridinyl)-O-(phenyl) |
| 559 | 3,4-F | i-$C_3H_7$ | —$CH_2$-(pyridinyl)-O-(phenyl)-Cl |
| 560 | 4-$CF_3$ | —$C(CH_3)$=$CH_2$ | —$CH_2$-(pyridinyl)-O-(phenyl)-Cl |

INSECTICIDAL EVALUATION TESTS

The compounds in Tables 1 and 2 above were tested for insecticidal activity using the following testing procedures. $LC_{50}$ values, based on the results of these tests and calculated according to dosage-mortality curves, are expressed in Table 3.

Housefly [*Musca domestica*]:

Test compounds were diluted in acetone and aliquots pipetted onto the bottom of aluminum dishes. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies downward. The LC-50 value is expressed below in Table 3 under the heading "HF", in terms of μg of the test compound per 25 female flies.

Black Bean Aphid [*Aphis fabae* (Scop.)]:

Nasturtium plants (Tropaeolum sp.) approximately 5 cm tall, were transplanted into sandy loam soil in small cups and infested with 25-50 black bean aphids of mixed ages. Twenty-four hours later they were sprayed to the point of runoff with 50-50 acetone-water solutions of the test compounds. Treated plants were held in the greenhouse and mortality was recorded after 48 hours. Test concentrations ranged from 0.05% downward. The LC-50 value is expressed below in Table 3 under the heading "BBA" in terms of percent of the test compound in the sprayed solution.

Tobacco Budworm [*Heliothis virescens* (Fabricius)]:

(a) Contact: Test compounds were diluted in a 50-50 acetone-water solution. Cotton (Gossypium sp.) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LC-50 values are expressed below in Table 3 under the heading "TBW-C" in terms of percent of the test compound in the solution.

(b). Eggs: Paper towel patches of 2-day old eggs of the tobacco budworm were dipped in acetone solutions of the test compound and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LC-50 value is expressed below in Table 3 under the heading "TBW-E" in terms of percent of the test compound in the solution.

Cabbage Looper [*Trichoplusia ni* (Hubner)]:

Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 3-5 days later. Test concentrations ranged from 0.1% downward. The LC-50 value is expressed below in Table 3 under the heading "CL" in terms of percent of the test compound in solution.

Beet Armyworm (*Spodoptera exigua*):

Test compounds were diluted in a 50-50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LC-50 values are expressed below in Table 3 under the heading "BAW" in terms of percent of the test compound in solution.

Aster Leafhopper [*Macrosteles fascifrens* (Stal)]

Oat seedlings (Avena sp) were grown in a commercial potting soil in cups. When the plants were approximately 10 cm tall they were thinned to three plants per cup and dipped for 2-3 seconds in 50-50 acetone-water solutions of the test compounds. When the plants had dried, a clear plastic tube was placed over them and the bottom end pressed into the cup. Ten aster leafhopper adults/nymphs were then placed in each tube and the tops of the tubes covered with white organdy cloth. Mortality counts were made after 48 hours. Test concentrations ranged from 0.05% down to that at which 50% mortality occurred. The $LC_{50}$ values are expressed below in Table 3 under the heading "LH" in terms of the percent of the test compound in the solution.

Maize weevil [*Sitophilus zeamais* (Motschulsky)]:

Test compounds were diluted in a 50:50 acetone:water solution. Four corn seeds [*Zea mays* (L.)] which had been immersed in test solutions for 2-3 seconds and allowed to dry were placed in containers together with 10 adult weevils. The containers were covered and kept at a temperature of about 25° C. Mortality was recorded after 48 hours. Test concentrations ranged from 0.01% down to that at which 50% mortality occurred. The LC50 values are expressed below in Table 3 under the heading "MW" in terms of percent of the test compound in solution.

Rice water weevil [*Lissorhoptrus oryzophilus* (Kuschel)]:

Test compounds were diluted in acetone. Droplets (1 ul) of test solutions were applied to the ventral abdomens of ten female adult weevils. The treated weevils were placed in containers with wet cotton balls and rice foliage. The containers were covered and kept at a temperature of about 25° C. Mortality was recorded after 48 hours. Test concentrations ranged from 0.25 μg/ml or 2.5 μg per weevil down to that at which 50% mortality occurred. The LC50 values are expressed below in Table 3 under the heading "RWW" in terms of μg of test compound per weevil.

TABLE 3

| | | | ($LC_{50}$) | | | | | | |
|---|---|---|---|---|---|---|---|---|---|
| Cmpd. No. | HF μg | BBA % | TBW, % C | TBW, % E | BAW % | CL % | LH % | MW % | RWW μg |
| 1 | 4.8 | 0.0003 | 0.06 | 0.05 | 0.009 | 0.005 | >0.05 | >0.01 | — |
| 2 | 4.5 | 0.0003 | 0.0009 | 0.04 | 0.01 | 0.006 | 0.0003 | — | — |
| 3 | 50 | 0.003 | 0.009 | >0.1 | 0.015 | 0.012 | >0.05 | >0.01 | — |
| 4 | 100 | >0.05 | 0.05 | >0.1 | 0.04 | 0.007 | >0.05 | — | — |
| 5 | 21 | 0.001 | 0.008 | 0.05 | 0.025 | 0.005 | >0.05 | >0.01 | — |
| 6 | 17 | 0.001 | — | 0.015 | — | 0.02 | >0.05 | >0.01 | — |
| 7 | 8 | 0.0003 | — | 0.009 | 0.006 | 0.006 | 0.0002 | — | — |
| 8 | 50 | 0.03 | — | >0.1 | — | 0.01 | — | >0.01 | — |
| 9 | 14 | 0.001 | 0.0008 | 0.02 | 0.0005 | 0.001 | 0.0003 | >0.01 | — |
| 10 | >100 | 0.05 | — | >0.1 | — | 0.01 | >0.05 | — | — |
| 11 | 6 | 0.01 | — | >0.1 | — | 0.025 | >0.05 | >0.01 | — |

TABLE 3-continued

| Cmpd. No. | HF μg | BBA % | TBW, % C | TBW, % E | BAW % | CL % | LH % | MW % | RWW μg |
|---|---|---|---|---|---|---|---|---|---|
| 12 | >100 | >0.05 | — | >0.1 | — | 0.008 | — | — | — |
| 13 | >100 | 0.003 | — | >0.1 | — | 0.014 | >0.05 | >0.01 | — |
| 14 | 40 | 0.0003 | — | — | 0.005 | 0.004 | 0.001 | 0.01 | — |
| 15 | >100 | >0.05 | — | >0.1 | — | 0.025 | — | — | — |
| 16 | 20 | 0.0004 | — | 0.04 | — | 0.004 | 0.0005 | — | — |
| 17 | 75 | 0.03 | — | >0.1 | — | 0.03 | >0.05 | >0.01 | — |
| 18 | >100 | 0.003 | — | 0.09 | — | 0.008 | — | — | — |
| 19 | >100 | 0.05 | — | >0.1 | — | <0.1 | — | — | — |
| 20 | 64 | 0.0006 | — | <0.1 | — | 0.0025 | 0.003 | — | — |
| 21 | 7 | >0.1 | — | >0.1 | — | 0.02 | >0.05 | >0.01 | — |
| 22 | 15 | 0.01 | — | 0.08 | — | 0.004 | — | — | — |
| 23 | 5 | 0.001 | — | 0.017 | 0.001 | 0.0005 | — | — | — |
| 24 | 25 | 0.01 | — | 0.1 | — | 0.005 | — | — | — |
| 25 | >100 | >0.1 | — | >0.1 | — | 0.01 | >0.05 | >0.01 | — |
| 26 | >100 | — | — | >0.1 | — | 0.007 | — | — | — |
| 27 | >100 | — | — | >0.1 | — | 0.04 | — | — | — |
| 28 | >100 | — | — | >0.1 | — | 0.009 | — | — | — |
| 29 | 5 | 0.001 | 0.001 | 0.01 | 0.003 | 0.002 | 0.003 | >0.01 | — |
| 30 | >100 | >0.05 | 0.01 | >0.1 | — | 0.003 | >0.05 | >0.01 | — |
| 31 | >100 | 0.05 | 0.01 | >0.1 | 0.08 | 0.05 | >0.05 | >0.01 | — |
| 32 | 37 | 0.003 | 0.006 | 0.1 | 0.03 | 0.003 | >0.05 | >0.01 | — |
| 33 | 17 | 0.003 | 0.0025 | >0.1 | 0.02 | 0.01 | >0.05 | >0.01 | — |
| 34 | >100 | >0.05 | 0.01 | >0.1 | 0.015 | 0.015 | — | — | — |
| 35 | 15 | — | — | 0.03 | — | 0.008 | >0.05 | >0.01 | — |
| 36 | 20 | — | — | >0.1 | — | 0.024 | — | — | — |
| 37 | 21 | — | 0.0005 | 0.014 | — | 0.0004 | 0.002 | 0.009 | — |
| 38 | 33 | — | — | 0.05 | — | 0.006 | — | — | — |
| 39 | >100 | — | — | >0.1 | — | 0.0023 | — | — | — |
| 40 | 36 | — | — | 0.08 | — | 0.0025 | — | — | — |
| 41 | 4.5 | 0.001 | 0.0035 | 0.04 | — | 0.015 | — | — | — |
| 42 | 45 | >0.05 | >0.1 | >0.1 | >0.1 | >0.1 | >0.05 | >0.01 | — |
| 43 | 7 | 0.001 | — | 0.05 | — | 0.018 | >0.05 | >0.01 | — |
| 44 | 3 | 0.0006 | <0.1 | 0.06 | — | — | — | — | — |
| 45 | 30 | 0.03 | 0.01 | 0.08 | 0.1 | 0.03 | >0.05 | — | — |
| 46 | 7 | 0.003 | — | 0.016 | 0.006 | 0.003 | 0.002 | — | — |
| 47 | 10 | 0.001 | 0.002 | 0.06 | 0.002 | 0.002 | 0.0003 | — | — |
| 48 | >100 | >0.05 | — | >0.05 | — | 0.03 | — | — | — |
| 49 | >100 | 0.05 | — | >0.05 | — | 0.007 | >0.05 | — | — |
| 50 | 43 | 0.01 | — | >0.05 | — | 0.02 | >0.05 | >0.01 | — |
| 51 | 25 | 0.01 | 0.0025 | 0.067 | — | 0.001 | 0.001 | — | — |
| 52 | 8 | 0.001 | 0.004 | >0.05 | 0.01 | 0.0025 | 0.001 | — | — |
| 53 | 2 | 0.001 | 0.0025 | 0.02 | 0.003 | 0.0005 | — | — | — |
| 54 | 3.5 | 0.001 | 0.001 | 0.017 | 0.004 | 0.0003 | 0.00015 | — | — |
| 55 | >100 | 0.003 | 0.004 | 0.06 | 0.006 | 0.0017 | 0.0005 | — | >2.5 |
| 56 | 91 | 0.03 | — | >0.05 | — | 0.01 | — | — | — |
| 57 | >100 | 0.03 | — | 0.1 | — | 0.004 | 0.0005 | — | — |
| 58 | 16 | 0.003 | — | 0.06 | — | 0.002 | — | — | — |
| 59 | 25 | — | — | >0.1 | — | 0.02 | — | — | — |
| 60 | 8 | — | 0.0009 | 0.017 | — | 0.001 | 0.002 | 0.0075 | — |
| 61 | 29 | 0.001 | 0.03 | 0.03 | 0.002 | 0.001 | >0.05 | >0.01 | — |
| 62 | 20 | 0.001 | 0.0015 | 0.025 | 0.02 | 0.005 | >0.05 | >0.01 | — |
| 63 | 30 | 0.0003 | 0.001 | 0.05 | 0.005 | 0.005 | 0.0001 | >0.01 | — |
| 64 | 11 | 0.0006 | 0.1 | 0.03 | 0.0025 | 0.0025 | >0.05 | >0.01 | — |
| 65 | >100 | >0.05 | 0.1 | >0.1 | >0.1 | <0.01 | >0.05 | — | — |
| 66 | 9.7 | 0.0003 | — | 0.06 | 0.0065 | <0.0025 | 0.001 | — | >2.5 |
| 67 | 15 | 0.0002 | — | 0.01 | 0.006 | 0.001 | 0.00027 | — | — |
| 68 | 37 | 0.0003 | — | 0.009 | — | 0.006 | 0.0001 | >0.01 | 0.15 |
| 69 | >100 | >0.05 | — | >0.1 | — | 0.09 | >0.05 | — | — |
| 70 | <100 | <0.05 | — | 0.01 | — | <0.1 | >0.05 | — | — |
| 71 | 50 | 0.001 | 0.0008 | 0.065 | 0.0004 | 0.0006 | 0.002 | — | — |
| 72 | >100 | >0.05 | — | >0.1 | — | 0.08 | >0.05 | >0.01 | — |
| 73 | 25 | 0.003 | 0.005 | 0.025 | — | 0.004 | — | — | — |
| 74 | 25 | 0.001 | 0.0025 | 0.025 | — | 0.005 | — | — | — |
| 75 | 5 | 0.0006 | 0.0075 | 0.01 | — | 0.0025 | 0.0008 | — | — |
| 76 | 20 | 0.003 | — | 0.05 | — | 0.002 | — | — | — |
| 77 | 10 | 0.001 | 0.0004 | 0.03 | 0.004 | 0.0005 | 0.0002 | >0.01 | — |
| 78 | >100 | 0.03 | — | >0.1 | — | 0.0025 | — | — | — |
| 79 | 6 | 0.03 | — | 0.05 | — | 0.003 | — | — | — |
| 80 | 4.5 | 0.00025 | 0.00075 | 0.005 | 0.0018 | 0.0003 | 0.0001 | — | — |
| 81 | 4 | 0.001 | 0.0009 | 0.007 | 0.003 | 0.0006 | 0.0003 | 0.005 | >0.5 |
| 82 | 2.5 | 0.00021 | 0.0008 | 0.006 | 0.0025 | 0.00018 | 0.0001 | — | 0.086 |
| 83 | >100 | 0.05 | — | >0.1 | — | 0.007 | >0.05 | — | — |
| 84 | 93 | 0.03 | — | 0.1 | — | 0.006 | — | — | — |
| 85 | 7 | 0.0017 | — | >0.1 | — | 0.004 | 0.003 | >0.01 | >2.5 |
| 86 | 65 | <0.05 | — | >0.1 | — | 0.013 | — | — | — |
| 87 | 5 | 0.001 | — | 0.03 | — | 0.004 | — | — | — |
| 88 | >100 | >0.05 | — | >0.1 | — | 0.018 | — | >0.01 | — |
| 89 | 5 | 0.003 | 0.0005 | 0.04 | 0.009 | 0.00003 | 0.001 | 0.005 | >2.5 |

TABLE 3-continued

| Cmpd. No. | HF μg | BBA % | TBW, % C | TBW, % E | BAW % | CL % | LH % | MW % | RWW μg |
|---|---|---|---|---|---|---|---|---|---|
| 90 | >100 | 0.0003 | — | 0.016 | — | >0.1 | 0.001 | — | — |
| 91 | 37 | 0.001 | — | >0.01 | — | 0.002 | 0.003 | — | — |
| 92 | >100 | >0.05 | — | >0.1 | — | 0.015 | >0.05 | — | — |
| 93 | 64 | 0.003 | — | >0.1 | — | 0.005 | — | — | — |
| 94 | 44 | 0.001 | — | 0.075 | — | 0.0045 | — | — | — |
| 95 | 10 | 0.001 | 0.004 | 0.025 | — | 0.0025 | — | — | — |
| 96 | 35 | 0.002 | 0.0025 | 0.025 | — | 0.003 | — | — | — |
| 97 | 10 | 0.001 | 0.004 | 0.04 | 0.01 | 0.002 | — | — | — |
| 98 | >100 | >0.05 | — | 0.1 | — | 0.016 | >0.05 | — | — |
| 99 | >100 | >0.05 | — | >0.1 | — | 0.016 | — | — | — |
| 100 | 100 | >0.05 | — | >0.1 | — | 0.05 | — | — | — |
| 101 | 81 | 0.002 | — | >0.1 | — | 0.0045 | 0.0008 | — | — |
| 102 | >100 | 0.05 | — | >0.1 | — | 0.075 | >0.05 | — | — |
| 103 | >100 | 0.001 | — | >0.1 | — | 0.015 | — | — | — |
| 104 | >100 | 0.003 | — | >0.1 | — | 0.004 | — | — | — |
| 105 | >100 | 0.05 | — | >0.1 | — | 0.018 | — | — | — |
| 106 | >100 | 0.01 | — | >0.1 | — | 0.014 | — | — | — |
| 107 | >100 | 0.01 | — | >0.1 | — | 0.007 | — | — | — |
| 108 | 44 | 0.01 | — | >0.1 | — | 0.002 | >0.01 | — | — |
| 109 | >100 | >0.05 | — | >0.1 | — | 0.002 | — | — | — |
| 110 | 26 | — | — | 0.04 | — | 0.007 | — | — | — |
| 111 | >100 | 0.003 | — | >0.1 | — | 0.1 | — | — | — |
| 112 | >100 | 0.05 | — | >0.1 | — | 0.025 | >0.05 | >0.01 | — |
| 113 | 15 | — | — | 0.1 | — | 0.005 | — | — | >2.5 |
| 114 | 92 | — | — | — | — | <0.1 | — | — | — |
| 115 | 10 | — | — | 0.075 | — | 0.0012 | — | — | — |
| 116 | 15 | — | — | 0.05 | — | 0.00025 | — | >0.01 | — |
| 117 | 55 | >0.05 | — | >0.1 | — | 0.006 | 0.0003 | >0.01 | — |
| 118 | 18 | — | — | >0.1 | — | 0.0013 | — | — | — |
| 119 | 27 | >0.05 | — | 0.048 | — | 0.0007 | 0.0008 | >0.01 | — |
| 120 | 14 | 0.0006 | 0.0025 | 0.04 | — | 0.00015 | 0.0003 | >0.01 | — |
| 121 | >100 | — | — | >0.1 | — | 0.1 | — | — | — |
| 122 | 37 | >0.05 | — | 0.05 | 0.01 | 0.0007 | >0.05 | >0.01 | — |
| 123 | >100 | — | — | >0.1 | — | 0.012 | — | — | — |
| 124 | 17 | >0.05 | — | >0.1 | — | 0.01 | >0.05 | >0.01 | — |
| 125 | 12 | 0.05 | — | 0.025 | — | 0.0007 | >0.05 | >0.01 | >2.5 |
| 126 | >100 | — | — | >0.1 | — | 0.08 | — | — | — |
| 127 | 58 | 0.001 | — | 0.04 | — | 0.01 | — | — | — |
| 128 | 4.5 | 0.001 | — | 0.037 | — | 0.005 | 0.003 | >0.01 | — |
| 129 | >100 | 0.03 | — | >0.1 | — | 0.005 | 0.01 | — | — |
| 130 | >100 | 0.05 | — | >0.1 | — | 0.005 | — | — | — |
| 131 | 17 | 0.003 | — | >0.1 | — | 0.0045 | 0.005 | — | — |
| 132 | 65 | 0.0025 | — | >0.1 | — | 0.025 | >0.05 | >0.01 | — |
| 133 | 66 | 0.003 | — | 0.1 | — | 0.005 | — | — | — |
| 134 | >100 | >0.05 | — | >0.1 | — | 0.015 | — | — | — |
| 135 | >100 | >0.05 | — | >0.1 | — | 0.004 | >0.05 | — | — |
| 136 | 9 | 0.002 | — | 0.08 | — | 0.004 | — | — | — |
| 137 | 18 | 0.03 | — | 0.04 | — | 0.003 | 0.008 | — | — |
| 138 | 19 | 0.003 | 0.015 | 0.08 | — | 0.005 | >0.05 | >0.01 | — |
| 139 | 4.2 | 0.001 | 0.005 | 0.05 | 0.007 | 0.015 | — | — | — |
| 140 | >100 | 0.05 | >0.1 | >0.1 | — | <0.1 | — | — | — |
| 141 | 35 | 0.006 | — | >0.1 | — | <0.1 | — | — | — |
| 142 | 15 | 0.001 | — | 0.1 | — | 0.005 | >0.05 | >0.01 | — |
| 143 | 10 | 0.002 | — | <0.1 | — | 0.002 | 0.006 | >0.01 | — |
| 144 | 100 | 0.003 | 0.006 | 0.05 | >0.01 | 0.002 | 0.0006 | >0.01 | — |
| 145 | >100 | >0.05 | 0.05 | >0.1 | — | 0.05 | >0.05 | — | — |
| 146 | 40 | 0.05 | 0.025 | >0.1 | — | 0.017 | — | — | — |
| 147 | 10 | 0.03 | 0.0075 | >0.1 | — | 0.01 | — | — | — |
| 148 | 18 | 0.0003 | — | 0.025 | — | 0.0025 | — | — | — |
| 149 | 17 | 0.001 | — | 0.05 | — | 0.007 | — | — | — |
| 150 | 89 | 0.03 | — | >0.1 | — | 0.01 | — | — | — |
| 151 | 38 | 0.006 | — | >0.1 | — | 0.009 | >0.05 | >0.01 | — |
| 152 | >100 | 0.01 | — | >0.1 | — | 0.009 | — | — | — |
| 153 | >100 | 0.003 | — | 0.1 | — | 0.004 | 0.0005 | >0.01 | — |
| 154 | 25 | 0.002 | — | 0.1 | — | 0.004 | >0.05 | — | — |
| 155 | 9 | 0.001 | — | 0.06 | — | 0.004 | >0.05 | >0.01 | — |
| 156 | 10 | 0.001 | — | 0.05 | — | 0.004 | >0.05 | >0.01 | — |
| 157 | 25 | 0.002 | — | >0.1 | — | 0.009 | — | — | — |
| 158 | 9 | 0.0015 | — | 0.1 | — | 0.003 | — | — | — |
| 159 | 25 | 0.001 | — | 0.08 | — | 0.001 | 0.0025 | — | — |
| 160 | 7 | 0.003 | — | 0.09 | — | 0.005 | 0.05 | >0.01 | — |
| 161 | 15 | 0.0006 | — | 0.07 | — | 0.0014 | 0.002 | — | — |
| 162 | >100 | >0.05 | — | >0.1 | — | 0.035 | >0.05 | — | — |
| 163 | >100 | >0.05 | — | >0.1 | — | 0.004 | — | >0.01 | — |
| 164 | >100 | >0.05 | — | >0.1 | — | 0.005 | — | — | — |
| 165 | >100 | >0.05 | — | >0.1 | — | 0.007 | — | — | — |
| 166 | 22 | 0.001 | — | >0.1 | — | 0.009 | — | — | — |
| 167 | >100 | >0.05 | — | >0.1 | — | 0.02 | — | — | — |

TABLE 3-continued

| Cmpd. No. | HF μg | BBA % | TBW, % C | TBW, % E | BAW % | CL % | LH % | MW % | RWW μg |
|---|---|---|---|---|---|---|---|---|---|
| 168 | >100 | >0.05 | — | >0.1 | — | 0.1 | — | — | — |
| 169 | 10 | 0.003 | — | >0.1 | — | 0.009 | — | — | — |
| 170 | 37 | — | — | >0.1 | — | 0.1 | — | — | — |
| 171 | 80 | — | — | >0.1 | — | 0.01 | — | — | — |
| 172 | 5 | >0.05 | — | 0.04 | — | 0.002 | >0.05 | >0.01 | — |
| 173 | 18 | >0.05 | >0.1 | >0.1 | >0.1 | 0.02 | — | — | — |
| 174 | 17 | 0.05 | — | >0.1 | 0.1 | 0.03 | — | — | — |
| 175 | >100 | >0.05 | — | >0.1 | — | 0.018 | — | — | — |
| 176 | 1.8 | 0.0006 | 0.002 | 0.05 | 0.0035 | 0.0005 | >0.05 | 0.009 | — |
| 177 | 13 | 0.01 | — | >0.1 | — | 0.002 | >0.05 | 0.01 | — |
| 178 | 6 | 0.05 | — | >0.1 | — | 0.004 | >0.05 | >0.01 | — |
| 179 | 13 | 0.003 | — | >0.1 | — | 0.004 | 0.005 | >0.01 | — |
| 180 | 2 | 0.0003 | 0.003 | 0.03 | 0.005 | 0.0004 | 0.0015 | 0.008 | >2.5 |
| 181 | 25 | — | 0.001 | 0.01 | 0.001 | 0.0005 | — | 0.005 | >2.5 |
| 182 | 28 | — | — | 0.04 | — | 0.0006 | — | — | — |
| 183 | 10 | — | — | 0.075 | — | 0.00075 | — | — | — |
| 184 | 61 | — | — | >0.1 | — | 0.024 | — | — | — |
| 185 | 13 | — | — | 0.075 | — | 0.0006 | — | — | — |
| 186 | >100 | >0.05 | — | >0.1 | — | 0.008 | >0.05 | >0.01 | — |
| 187 | 15 | 0.001 | — | >0.1 | — | 0.0025 | 0.0025 | — | — |
| 188 | 12 | — | — | >0.1 | — | 0.002 | >0.05 | — | — |
| 189 | 17 | — | — | 0.07 | — | 0.00027 | 0.002 | >0.01 | — |
| 190 | 7.5 | — | — | 0.023 | — | 0.0004 | — | — | — |
| 191 | 29 | 0.001 | — | 0.04 | — | 0.00023 | >0.05 | 0.004 | >2.5 |
| 192 | 25 | — | — | 0.07 | — | 0.0012 | — | — | — |
| 193 | 100 | — | — | >0.1 | — | 0.00075 | 0.001 | >0.01 | — |
| 194 | 10 | 0.001 | 0.0017 | 0.04 | — | 0.0005 | 0.0005 | >0.01 | — |
| 195 | >100 | — | — | >0.1 | — | 0.002 | — | — | — |
| 196 | 17 | — | 0.001 | >0.1 | — | 0.0006 | >0.05 | >0.01 | — |
| 197 | >100 | — | — | 0.05 | — | 0.0004 | — | — | — |
| 198 | 52 | — | — | >0.1 | — | 0.0005 | 0.05 | 0.003 | >2.5 |
| 199 | 8 | — | 0.003 | >0.1 | — | 0.0006 | — | >0.01 | — |
| 200 | 7.5 | — | — | 0.1 | — | 0.00075 | — | — | — |
| 201 | 15 | — | — | >0.1 | — | 0.004 | — | — | — |
| 202 | 18 | 0.003 | 0.0007 | >0.1 | — | 0.00024 | 0.0003 | >0.01 | — |
| 203 | 43 | 0.006 | — | 0.06 | — | 0.0025 | — | >0.01 | — |
| 204 | >100 | — | 0.004 | >0.1 | — | 0.0023 | — | >0.01 | — |
| 205 | 50 | 0.03 | — | >0.1 | — | 0.004 | — | — | — |
| 206 | 50 | 0.03 | — | >0.1 | — | 0.0017 | — | — | — |
| 207 | >100 | — | — | >0.1 | — | 0.008 | — | — | — |
| 208 | 27 | 0.05 | — | >0.1 | — | 0.0035 | — | — | — |
| 209 | 17 | 0.01 | 0.005 | 0.1 | — | 0.0007 | 0.001 | >0.01 | — |
| 210 | 35 | 0.01 | 0.0015 | 0.045 | — | 0.00028 | — | >0.01 | — |
| 211 | 61 | 0.01 | — | >0.1 | — | 0.0017 | — | — | — |
| 212 | 20 | 0.05 | — | 0.045 | — | 0.0005 | — | — | — |
| 213 | >100 | 0.01 | — | >0.1 | — | 0.00075 | — | — | — |
| 214 | 19 | 0.01 | — | 0.04 | — | 0.0003 | — | — | — |
| 215 | 75 | 0.05 | — | >0.1 | — | 0.00075 | — | — | — |
| 216 | 2 | 0.00025 | 0.00018 | 0.005 | 0.0007 | 0.000007 | 0.00025 | 0.0017 | 0.067 |
| 217 | 8 | 0.001 | — | 0.015 | — | 0.00006 | >0.05 | 0.0084 | — |
| 218 | 25 | 0.003 | — | 0.025 | — | 0.0003 | — | — | — |
| 219 | 50 | 0.003 | 0.004 | 0.027 | — | 0.00025 | — | >0.01 | — |
| 220 | 85 | 0.03 | — | >0.1 | — | 0.007 | — | — | — |
| 221 | 62 | 0.01 | — | >0.1 | — | 0.0027 | — | — | — |
| 222 | 32 | 0.01 | — | >0.1 | — | 0.0015 | — | — | — |
| 223 | 43 | 0.003 | — | >0.1 | — | 0.008 | — | — | — |
| 224 | >100 | 0.05 | — | >0.1 | — | 0.001 | — | — | — |
| 225 | >100 | 0.006 | — | >0.1 | — | 0.0025 | >0.05 | — | — |
| 226 | 16 | 0.01 | 0.001 | 0.1 | — | 0.0005 | 0.002 | 0.009 | — |
| 227 | 10 | 0.01 | — | 0.1 | — | 0.0015 | — | — | — |
| 228 | >100 | 0.01 | — | >0.1 | — | 0.0025 | >0.05 | — | — |
| 229 | 20 | 0.006 | — | >0.1 | — | 0.0005 | — | — | — |
| 230 | 36 | 0.01 | — | 0.1 | — | 0.0004 | — | 0.038 | >2.5 |
| 231 | >100 | 0.01 | — | >0.1 | — | 0.003 | — | — | — |
| 232 | >100 | >0.05 | — | >0.1 | — | 0.004 | — | — | — |
| 233 | 10 | 0.01 | — | 0.09 | — | 0.0017 | — | — | — |
| 234 | 38 | 0.003 | 0.0013 | 0.09 | — | 0.00045 | 0.003 | >0.01 | — |
| 235 | >100 | 0.01 | — | >0.1 | — | 0.004 | — | — | — |
| 236 | 7 | 0.003 | — | 0.06 | — | 0.0018 | — | — | — |
| 237 | 50 | 0.01 | — | 0.075 | — | 0.0006 | — | — | — |
| 238 | 25 | 0.003 | 0.0004 | 0.05 | — | 0.0002 | >0.05 | >0.01 | — |
| 239 | 14 | 0.001 | 0.0005 | 0.025 | 0.005 | 0.00015 | 0.002 | 0.006 | >2.5 |
| 240 | 14 | 0.001 | — | 0.04 | — | 0.0003 | >0.05 | >0.01 | — |
| 241 | >100 | <0.05 | — | >0.1 | — | 0.0004 | — | — | — |
| 242 | <100 | <0.05 | — | >0.1 | — | 0.00025 | >0.05 | — | — |
| 243 | 9 | 0.01 | — | >0.1 | — | 0.005 | — | — | — |
| 244 | 14 | 0.0006 | 0.00025 | >0.1 | 0.002 | 0.00004 | — | 0.0025 | 0.09 |
| 245 | 20 | 0.0003 | 0.0015 | 0.016 | 0.001 | 0.0035 | — | 0.006 | >2.5 |

TABLE 3-continued

| Cmpd. No. | HF μg | BBA % | TBW, % C | TBW, % E | BAW % | CL % | LH % | MW % | RWW μg |
|---|---|---|---|---|---|---|---|---|---|
| 246 | 60 | >0.05 | — | >0.1 | — | 0.004 | — | — | — |
| 247 | >100 | >0.05 | — | >0.1 | — | 0.009 | — | — | — |
| 248 | 40 | >0.05 | — | >0.1 | — | 0.02 | — | — | — |
| 249 | 36 | 0.0003 | — | 0.035 | — | 0.0025 | — | — | — |
| 250 | 38 | 0.0006 | — | 0.038 | — | 0.004 | — | — | — |
| 251 | 25 | 0.001 | — | 0.06 | — | 0.0005 | — | — | — |
| 252 | 34 | 0.002 | — | 0.04 | — | 0.0035 | — | — | — |
| 253 | 10 | 0.002 | 0.0005 | >0.1 | — | 0.000013 | 0.003 | >0.01 | — |
| 254 | 6 | 0.001 | — | 0.026 | — | 0.001 | — | — | >2.5 |
| 255 | 16 | 0.003 | — | 0.075 | — | 0.000017 | 0.0005 | >0.01 | — |
| 256 | >100 | 0.03 | — | 0.1 | — | 0.007 | >0.05 | >0.01 | — |
| 257 | >100 | 0.05 | — | >0.1 | — | 0.008 | >0.05 | — | — |
| 258 | >100 | 0.01 | — | >0.1 | — | 0.003 | >0.05 | — | — |
| 259 | 15 | 0.006 | — | 0.05 | — | 0.0003 | >0.05 | >0.01 | — |
| 260 | 22 | 0.006 | — | >0.1 | — | 0.00075 | — | — | — |
| 261 | 24 | 0.002 | — | 0.05 | — | 0.001 | — | — | — |
| 262 | 26 | 0.03 | — | >0.1 | — | 0.0004 | — | 0.005 | >2.5 |
| 263 | >100 | >0.05 | — | >0.1 | — | 0.05 | — | — | — |
| 264 | >100 | >0.05 | — | >0.1 | — | 0.03 | — | — | — |
| 265 | 10 | >0.05 | — | 0.07 | — | 0.00025 | — | — | — |
| 266 | 10 | >0.05 | 0.0007 | 0.06 | — | 0.00016 | — | — | — |
| 267 | 8.4 | 0.0003 | 0.0003 | 0.015 | 0.0012 | 0.00008 | 0.002 | 0.0027 | 0.11 |
| 268 | 4 | >0.05 | 0.0005 | 0.023 | 0.001 | 0.000025 | 0.0005 | >0.01 | — |
| 269 | 25 | >0.05 | 0.001 | 0.04 | 0.0024 | 0.0003 | 0.003 | >0.01 | >2.5 |
| 270 | 12 | >0.05 | >0.0015 | >0.01 | 0.005 | 0.00025 | 0.003 | >0.01 | — |
| 271 | 27 | >0.05 | — | 0.1 | — | 0.0004 | >0.05 | >0.01 | — |
| 272 | >100 | >0.05 | — | >0.1 | — | 0.0024 | — | — | — |
| 273 | 7 | 0.0003 | 0.00025 | 0.015 | 0.0017 | 0.000018 | 0.0003 | 0.004 | >2.5 |
| 274 | >100 | >0.05 | — | >0.1 | — | 0.1 | — | — | — |
| 275 | 21 | — | — | 0.045 | — | 0.00012 | — | — | — |
| 276 | 39 | — | — | 0.1 | — | 0.002 | — | — | — |
| 277 | 4 | 0.0008 | 0.0005 | 0.013 | 0.005 | 0.00001 | 0.0003 | >0.01 | 0.065 |
| 278 | 3 | 0.0005 | 0.00026 | 0.008 | 0.0012 | 0.00002 | 0.0003 | 0.0063 | 0.085 |
| 279 | 4 | 0.0005 | 0.007 | 0.016 | 0.0025 | 0.00008 | 0.0003 | >0.01 | — |
| 280 | >100 | — | — | >0.1 | — | 0.024 | — | — | — |
| 281 | 5 | 0.0003 | 0.00025 | 0.006 | 0.0027 | 0.00002 | — | 0.005 | >2.5 |
| 282 | 16 | — | 0.0007 | 0.02 | 0.0025 | 0.00007 | — | 0.008 | — |
| 283 | 23 | — | 0.0009 | 0.016 | 0.0013 | 0.00009 | — | >0.01 | — |
| 284 | 39 | 0.0003 | 0.0002 | — | 0.0025 | 0.00005 | 0.0003 | 0.0075 | — |
| 285 | 36 | — | 0.00017 | 0.005 | 0.0006 | 0.000075 | — | 0.005 | 0.13 |
| 286 | 34 | 0.0003 | 0.00017 | 0.005 | 0.0004 | 0.000024 | 0.0006 | 0.0039 | 0.09 |
| 287 | >100 | — | — | >0.1 | — | 0.0025 | — | — | — |
| 288 | >100 | — | — | >0.1 | — | 0.0015 | — | — | — |
| 289 | 10 | 0.0003 | — | 0.006 | — | 0.00007 | 0.0003 | >0.01 | 0.082 |
| 290 | >100 | — | — | >0.1 | — | 0.017 | — | — | — |
| 291 | >100 | — | — | >0.1 | — | 0.004 | — | — | — |
| 292 | 41 | — | — | 0.05 | — | 0.00075 | — | >0.01 | — |
| 293 | 19 | >0.05 | — | >0.1 | — | 0.0045 | >0.05 | >0.01 | — |
| 294 | >100 | — | — | >0.1 | — | 0.017 | — | >0.01 | — |
| 295 | 7.8 | 0.0003 | 0.0005 | 0.01 | — | 0.00004 | 0.0001 | 0.0053 | >2.5 |
| 296 | 38 | 0.0003 | 0.00045 | 0.025 | — | 0.00025 | 0.0003 | — | 0.14 |
| 297 | 23 | — | 0.00075 | 0.025 | — | 0.00027 | 0.0001 | 0.0071 | — |
| 298 | 13 | — | 0.0008 | 0.015 | — | 0.0001 | 0.0001 | 0.008 | >2.5 |
| 299 | 8 | — | — | 0.017 | — | 0.0005 | — | >0.01 | — |
| 300 | 14 | 0.0003 | 0.001 | 0.024 | — | 0.0003 | 0.00002 | 0.01 | 0.075 |
| 301 | >100 | — | — | >0.1 | — | 0.008 | — | >0.01 | — |
| 302 | 15 | — | — | >0.1 | — | 0.003 | — | >0.01 | — |
| 303 | >100 | — | — | >0.1 | — | 0.0015 | 0.0005 | — | — |
| 304 | >100 | — | — | >0.1 | — | 0.0024 | — | >0.01 | — |
| 305 | >100 | — | — | >0.1 | — | 0.048 | — | — | — |
| 306 | >100 | — | — | 0.1 | — | 0.005 | — | >0.01 | — |
| 307 | >100 | — | — | 0.08 | — | 0.002 | — | >0.01 | — |
| 308 | >100 | — | — | >0.1 | — | 0.009 | — | — | — |
| 309 | >100 | — | — | 0.07 | — | 0.00017 | — | — | — |
| 310 | 4.5 | 0.0006 | — | 0.015 | — | 0.00006 | — | — | >2.5 |
| 311 | 22 | — | — | 0.1 | — | 0.0017 | — | — | — |
| 312 | >100 | — | — | >0.1 | — | 0.006 | — | — | — |
| 313 | >100 | — | — | 0.013 | — | 0.00025 | — | — | — |
| 314 | 21 | — | — | 0.012 | — | 0.00005 | — | — | 0.11 |
| 315 | >100 | >0.05 | — | >0.1 | — | 0.002 | >0.05 | >0.01 | — |
| 316 | 100 | >0.05 | — | >0.1 | — | 0.0015 | >0.05 | >0.01 | — |
| 317 | >100 | — | — | 0.03 | — | 0.0045 | — | — | — |
| 318 | 19 | — | — | >0.1 | — | 0.0007 | — | — | — |
| 319 | 44 | — | — | >0.1 | — | 0.0007 | — | — | — |
| 320 | >100 | — | — | >0.1 | — | 0.0075 | — | — | — |
| 321 | >100 | — | — | >0.1 | — | 0.05 | — | — | — |
| 322 | >100 | — | — | >0.1 | — | 0.007 | — | — | — |
| 323 | >100 | >0.05 | 0.00065 | 0.045 | 0.0025 | 0.0006 | 0.05 | 0.0075 | 0.16 |

TABLE 3-continued

| Cmpd. No. | HF μg | BBA % | TBW. % (LC$_{50}$) C | E | BAW % | CL % | LH % | MW % | RWW μg |
|---|---|---|---|---|---|---|---|---|---|
| 324 | >100 | 0.0003 | 0.0004 | 0.025 | 0.0024 | 0.00014 | — | — | 0.06 |
| 325 | 5 | 0.0001 | 0.0006 | 0.037 | 0.0025 | 0.00012 | — | — | >2.5 |
| 326 | 25 | >0.05 | 0.0005 | 0.03 | 0.004 | 0.00015 | — | — | — |
| 327 | >100 | >0.05 | — | >0.1 | — | 0.005 | — | — | — |
| 328 | >100 | >0.05 | — | >0.1 | — | 0.03 | — | — | — |
| 329 | 7 | >0.05 | — | >0.1 | — | 0.033 | — | — | — |
| 330 | 5 | 0.0001 | 0.00035 | 0.037 | — | 0.00012 | <0.05 | 0.001 | 0.06 |
| 331 | 20 | >0.05 | 0.0004 | 0.04 | 0.002 | 0.0002 | — | — | >2.5 |
| 332 | 7 | >0.05 | 0.00075 | 0.015 | 0.0012 | 0.00045 | — | — | — |
| 333 | 15 | 0.001 | 0.00075 | 0.025 | >0.1 | 0.00024 | — | >0.01 | — |
| 334 | 9 | 0.0006 | — | 0.013 | — | 0.0007 | — | >0.01 | — |
| 335 | 34 | 0.0008 | 0.00025 | 0.05 | >0.1 | 0.00027 | — | >0.01 | — |
| 336 | 3.6 | 0.0003 | 0.0005 | 0.02 | 0.001 | 0.00017 | — | 0.0091 | >2.5 |
| 337 | 21 | 0.0003 | 0.0005 | 0.008 | 0.0005 | 0.0007 | — | 0.0053 | 0.067 |
| 338 | 26 | 0.0003 | 0.00037 | 0.01 | — | 0.000065 | — | 0.0053 | 0.044 |
| 339 | >100 | 0.03 | — | >0.1 | — | 0.017 | — | >0.01 | — |
| 340 | 34 | 0.001 | — | 0.04 | — | 0.00037 | — | 0.0069 | — |
| 341 | 4 | 0.0005 | — | 0.023 | — | 0.0005 | — | >0.01 | — |
| 342 | 4.1 | 0.0006 | — | 0.04 | — | 0.0008 | — | >0.01 | — |
| 343 | 40 | 0.002 | 0.00025 | >0.1 | >0.1 | 0.00027 | — | >0.01 | — |
| 344 | >100 | 0.008 | — | >0.1 | — | 0.024 | — | >0.01 | — |
| 345 | >100 | 0.006 | — | >0.1 | — | 0.018 | — | >0.01 | — |
| 346 | 7.2 | 0.0008 | 0.0002 | >0.1 | >0.1 | >0.1 | 0.05 | >0.01 | — |
| 347 | 30 | 0.0002 | 0.0001 | >0.1 | 0.00075 | 0.000075 | 0.0002 | >0.01 | — |
| 348 | 8 | 0.001 | 0.00075 | >0.1 | >0.1 | 0.0002 | 0.05 | >0.01 | — |
| 349 | 4.9 | >0.05 | 0.0004 | >0.1 | >0.1 | 0.00007 | — | >0.01 | >2.5 |
| 350 | >100 | >0.05 | — | >0.1 | — | 0.0045 | >0.05 | >0.01 | — |
| 351 | 26 | 0.001 | — | >0.1 | — | 0.0007 | >0.05 | >0.01 | — |
| 352 | 4.6 | 0.0003 | 0.0004 | >0.1 | >0.1 | 0.000065 | 0.0004 | 0.0075 | >2.5 |
| 353 | <100 | 0.001 | — | >0.1 | — | >0.1 | >0.05 | >0.01 | — |
| 354 | <100 | 0.001 | — | 0.018 | — | >0.1 | <0.05 | 0.0068 | — |
| 355 | <100 | 0.0006 | — | >0.1 | — | >0.1 | <0.05 | >0.01 | — |
| 356 | <100 | 0.001 | — | 0.025 | — | >0.1 | <0.05 | >0.01 | — |
| 357 | <100 | 0.0003 | — | >0.1 | — | >0.1 | <0.05 | 0.01 | — |
| 358 | <100 | 0.0003 | — | >0.1 | — | >0.1 | <0.05 | >0.01 | — |
| 359 | <100 | 0.0006 | — | 0.023 | — | >0.1 | 0.05 | >0.01 | — |
| 360 | <100 | 0.0006 | — | >0.1 | — | 0.006 | <0.05 | >0.01 | — |
| 361 | <100 | 0.0003 | — | 0.04 | — | 0.001 | <0.05 | >0.01 | — |
| 362 | <100 | 0.005 | — | >0.1 | — | >0.1 | >0.05 | >0.01 | — |
| 363 | <100 | 0.005 | — | >0.1 | — | >0.1 | >0.05 | >0.01 | — |
| 364 | <100 | 0.001 | — | 0.025 | — | 0.00045 | <0.05 | >0.01 | — |
| 365 | >100 | 0.003 | — | 0.038 | — | 0.00025 | <0.05 | >0.01 | — |
| 366 | <100 | 0.0006 | — | 0.012 | — | 0.0007 | 0.05 | >0.01 | — |
| 367 | >100 | >0.05 | — | >0.1 | — | <0.1 | >0.05 | >0.01 | — |
| 368 | <100 | 0.001 | — | 0.04 | — | 0.002 | — | >0.01 | — |
| 369 | >100 | 0.0003 | — | >0.1 | — | 0.0016 | — | >0.01 | >2.5 |
| 370 | <100 | 0.0002 | — | 0.02 | — | 0.00034 | — | >0.01 | >2.5 |
| 371 | <100 | 0.0004 | — | >0.1 | — | 0.0022 | — | >0.01 | — |
| 372 | >100 | 0.001 | — | >0.1 | — | >0.1 | — | >0.01 | — |
| 373 | <100 | 0.001 | — | >0.1 | — | >0.1 | — | >0.01 | — |
| 374 | <100 | 0.0008 | — | 0.02 | — | 0.00058 | — | >0.01 | — |
| 375 | 7.9 | 0.0006 | — | 0.04 | — | >0.1 | — | >0.01 | >2.5 |
| 376 | 17 | 0.0003 | — | 0.02 | — | 0.00037 | — | 0.0061 | 0.1 |
| 377 | <100 | 0.001 | — | >0.1 | — | 0.00062 | — | >0.01 | >2.5 |
| 378 | <100 | 0.0008 | — | 0.02 | — | 0.00034 | — | >0.01 | >2.5 |
| 379 | <100 | 0.0006 | — | 0.02 | — | 0.00075 | — | >0.01 | — |
| 380 | >100 | 0.004 | — | >0.1 | — | >0.1 | — | >0.01 | >2.5 |
| 381 | <100 | 0.002 | — | 0.018 | — | 0.00092 | — | >0.01 | >2.5 |
| 382 | <100 | 0.0003 | — | 0.027 | — | 0.00029 | — | >0.01 | >2.5 |
| 383 | <100 | 0.0006 | — | 0.038 | — | 0.00029 | — | >0.01 | — |
| 384 | <100 | 0.0008 | — | 0.025 | — | >0.1 | — | >0.01 | — |
| 385 | <100 | >0.05 | — | >0.1 | — | >0.1 | — | >0.01 | — |
| 386 | <100 | 0.002 | — | >0.1 | — | 0.0012 | — | >0.01 | — |
| 387 | <100 | 0.0006 | — | 0.05 | — | 0.0012 | — | >0.01 | >2.5 |
| 388 | <100 | 0.0006 | — | >0.1 | — | 0.0012 | — | >0.01 | — |
| 389 | <100 | 0.003 | — | >0.1 | — | 0.00069 | — | >0.01 | — |
| 390 | <100 | 0.0006 | — | 0.045 | — | 0.0021 | — | >0.01 | — |
| 391 | <100 | 0.0006 | — | 0.035 | — | 0.00029 | — | >0.01 | >2.5 |
| 392 | <100 | 0.001 | — | 0.039 | — | 0.00034 | — | >0.01 | — |
| 393 | <100 | >0.05 | — | >0.1 | — | 0.00037 | — | >0.01 | — |
| 394 | <100 | 0.002 | — | 0.05 | — | 0.00025 | — | >0.01 | — |
| 395 | 8.6 | 0.0001 | — | 0.018 | — | <0.1 | — | 0.004 | — |
| 396 | <100 | 0.0002 | — | <0.1 | — | 0.0017 | — | >0.01 | — |
| 397 | <100 | 0.002 | — | <0.1 | — | 0.0019 | — | >0.01 | — |
| 398 | <100 | 0.002 | — | <0.1 | — | <0.1 | — | >0.01 | — |
| 399 | <100 | 0.0003 | — | 0.025 | — | 0.0012 | — | >0.01 | — |
| 400 | <100 | 0.0003 | — | 0.025 | — | 0.0007 | — | >0.01 | — |
| 401 | <100 | 0.0006 | — | 0.04 | — | 0.0017 | — | >0.01 | — |

TABLE 3-continued

| Cmpd. No. | HF μg | BBA % | TBW, % C | TBW, % E | BAW % | CL % | LH % | MW % | RWW μg |
|---|---|---|---|---|---|---|---|---|---|
| 402 | <100 | 0.0006 | — | >0.1 | — | >0.1 | — | >0.01 | — |
| 403 | <100 | 0.001 | — | >0.1 | — | >0.1 | — | >0.01 | — |
| 404 | <100 | 0.002 | — | 0.025 | — | >0.1 | — | >0.01 | — |
| 405 | <100 | 0.0025 | — | >0.1 | — | >0.1 | — | >0.01 | — |
| 406 | <100 | 0.001 | — | <0.1 | — | >0.1 | — | >0.01 | — |
| 407 | >100 | 0.0007 | — | 0.05 | — | >0.1 | — | >0.01 | — |
| 408 | <100 | 0.0005 | — | 0.02 | — | 0.0015 | — | >0.01 | — |
| 409 | <100 | 0.0005 | — | 0.025 | — | 0.0017 | — | >0.01 | — |
| 410 | <100 | 0.0025 | — | >0.1 | — | >0.1 | — | >0.01 | — |
| 411 | <100 | >0.05 | — | >0.1 | — | >0.1 | — | >0.01 | — |
| 412 | <100 | 0.0032 | — | >0.1 | — | >0.1 | — | >0.01 | — |
| 413 | <100 | >0.05 | — | 0.04 | — | 0.0007 | — | >0.01 | — |
| 414 | <100 | >0.05 | — | >0.1 | — | 0.0024 | — | >0.01 | — |
| 415 | <100 | 0.0007 | — | 0.035 | — | 0.00075 | — | >0.01 | — |
| 416 | <100 | 0.0035 | — | 0.018 | — | 0.00027 | — | >0.01 | — |
| 417 | <100 | 0.004 | — | 0.04 | — | 0.0008 | — | >0.01 | — |
| *418 | >100 | >0.05 | — | >0.1 | — | >0.1 | — | >0.01 | — |
| *419 | >100 | >0.05 | — | >0.1 | — | >0.1 | — | >0.01 | — |
| 420 | <100 | 0.004 | — | 0.05 | — | 0.00075 | — | >0.01 | — |
| 421 | >100 | >0.05 | — | <0.1 | — | 0.002 | — | >0.01 | — |
| 422 | <100 | >0.05 | — | 0.05 | — | 0.00075 | — | >0.01 | — |
| 423 | >100 | >0.05 | — | >0.1 | — | 0.002 | — | >0.01 | — |
| 424 | >100 | 0.002 | — | 0.035 | — | 0.00038 | — | >0.01 | — |
| 425 | >100 | 0.0035 | — | >0.1 | — | 0.00075 | — | >0.01 | — |
| 426 | >100 | 0.0012 | — | >0.1 | — | 0.002 | — | >0.01 | — |
| 427 | >100 | 0.05 | — | >0.1 | — | <0.1 | — | >0.01 | — |
| 428 | >100 | 0.003 | — | >0.1 | — | 0.0017 | — | >0.01 | — |
| 429 | >100 | 0.005 | — | <0.1 | — | 0.0017 | — | >0.01 | — |
| 430 | <100 | 0.0006 | — | 0.032 | — | 0.001 | — | 0.004 | — |
| 431 | 9.8 | 0.0003 | — | 0.025 | — | 0.00017 | — | 0.0037 | 0.084 |
| 432 | <100 | 0.001 | <0.1 | 0.032 | — | 0.0012 | — | >0.01 | — |
| 433 | <100 | 0.0003 | — | 0.02 | — | 0.00017 | — | 0.005 | 0.078 |
| 434 | <100 | 0.003 | — | >0.1 | — | 0.0017 | — | 0.009 | — |
| 435 | <100 | 0.001 | — | 0.04 | — | 0.002 | — | >0.01 | — |
| 436 | <100 | 0.0006 | — | <0.1 | — | 0200075 | — | >0.01 | — |
| 437 | <100 | 0.0003 | — | 0.025 | — | 0.00075 | — | >0.01 | — |
| 438 | >100 | 0.0003 | — | <0.1 | — | 0.0009 | — | >0.01 | — |
| 439 | >100 | 0.0003 | — | >0.1 | — | 0.00045 | — | >0.01 | — |
| 440 | >100 | 0.0003 | — | <0.1 | — | 0.002 | — | >0.01 | — |
| 441 | <100 | 0.0003 | — | 0.016 | — | 0.000025 | — | 0.006 | — |
| 442 | <100 | 0.001 | — | 0.035 | — | 0.0007 | — | >0.01 | — |
| 443 | <100 | 0.0003 | — | 0.017 | — | 0.00015 | — | <0.01 | — |
| 444 | >100 | 0.0006 | — | 0.023 | — | 0.00015 | — | >0.01 | — |
| 445 | <100 | 0.001 | — | >0.1 | — | 0.00045 | — | >0.01 | — |
| 446 | >100 | 0.001 | — | <0.1 | — | 0.0008 | — | >0.01 | — |
| 447 | 33 | >0.05 | — | >0.1 | — | 0.0009 | — | — | — |
| 448 | 16 | >0.05 | — | 0.03 | — | 0.003 | — | — | — |
| 449 | 13 | — | — | 0.025 | — | 0.0001 | — | 0.0075 | — |
| 450 | 72 | — | 0.0001 | 0.015 | 0.005 | 0.00016 | — | 0.01 | — |
| 451 | 3.6 | 0.001 | 0.00025 | >0.1 | — | 0.0001 | 0.0002 | 0.0051 | 0.065 |
| 452 | >100 | 0.0003 | — | <0.1 | — | 0.0017 | — | >0.01 | 0.1 |
| 453 | >100 | >0.05 | — | — | — | 0.1 | — | — | — |
| 454 | >100 | >0.05 | — | >0.1 | — | 0.03 | — | — | — |
| 455 | >100 | 0.01 | — | >0.1 | — | 0.0025 | — | — | — |
| 456 | >100 | 0.01 | — | >0.05 | — | 0.017 | >0.05 | >0.01 | — |
| 457 | >100 | >0.05 | — | >0.05 | — | 0.009 | >0.05 | — | — |
| 458 | 100 | >0.05 | — | >0.05 | — | 0.007 | — | — | — |
| 459 | >100 | >0.05 | — | 0.1 | — | 0.008 | — | >0.01 | — |
| 460 | >100 | >0.05 | — | >0.1 | — | 0.02 | — | >0.01 | — |
| 461 | 6 | 0.001 | — | 0.01 | 0.0035 | 0.00008 | — | 0.0075 | >2.5 |
| 462 | 7 | 0.001 | 0.0025 | 0.04 | — | 0.001 | 0.001 | >0.05 | — |
| 463 | 8 | 0.05 | — | 0.0075 | 0.0024 | 0.00009 | 0.0003 | 0.01 | — |
| 464 | >100 | — | — | >0.1 | — | 0.08 | — | — | — |
| 465 | 8 | — | — | 0.027 | — | 0.0017 | 0.0025 | — | — |
| 466 | 13 | — | — | >0.1 | — | 0.0008 | >0.05 | 0.01 | — |
| 467 | 6 | — | — | 0.04 | — | 0.003 | — | — | — |
| 468 | 50 | 0.05 | — | >0.1 | — | >0.1 | — | — | — |
| 469 | 40 | >0.05 | — | >0.1 | — | 0.02 | — | — | — |
| 470 | 25 | >0.05 | — | >0.1 | — | 0.02 | — | — | — |
| 471 | <100 | 0.001 | — | 0.018 | — | 0.00018 | — | >0.01 | — |
| 472 | >100 | — | — | >0.1 | — | 0.0025 | — | — | — |
| 473 | >100 | — | — | >0.1 | — | 0.025 | — | — | — |
| 474 | 8 | — | — | >0.1 | — | 0.0012 | — | — | — |
| 475 | >100 | >0.05 | — | >0.1 | — | 0.008 | >0.05 | >0.01 | — |
| 476 | >100 | — | — | >0.1 | — | 0.015 | — | — | — |
| 477 | 20 | — | — | >0.1 | — | 0.0003 | — | 0.0076 | — |
| 478 | 15 | — | — | >0.1 | — | 0.0037 | — | >0.01 | — |
| 479 | 66 | >0.05 | — | >0.1 | — | 0.013 | >0.05 | >0.01 | — |

TABLE 3-continued

| Cmpd. No. | HF μg | BBA % | TBW, % C | TBW, % E | BAW % | CL % | LH % | MW % | RWW μg |
|---|---|---|---|---|---|---|---|---|---|
| 480 | >100 | >0.05 | — | >0.1 | — | 0.01 | — | — | — |
| 481 | >100 | — | — | >0.1 | — | 0.015 | — | — | — |
| 482 | 36 | — | — | >0.1 | — | 0.01 | — | >0.01 | — |
| 483 | 6 | — | — | 0.05 | — | 0.001 | — | >0.01 | — |
| 484 | 16 | — | — | >0.1 | — | 0.003 | — | — | — |
| 485 | 24 | — | — | >0.1 | — | >0.1 | — | — | — |
| 486 | 15 | — | — | >0.1 | — | >0.1 | — | >0.01 | — |
| 487 | >100 | — | — | >0.1 | — | 0.023 | — | — | — |
| 488 | >100 | — | — | >0.1 | — | 0.025 | — | — | — |
| 489 | >100 | — | — | >0.1 | — | <0.1 | — | — | — |
| 490 | >100 | >0.05 | — | >0.1 | — | 0.0045 | >0.05 | >0.01 | — |
| 491 | 9 | — | — | 0.08 | — | 0.0028 | — | — | — |
| 492 | 15 | >0.05 | — | 0.015 | — | 0.00028 | >0.05 | >0.01 | — |
| 493 | 36 | — | — | 0.05 | — | 0.0008 | — | — | — |
| 494 | 34 | — | — | >0.1 | — | 0.003 | — | — | — |
| 495 | >100 | — | — | 0.1 | — | 0.012 | — | — | — |
| 496 | >100 | — | — | >0.1 | — | 0.006 | — | — | — |
| 497 | >100 | — | — | >0.1 | — | 0.0075 | — | — | — |
| 498 | 49 | >0.05 | — | >0.1 | — | 0.002 | — | — | — |
| 499 | 63 | >0.05 | — | >0.1 | — | 0.0024 | — | — | — |
| 500 | 16 | >0.05 | 0.00075 | 0.02 | 0.002 | 0.00009 | — | — | — |
| 501 | 20 | >0.05 | — | >0.1 | — | 0.00045 | — | — | — |
| 502 | 80 | — | — | — | — | — | — | — | — |
| 503 | 21 | 0.006 | — | 0.08 | — | 0.001 | — | >0.01 | — |
| 504 | <100 | 0.0003 | — | 0.05 | — | 0.00025 | — | 0.01 | — |
| 505 | 14 | 0.002 | — | 0.09 | — | 0.0024 | — | >0.01 | — |
| 506 | 40 | 0.03 | — | >0.1 | — | 0.005 | — | >0.01 | — |
| 507 | 93 | 0.05 | — | >0.1 | — | 0.002 | — | >0.01 | — |
| 508 | >100 | — | — | >0.1 | — | 0.013 | — | >0.01 | — |
| 509 | 79 | >0.05 | — | >0.1 | — | 0.0075 | — | >0.01 | — |
| 510 | 54 | 0.05 | — | >0.1 | — | 0.017 | — | >0.01 | — |
| 511 | 89 | 0.05 | — | >0.1 | — | 0.0012 | — | >0.01 | — |
| 512 | 35 | >0.05 | — | >0.1 | — | 0.003 | >0.05 | >0.01 | — |
| 513 | 81 | >0.05 | — | >0.1 | — | 0.007 | >0.05 | >0.01 | — |
| 514 | >100 | 0.003 | — | >0.1 | — | 0.008 | >0.05 | >0.01 | — |
| 515 | 28 | >0.05 | — | >0.1 | — | 0.0015 | >0.05 | >0.01 | — |
| 516 | >100 | >0.05 | — | >0.1 | — | 0.008 | >0.05 | >0.01 | — |
| 517 | 80 | >0.05 | — | 0.04 | — | 0.0008 | >0.05 | >0.01 | — |
| 518 | >100 | >0.05 | — | >0.1 | — | 0.00075 | >0.05 | >0.01 | — |
| 519 | 60 | >0.05 | — | >0.1 | — | 0.0037 | >0.05 | >0.01 | — |
| 520 | 5.5 | 0.0002 | 0.00075 | >0.1 | — | >0.1 | 0.0003 | 0.0042 | — |
| 521 | 7.5 | 0.0008 | 0.0005 | >0.1 | — | 0.00005 | 0.05 | 0.01 | — |
| 522 | 17.5 | 0.002 | — | >0.1 | — | >0.1 | 0.05 | >0.01 | — |
| 523 | 22 | 0.001 | 0.0002 | >0.1 | — | 0.00015 | >0.05 | >0.01 | — |
| 524 | 5.2 | >0.05 | — | >0.1 | — | >0.1 | >0.05 | >0.01 | — |
| 525 | >100 | >0.05 | — | >0.1 | — | <0.1 | >0.05 | >0.01 | — |
| 526 | 8.3 | >0.05 | — | >0.1 | — | >0.1 | >0.05 | >0.01 | — |
| 527 | 47 | 0.03 | — | 0.035 | — | 0.00065 | >0.05 | >0.01 | — |
| 528 | 59.1 | >0.05 | — | >0.1 | — | 0.0075 | >0.05 | >0.01 | — |
| 529 | 27.7 | >0.05 | — | >0.1 | — | >0.0025 | >0.05 | >0.01 | — |
| 530 | 9.8 | 0.0003 | 0.00005 | 0.005 | — | 0.00027 | 0.05 | >0.01 | — |
| 531 | 5 | >0.05 | 0.00037 | >0.1 | — | >0.1 | >0.05 | >0.01 | — |
| 532 | >100 | >0.05 | — | >0.1 | — | <0.1 | >0.05 | >0.01 | — |
| 533 | 60 | >0.05 | — | >0.1 | — | >0.1 | >0.05 | >0.01 | — |
| 534 | >100 | >0.05 | — | >0.1 | — | <0.1 | >0.05 | >0.01 | — |
| 535 | 41 | >0.05 | — | >0.1 | — | >0.1 | >0.05 | >0.01 | — |
| 536 | >100 | <0.05 | — | >0.1 | — | <0.1 | >0.05 | >0.01 | — |
| 537 | 20 | >0.05 | — | >0.1 | — | >0.1 | >0.05 | >0.01 | — |
| 538 | 75 | >0.05 | — | >0.1 | — | >0.1 | >0.05 | >0.01 | — |
| 539 | 22 | >0.05 | — | >0.1 | — | >0.1 | >0.05 | >0.01 | — |
| 540 | >100 | >0.05 | — | >0.1 | — | <0.1 | >0.05 | >0.01 | — |
| 541 | <100 | 0.004 | — | >0.1 | — | 0.001 | >0.05 | >0.01 | — |
| 542 | >100 | >0.05 | — | >0.1 | — | >0.01 | >0.05 | >0.01 | — |
| 543 | <100 | 0.003 | — | >0.1 | — | 0.0008 | <0.05 | >0.01 | — |
| 544 | >100 | 0.005 | — | >0.1 | — | >0.1 | >0.05 | >0.01 | — |
| 545 | <100 | 0.005 | — | >0.1 | — | >0.1 | >0.05 | >0.01 | — |
| 546 | <100 | 0.001 | — | >0.1 | — | 0.0001 | <0.05 | 0.0032 | — |
| 547 | <100 | 0.0006 | — | 0.05 | — | 0.0005 | <0.05 | >0.01 | — |
| 548 | >100 | >0.05 | — | >0.1 | — | <0.1 | >0.05 | >0.01 | — |
| 549 | <100 | >0.05 | — | >0.1 | — | >0.1 | >0.05 | >0.01 | — |
| 550 | <100 | 0.002 | — | >0.1 | — | 0.00034 | — | >0.01 | — |
| 551 | <100 | 0.0006 | — | 0.035 | — | 0.00075 | — | >0.01 | — |
| 552 | >100 | 0.002 | — | >0.1 | — | 0.0016 | — | >0.01 | — |
| 553 | <100 | 0.05 | — | 0.1 | — | <0.1 | — | >0.01 | — |
| 554 | >100 | 0.003 | — | 0.04 | — | 0.00075 | — | >0.01 | — |
| 555 | <100 | 0.0035 | — | >0.1 | — | 0.002 | — | >0.01 | — |
| 556 | <100 | 0.0035 | — | 0.04 | — | 0.0007 | — | >0.01 | — |
| 557 | <100 | 0.0015 | — | >0.1 | — | 0.0004 | — | >0.01 | — |

TABLE 3-continued

| Cmpd. No. | HF μg | BBA % | TBW, % (LC$_{50}$) C | TBW, % (LC$_{50}$) E | BAW % | CL % | LH % | MW % | RWW μg |
|---|---|---|---|---|---|---|---|---|---|
| 558 | <100 | 0.0012 | — | >0.1 | — | 0.00045 | — | >0.01 | — |
| 559 | <100 | 0.0035 | — | 0.017 | — | 0.00027 | — | >0.01 | — |
| 560 | <100 | 0.0025 | — | <0.1 | — | 0.0015 | — | >0.01 | — |

*Compound demonstrated activity in tests against two-spotted mite.
(see below)

The compounds in Tables 1 and 2 were also tested for activity against the two-spotted mite [*Tetranychus urticae* (Koch)] and Western spotted cucumber beetle larvae [*Diabrotica undecimpunctata undecimpunctata* (Mannerheim)]. Initial testing levels were 0.05% (in solution) against the mite, and 25 ppm (in soil) against the beetle. Some compounds demonstrated 50% or more mortality against one or the other insect at the initial testing level, but most did not.

Other compounds within the scope of this invention which have been prepared and have shown 50% or greater mortality against at least one insect in tests as described above are listed below. Most of these compounds are analogous to a compound in Table 1 or 2, that is, they have the same groups indicated for $R_2$ and $R_3$ (or $R_4$ and $R_5$ of Table 1), differing only in having different substituents on the phenyl ring from the indicated compound. These were:

Analogous to compound 81 in which the substituents on the phenyl ring are: 3-Cl,4-Br; 3-CF$_3$,4-Br; 4-SO$_2$CH$_3$; 2-Cl,4-CF$_3$; 3-F,4-OCH$_2$CF$_3$; 3-OCH$_3$,4-Br; 3-Br,4-OCH$_3$; 3-F,4-OCH$_3$; 3-Cl,4-C$_2$H$_5$; 2-Cl,5-C$_2$H$_5$; 3-F,4-OC$_2$H$_5$; 4-n-C$_3$H$_7$; 2,3,4-F; 3-Cl,4-OC$_2$H$_5$; 3-OC$_2$H$_5$,4-Br; 3-Br,4-OC$_2$H$_5$; 3-OCH$_3$,4-Cl; 3-OCH$_3$,4-CF$_3$; 3-OC$_2$H$_5$,4-Cl; 2-NO$_2$,4-CF$_3$; 3-F,4-I; 3-Cl,4-OCHF$_2$; 3-Br,4-C$_2$H$_5$; 2,3-F; 3-Br,4-CH$_3$; 3-I,4-CH$_3$; and 4-n-C$_3$F$_7$;

Analogous to compound 82 in which the substituents on the phenyl ring are: 4-CH$_3$; 4-OCH$_3$; 2,3-CH$_3$; 2,4-CH$_3$; 3,4-CH$_3$; 3,4-OCH$_3$; 3-C$_2$H$_5$; 3-CH$_3$; 3-Cl; 4-Br; 3-CF$_3$,4-Br; 4-I; 3-F; 3-Cl,4-Br; 3-Cl,4-I; 3-I; 4-CN; 3-OCH$_3$; 4-SO$_2$CH$_3$; 3-OC$_2$H$_5$; 3-OCH$_3$,4-Br; 3-Br,4-OCH$_3$; 3-Cl,4-C$_2$H$_5$; 3-OCH$_3$,4-Cl; 3-OCH$_3$,4-CF$_3$; 3-OCH$_3$,4-Br; 3-F,4-Cl; 3-Br,4-OC$_2$H$_5$; 3-Cl,4-OCHF$_2$; 3-F,4-I; 2,3-F; 4-n-C$_3$H$_7$; 3-Br,4-C$_2$H$_5$; 3-Br,4-CH$_3$; 4-n-C$_4$H$_9$; 3-I,4-CH$_3$; 4-n-C$_3$F$_7$; and 4-OCF$_2$CHF$_2$;

Analogous to compound 89 in which the substituents on the phenyl ring are: 4-OCF$_3$; 3-Cl,4-Br; 3-F,4-Br; 3-NO$_2$,4-F; 3-CF$_3$; 3-F,4-CH$_3$; 2-Cl,5-F; 2,5-F; 3-CF$_3$,4-NO$_2$; 4-t-C$_4$H$_9$; 3-CF$_3$,4-Br; 2-Br,4-t-C$_4$H$_9$; 2-Br,4-i-C$_3$H$_7$; 3,5-CH$_3$; 3-CH$_3$; 2,4-CH$_3$; 3,4-CH$_3$; 3-CH$_3$,4-Br; 2,3-CH$_3$; 4-OCH$_3$; 4-SCH$_3$; 3,4-OCH$_3$; 3-OC$_2$H$_5$; 3-OCH$_3$,4-Br; 4-OC$_2$H$_5$; 4-Cl,4-OC$_2$H$_5$; 3-Br,4-OCH$_3$; 3-F,4-OCH$_3$; 3-OCF$_3$; 2-Cl,5-OC$_2$H$_5$; 3-F,4-OC$_2$H$_5$; 4-n-C$_3$H$_7$; 3-OCH$_3$,4-Cl; 3-OCH$_3$,4-CF$_3$; 3-OC$_2$H$_5$,4-Cl; 3-OCH$_3$,4-Br; 3-Br,4-OC$_2$H$_5$; 3-Cl,4-OCHF$_2$; 3-F,4-I; 3-Br,4-C$_2$H$_5$; 3-Br,4-CH$_3$; 4-n-C$_4$H$_9$; and 4-n-C$_3$F$_7$;

Analogous to compound 191 in which the substituents on the phenyl ring are: 4-F; 2,3,4-F and 2,4-F,3-Cl;

Analogous to compound 216 in which the substituents on the phenyl ring are: 3,4-(-OCH$_2$O-); 3-Br; 4-Cl; 4-F; 4-CH$_3$; 2,4-CH$_3$; 4-OCH$_3$; 2,3-CH$_3$; 3,4-CH$_3$; 3-C$_2$H$_5$; 3-SCH$_3$; 3-CH$_3$; 3-Cl,4-I; 3-OCH$_3$; 4-SCH$_3$; 2-Cl,4-CF$_3$; 3-OCH$_3$,4-Br; 3-F,4-OCH$_3$; 3-Br,4-OCH$_3$; 3-OCF$_3$; 3-Cl,4-C$_2$H$_5$; 3-F,4-OC$_2$H$_5$; 3-OCH$_3$,4-Cl; 3-CF$_3$,4-OCH$_3$; 3-OC$_2$H$_5$,4-Cl; 3-OC$_2$H$_5$,4-Br; 3-Br,4-OC$_2$H$_5$; 3-F,4-I; 3-Br,4-C$_2$H$_5$; 4-n-C$_4$H$_9$; 2-F,4-CH$_3$; 2-F,4-Cl; 2,4-F; 3-I,4-CH$_3$; and 4-O-n-C$_3$H$_7$;

Analogous to compound 217 in which the substituents on the phenyl ring are 3-Cl,4-C$_2$H$_5$; 4-CF$_3$; 3-Cl,4-CH$_3$ and 4-OCF$_3$;

Analogous to compound 238 in which the substituents on the phenyl ring are: 3-CF$_3$; 3-F; 3-I; 3-F,4-CF$_3$; and 4-Br;

Analogous to compound 239 in which the substituents on the phenyl ring are: 3-CF$_3$; 3,4-F; 3-OCH$_3$; 3-CH$_3$; 4-OC$_2$H$_5$; 2-Cl; 2-CH$_3$; 3-NO$_2$,4-F; 3-4-Cl; 3-F,4-CF$_3$; 4-t-C$_4$H$_9$; 3-Cl; 3-F; 3-CF$_3$,4-Br; 4-Br; 4-I; 4-C$_2$H$_5$; 3-F,4-Br; 3,4-Br; 3-CF$_3$,4-Cl; 4-OCF$_3$; 3-SCH$_3$; 4-F; 2,4-CH$_3$; 4-CH$_3$; 3,4-CH$_3$; 3-CH$_3$,4-Br; 3-Cl,4-OCH$_3$; 2,3-CH$_3$; 4-OCH$_3$; 4-SCH$_3$; 3-Cl,4-OCH$_2$CF$_3$; 2-Cl,4-CF$_3$; 3-OCH$_3$,4-Br; 3-Br,4-OCH$_3$; 3-OCF$_3$; 3-Cl,4-C$_2$H$_5$; 3-F,4-OC$_2$H$_5$; 2,3,4-F; 3-F,4-CH$_3$; 3-CF$_3$,4-OCH$_3$; 3-OC$_2$H$_5$,4-Cl; 3-OC$_2$H$_5$,4-Br; 3-Br,4-OC$_2$H$_5$; 3-Cl,4-OCHF$_2$; 3-F,4-I; 3-Br,4-C$_2$H$_5$; 4-n-C$_3$H$_7$; 3-Br,4-CH$_3$; 4-n-C$_4$H$_9$; 2-F,4-CH$_3$; 2-F,4-Cl; 3-I,4-CH$_3$; 4-n-C$_3$H$_7$; and 4-OCF$_2$CHF$_2$;

Analogous to compound 267 in which the substituents on the phenyl ring are: 4-I; 4-C$_2$H$_5$; 3,4-Br, 3-Cl,4-I; 3-I; 3-SCH$_3$; 2,4-CH$_3$; 2-C$_2$H$_5$; 3-OCH$_3$; 4-SO$_2$CH$_3$; 2-Cl,4-CF$_3$; 3,4-OCH$_3$; 3-OC$_2$H$_5$; 3-OCH$_3$,4-Br; 3-Br,4-OCH$_3$; 3-F,4-OCH$_3$; 4-OCH$_2$CF$_3$; 3-Cl,4-OCH$_3$; 3-F,4-CH$_3$; 3-OCH$_3$,4-Cl; 3-CF$_3$,4-OCH$_3$; 3-OC$_2$H$_5$,4-Cl; 3-OC$_2$H$_5$,4-Br; 3-F,4-Cl; 2-NO$_2$,4-CF$_3$; 3-Br,4-OC$_2$H$_5$; 3-F,4-I; 3-Br,4-C$_2$H$_5$; 2,3-F; 4-n-C$_3$H$_7$; 3-Br,4-CH$_3$; 4-n-C$_4$H$_9$; 2-F,4-Cl; 3,5-F; 3-I,4-CH$_3$; 4-n-C$_3$F$_7$; and 4-OCF$_2$CHF$_2$;

Analogous to compound 274 in which the substituents on the phenyl ring are 3-Cl,4-F;

Analogous to compound 447 in which the substituent on the phenyl ring is 4-I;

Analogous to compound 461, in which the substituent on the phenyl ring is 4-CF$_3$;

Analogous to compound 462 in which the substituents on the phenyl ring are: 3-Cl,4-OCHF$_2$; 3-Cl,4-CH$_3$; 2,3-CH$_3$; 3-CF$_3$,4-Br; 3,4-(-OCH$_2$O-); 3-NO$_2$; 2-Cl; 2-CH$_3$; 3-CF$_3$,4-F; 3-F,4-CH$_3$; 3-Cl,4-OCH$_3$; 3,4-OCH$_3$; 4-Br; 4-CF$_3$; 2,4-F,3-Cl; 4-CN; 3-F,4-Br; 4-C$_2$H$_5$; 3-CH$_3$,4-F; 3-Br; 4-I; 2-Cl,4-CF$_3$; 3,4-F; 3-Cl; 3-C$_2$H$_5$; 4-F; 4-CH$_3$; 3-CH$_3$; 3-OCH$_3$; 3-Cl,4-OCH; 3-F; 4-OCH$_2$CF$_3$; 4-OC$_2$H$_5$; 3,4-OC$_2$H$_5$; 3,4-CH$_3$; 3-Cl,4-I; 2,4-Cl and 3,4-Cl;

Analogous to compound 510 in which the substituent on the phenyl ring is 3-Cl,4-F;

Analogous to compound 516 in which the substituents on the phenyl ring are 3,4-(-OCH$_2$O-) and 2,4-F,3-Cl;

Analogous to compound 517 in which the substituents on the phenyl ring are 3,4-(-OCH$_2$O-) and 4-CF$_3$;

Analogous to compound 518 in which the substituents on the phenyl ring are 2,4-F,3-Cl;

Analogous to compound 520 in which the substituent on the phenyl ring is 3-CF$_3$;

And the compounds shown below in Table 4.

TABLE 4

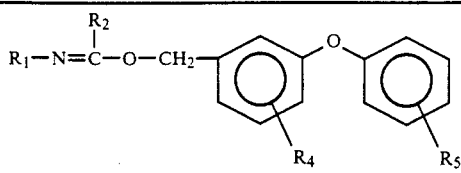

| Phenyl Subst. | R$_2$ | R$_4$ | R$_5$ |
|---|---|---|---|
| 3-Cl,4-F | CHCl$_2$ | H | 4-F |
| 4-i-C$_3$H$_7$ | sec.-C$_4$H$_9$ | H | 4-F |
| 4-i-C$_3$H$_7$ | C$_2$H$_5$ | H | H |
| 4-i-C$_3$H$_7$ | CHBrCH$_3$ | H | 4-F |
| 4-i-C$_3$H$_7$ | CHBrCH$_3$ | H | H |
| 4-CF$_3$ | —C(CH$_3$)—CH$_2$ | 4-F | 4-F |
| 4-F | —C(CH$_3$)—CH$_2$ | H | H |
| 4-F | —C(CH$_3$)—CH$_2$ | 4-F | 4-Cl |
| 4-F | —C(CH$_3$)—CH$_2$ | 4-F | H |
| 3,4-F | —C(CH$_3$)—CH$_2$ | H | H |
| 3,4-F | —C(CH$_3$)—CH$_2$ | 4-F | 4-Cl |
| 3,4-F | —C(CH$_3$)—CH$_2$ | 4-F | H |
| 3,4-(—OCH$_2$O—) | —C(CH$_3$)—CH$_2$ | H | H |
| 3,4-(—OCH$_2$O—) | —C(CH$_3$)—CH$_2$ | 4-F | 4-Cl |
| 3,4-(—OCH$_2$O—) | —(CCH$_3$)—CH$_2$ | 4-F | H |
| 4-OCF$_3$ | —C(CH$_3$)—CH$_2$ | H | H |
| 4-OCF$_3$ | —C(CH$_3$)—CH$_2$ | 4-F | 4-Cl |
| 4-OCF$_3$ | —C(CH$_3$)—CH$_2$ | 4-F | H |
| 3-Cl,4-F | CH=C(CH$_3$)$_2$ | H | H |
| 3-Br,4-F | —C(CH$_3$)—CH$_2$ | H | H |
| 3-Br,4-F | —C(CH$_3$)—CH$_2$ | 4-F | 4-Cl |
| 3-Br,4-F | —C(CH$_3$)—CH$_2$ | 4-F | H |
| 3-Br,4-F | —C(CH$_3$)—CH$_2$ | H | 4-Cl |
| 3-F,4-OCHF$_2$ | i-C$_3$H$_7$ | H | H |
| 3-F,4-OCHF$_2$ | i-C$_3$H$_7$ | 4-F | 4-F |
| 3-F,4-OCHF$_2$ | i-C$_3$H$_7$ | 4-F | 4-Cl |
| 3-F,4-OCHF$_2$ | i-C$_3$H$_7$ | H | 4-F |
| 3-F,4-OCHF$_2$ | i-C$_3$H$_7$ | 4-F | H |
| 3-F,4-OCHF$_2$ | i-C$_3$H$_7$ | H | 4-Cl |
| 3-CF$_3$ | —C(CH$_3$)—CH$_2$ | H | 4-Cl |
| 4-OCHF$_2$ | i-C$_3$H$_7$ | H | H |
| 4-OCHF$_2$ | i-C$_3$H$_7$ | H | 4-F |
| 4-OCHF$_2$ | i-C$_3$H$_7$ | 4-F | H |
| 4-OCHF$_2$ | i-C$_3$H$_7$ | H | 4-Cl |
| 3-Cl,4-OCF$_3$ | i-C$_3$H$_7$ | 4-F | 4-F |
| 3-Cl,4-OCF$_3$ | i-C$_3$H$_7$ | 4-F | 4-Cl |
| 3-Cl,4-OCH$_2$CCl=CH$_2$ | i-C$_3$H$_7$ | 4-F | 4-F |
| 3-Cl,4-OCH$_2$CCl=CH$_2$ | i-C$_3$H$_7$ | 4-F | 4-Cl |
| 4-OCH$_2$CCl=CH$_2$ | i-C$_3$H$_7$ | 4-F | 4-F |
| 4-OCH$_2$CCl=CH$_2$ | i-C$_3$H$_7$ | 4-F | 4-Cl |
| 4-C$_2$F$_5$ | i-C$_3$H$_7$ | 4-F | 4-Cl |
| 4-C$_2$F$_5$ | i-C$_3$H$_7$ | 4-F | 4-F |
| 3,4-Cl | CH(CH$_3$)CF$_3$ | 4-F | 4-F |
| 3-Cl,4-F | CH(CH$_3$)CF$_3$ | 4-F | 4-F |
| 2-F,4-CH$_3$ | i-C$_3$H$_7$ | H | H |

TABLE 4-continued

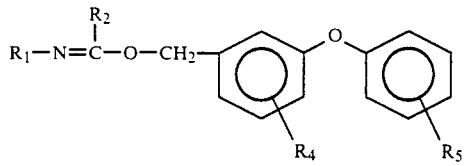

| Phenyl Subst. | R$_2$ | R$_4$ | R$_5$ |
|---|---|---|---|
| 2-F,4-Cl | i-C$_3$H$_7$ | H | H |
| 3-Cl,4-F | —C(CH$_3$)—CH$_2$ | F | F |
| 2,4-F | i-C$_3$H$_7$ | H | 4-Cl |
| 3,5-F | i-C$_3$H$_7$ | 4-F | H |
| 3-I,4-CH$_3$ | i-C$_3$H$_7$ | H | 4-F |
| 4-n-C$_3$F$_7$ | i-C$_3$H$_7$ | 4-F | 4-F |
| 4-OCF$_3$ | —C(CH$_3$)—CH$_2$ | H | 4-Cl |
| 4-OCF$_3$ | —C(CH$_3$)—CH$_2$ | H | 4-F |
| 4-OCF$_3$ | —C(CH$_3$)—CH$_2$ | 4-F | 4-F |
| 3,4-F | —C(CH$_3$)—CH$_2$ | H | 4-Cl |
| 3,4-F | —C(CH$_3$)—CH$_2$ | H | 4-F |
| 3,4-F | —C(CH$_3$)—CH$_2$ | 4-F | 4-F |
| 2,4-F,3-Cl | —C(CH$_3$)—CH$_2$ | H | H |
| 2,4-F,3-Cl | —C(CH$_3$)—CH$_2$ | 4-F | H |
| 2,4-F,3-Cl | —C(CH$_3$)—CH$_2$ | 4-F | 4-Cl |
| 3-CF$_3$ | —C(CH$_3$)—CH$_2$ | H | H |
| 3-CF$_3$ | —C(CH$_3$)—CH$_2$ | 4-F | H |
| 3-CF$_3$ | —C(CH$_3$)—CH$_2$ | 4-F | 4-Cl |
| 3-Br | —C(CH$_3$)—CH$_2$ | H | H |
| 3-Br | —C(CH$_3$)—CH$_2$ | 4-F | H |
| 3-Br | —C(CH$_3$)—CH$_2$ | 4-F | 4-Cl |
| 2,3-F | —C(CH$_3$)—CH$_2$ | H | H |
| 2,3-F | —C(CH$_3$)—CH$_2$ | 4-F | H |
| 2,3-F | —C(CH$_3$)—CH$_2$ | 4-F | 4-Cl |
| 4-SCHF$_2$ | i-C$_3$H$_7$ | 4-F | 4-Cl |
| 4-SCHF$_2$ | i-C$_3$H$_7$ | 4-F | 4-F |
| 3-Cl,4-OCF$_3$ | i-C$_3$H$_7$ | 4-F | H |
| 3-Cl,4-OCF$_3$ | i-C$_3$H$_7$ | H | Cl |
| 4-OCF$_2$CHF$_2$ | i-C$_3$H$_7$ | H | H |
| 4-OCF$_3$ | C$_2$H$_5$ | H | H |
| 3-CF$_3$, 4-OCF$_2$Br | i-C$_3$H$_7$ | 4-F | 4-F |
| 3-CF$_3$,4-OCF$_2$Br | i-C$_3$H$_7$ | H | H |
| 3-F,4-OCF$_3$ | i-C$_3$H$_7$ | 4-F | 4-F |
| 3-F,4-OCF$_3$ | i-C$_3$H$_7$ | H | H |
| 3-Br,4-OCF$_3$ | i-C$_3$H$_7$ | 4-F | 4-F |
| 3-Br,4-OCF$_3$ | i-C$_3$H$_7$ | H | H |
| 3-Br,4-OCF$_2$Br | i-C$_3$H$_7$ | 4-F | 4-F |
| 3-Br,4-OCF$_2$Br | i-C$_3$H$_7$ | H | H |

For information, the following Table 5 lists a very small number of compounds within the definition of the class of this invention which did not produce 50% or greater mortality in an insecticidal evaluation test to date.

TABLE 5

$$R_1-N=\underset{\underset{R_2}{|}}{C}-OR_3$$

| Phenyl Subst. | R$_2$ | R$_3$ |
|---|---|---|
| 4-Cl | CHCl$_2$ | 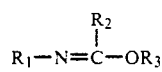 |
| 4-OCF$_3$ | CHClCH$_2$CH$_2$Cl | —CH$_2$— (phenoxyphenyl) |

TABLE 5-continued
$$R_1-N=\overset{R_2}{\underset{|}{C}}-OR_3$$
| Phenyl Subst. | R₂ | R₃ |
|---|---|---|
| 2,3-Cl | i-C₃H₇ | 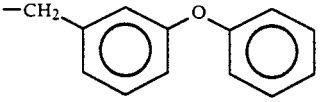 |
| H | C(CH₃)2CH2Cl | 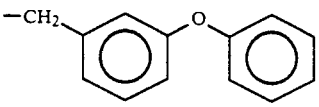 |
| 3,5-CF₃ | i-C₃H₇ | 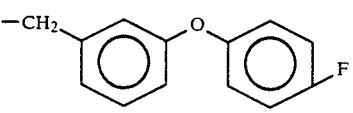 |
| 3-Cl | i-C₃H₇ | 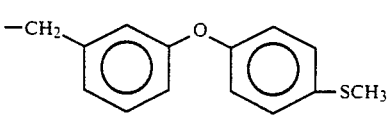 |
| 3,5-Cl | i-C₃H₇ | 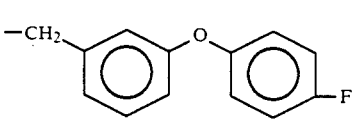 |
| 2,4-Cl | i-C₃H₇ | 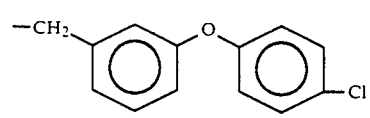 |
| 3,4-Cl | i-C₃H₇ | 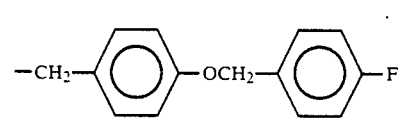 |
| 3-Cl | t-C₄H₉ | 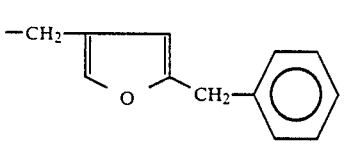 |
| 3,4-OCH₃ | i-C₃H₇ | 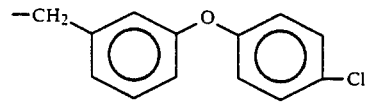 |
| 4-Cl | —C(CH₃)—CH₂ | 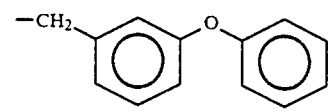 |
| 3-Cl,4-F | i-C₃H₇ | 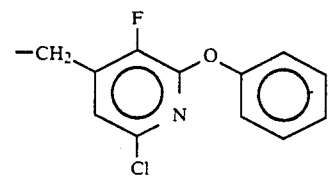 |

TABLE 5-continued $$R_1-N=C(R_2)-OR_3$$

| Phenyl Subst. | $R_2$ | $R_3$ |
|---|---|---|
| 3-CF$_3$ | i-C$_3$H$_7$ | 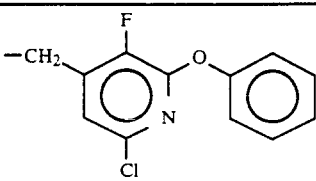 |

The insecticidal activity, and therefore the inclusion of a compound not mentioned specifically herein within the class of compounds of this invention, as determined by the general formula (I), may be determined by evaluating such a compound using one or more of the above-described procedures. If a test compound demonstrates activity against one or more of the insects mentioned, by virtue of causing 50 percent or greater mortality at the initial evaluation level, it is considered "insecticidal" for the purposes of this invention.

In practice, a pure compound (active compound) can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active compounds are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. The particular pesticide included in the mixture will depend upon its intended utility and the type of complementary action required. Examples of suitable insecticides include the following:

(a) natural pyrethrins or pyrethroids such as permethrin, fenvalerate, deltamethrin, cyhalothrin, biphenthrin, fenpropathrin, cyfluthrin, tefluthrin, empenthrin, ethofenprox, tetramethrin, bioallethrin, fenfluthrin, prallethrin, 5-benzyl-3-furylmethyl-(E)-(1R,3S)-2,2-dimethyl-3-(2-oxothiolan-3-yli dene- methyl)cyclopropane carboxylate and pentafluorobenzyl (cis)-3-[-2-fluoro-2-(methoxycarbonyl)ethenyl]-2,2-dimethylcyclopropane carboxylate;

(b) organophosphates such as profenofos, sulprofos, phosmet, dichlorvos, methyl parathion, azinphosmethyl, dimeton-s-methyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim, pyrimiphosmethyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron, chlorofluazuron;

(e) organic tin compounds such as cyhexatin, fenbutatin oxide and azocyclotin;

(f) macrolides such as avermectins or milbemycins, for example such as abamectin, avermectin, and milbemycin;

(g) hormones and synthetic mimics thereof such as juvenile hormone, juvabione, ecdysones, methoprene and hydroprene;

(h) pheromones; and (i) organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofesin, can be employed. Alternatively, insecticides specific for particular insect species/stages, for example ovolarvicides such as clofentezine, amitraz, chlordimeform flubenzimine, hexythiazox and tetradifon, motilicides such as dicofol or propargite, adulticides such as bromopropylate, chlorbenzilate, or insect growth regulators such as hydramethylon, cyromazine, methoprene, chlorofluazuron and diflubenzuron may also be included in the compositions. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compounds of this invention could be used to control a variety of insects such as:

*Myzus persicae* (aphid)
*Aphis gossypii* (aphid)
*Aphis fabae* (aphid)
*Megoura viceae* (aphid)
*Aedes aegypti* (mosquito)
Anopheles spp. (mosquitos)
Culex spp. (mosquitos)
*Dysdercus fasciatus* (capsid)
*Musca domestica* (housefly)
*Pieris brassicae* (white butterfly)
*Plutella maculipennis* (diamond back moth)
*Phaedon cochlaeriae* (mustard beetle)
Aonidiella spp. (scale insects)
Trialeuroides spp. (white flies)
*Bemisia tabaci* (white fly)
*Blattella germanica* (cockroach)
*Periplaneta americana* (cockroach)
*Blatta orientalis* (cockroach)
*Spodoptera littoralis* (cotton leafworm)
*Heliothis virescens* (tobacco budworm)
*Chortiocetes terminifera* (locust)
Diabrotica spp. (rootworms)
Agrotis spp. (cutworms)
*Chilo supressalis* (stem borer
*Chilo partellus* (maize stem borer)
*Nilaparvata lugens* (planthopper)
*Nephottex virescens* (leafhopper
*Nephotettix cincticeps* (leafhopper)
*Panonychus ulmi* (European red mite)
*Panonychus citri* (citrus red mite)
*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
Brevipalpus spp. (mites).

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | Weight % |
|---|---|
| Composition A: Granular Solid | |
| Active compound | 10 |
| attapulgite clay granules | 85 |
| triethylene glycol | 5 |
| Total | 100% |
| Composition B: Wettable Powder | |
| Active compound | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |
| Composition C: Dilute Solution | |
| Active compound | 5 |
| solvent (xylene) | 95 |
| Total | 100% |
| Composition D: Emulsifiable Concentrate | |
| Active compound | 50 |
| Emulsifier (blend of metal sulfonates and polyoxyethylene ethers) | 10 |
| solvent (xylene) | 40 |
| Total | 100% |
| Composition E: Concentrated Solution | |
| Active compound | 90 |
| solvent (xylene) | 10 |
| Total | 100% |

What is claimed is:

1. A compound having the formula

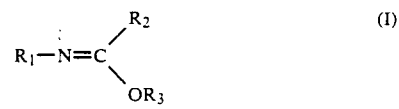

in which $R_1$ is naphthyl, optionally substituted by up to 2 halogens; or phenyl, optionally substituted by one or more of: $C_2$-$C_5$ carboalkoxy, $C_1$-$C_4$ alkylsulfonyl, $C_1$-$C_4$ haloalkylsulfonyl, $C_2$-$C_5$ alkylcarbonyl, $C_2$-$C_4$ alkenyl, $C_3$-haloalkenoxy; $C_1$-$C_4$ haloalkylthio, $C_3$-$C_6$ cycloalkyl, phenyl, mono-substituted phenyl, pyridyloxy, $C_2$-$C_4$ alkyleneoxy, $C_1$-$C_2$ perhaloalkyleneoxy; $C_1$-$C_4$ alkylenedioxy, $C_1$-$C_3$ haloalkylenedioxy, $C_2$-$C_4$ alkylene, amido, nitro, cyano, up to two $C_1$-$C_4$ alkylthio groups, up to three $C_1$-$C_4$ alkoxy groups, up to three $C_1$-$C_4$ haloalkoxy groups, up to three $C_1$-$C_4$ alkyl groups, up to three $C_1$-$C_4$ haloalkyl groups, or up to five halogens;

$R_2$ is methyl; ethyl; n-propyl; $C_3$-$C_7$ branched alkyl; $C_1$-$C_6$ haloalkyl, cyclobutyl substituted by up to 4 methyl groups or up to 2 halogens, cyclobutyl, cyano, $C_2$-$C_4$ alkoxyalkyl, $C_2$-$C_6$ alkenyl or $C_2$-$C_6$ haloalkenyl; and $R_3$ is (a)

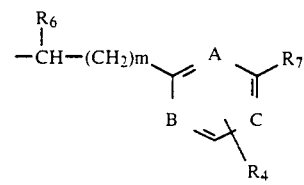

in which m is 0 or 1;

A, B and C are each carbon or nitrogen, provided that A, B and C are not all nitrogen and if two of A, B and C are nitrogen, then A and C are nitrogen;

$R_4$ is hydrogen, monohalo or dihalo;

$R_6$ is hydrogen, methyl, fluoro or ethynyl; and $R_7$ is (i)

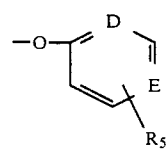

in which D and E are each carbon or nitrogen provided that both D and E are not nitrogen, and further provided that if any of A, B or C is nitrogen, then D and E are both carbon; and $R_5$ is hydrogen, $C_1$-$C_4$ alkyl, $C_1$-$C_4$ alkoxy, trifluoromethyl, cyano, $C_1$-$C_4$ alkylthio, $C_1$-$C_4$ alkylsulfonyl, or mono- or polyhalo;

(ii)

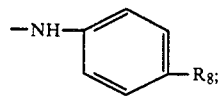

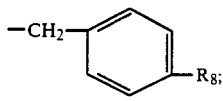

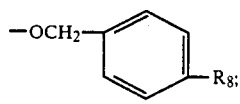

in which $R_8$ is hydrogen or halogen; or (iii) —O—$CH_2$—CH=$CH_2$;

(b)

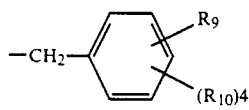

in which
(i) $R_9$ is 4-fluoro, 4-methoxymethyl, or 4-propargyl, and $R_{10}$ is fluoro or
(ii) $R_9$ is 3- or 4-allyl, 3- or 4-propargyl, or 3- or 4-(mono- or dihalo)allyl, and $R_{10}$ is hydrogen or fluoro;

(c)

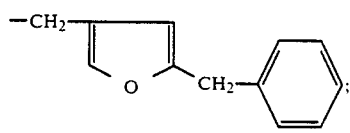

(d) 4-phenoxy-2-butyn-2-yl;
(e) 3-bromo-4-fluorobenzyl;
(f) 4-(benzyloxy)benzyl;
(g) 4-(4-fluorobenzyloxy)benzyl;
(h) 4-(4-trifluoromethyl-2-pyridyloxy)benzyl; or
(j)

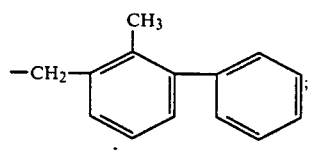

provided that:
(i) $R_1$ is not 2,3-dichlorophenyl, 2,6-difluorophenyl, 2,6-di($C_1$-$C_4$ alkyl)phenyl, 2,4,6-tribromophenyl or 2,4,6-tri($C_1$-$C_4$ alkoxy)phenyl;
(ii) when $R_2$ is tertiary butyl, $R_1$ is not phenyl, 3-methylphenyl, 4-(n-butyl)phenyl or 4-(t-butyl)phenyl; and
(iii) when $R_2$ is a $C_5$ alkyl group, $R_1$ is not 4-isopropylphenyl.

2. A compound according to claim 1 further in which $R_1$ is not 2,6-disubstituted phenyl, 2,3,6-trisubstituted phenyl or 2,4,6-trisubstituted phenyl.

3. A compound according to claim 1 in which $R_1$ is

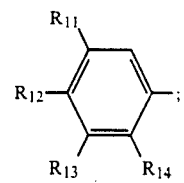

wherein $R_{11}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ carboalkoxy, $C_2$-$C_5$ alkylcarbonyl, nitro or cyano; $R_{12}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_3$-haloalkenoxy; nitro, cyano, $C_1$-$C_4$ alkylsulfonyl, $C_2$-$C_5$ alkylcarbonyl or $C_2$-$C_5$ carboalkoxy; and $R_{13}$ is hydrogen, halogen, $C_1$-$C_4$ haloalkyl or $C_1$-$C_4$ alkoxy, or $R_{11}$ and $R_{12}$ taken together are $C_2$-$C_4$ alkylene, $C_2$-$C_4$ alkyleneoxy, $C_1$-$C_2$ perhaloalkyeneoxy; $C_1$-$C_4$ alkylenedioxy or halo-$C_1$-$C_3$ alkylenedioxy; and $R_{14}$ is hydrogen or fluoro; provided that $R_{11}$, $R_{12}$ and $R_{13}$ are not all hydrogen.

4. A compound according to claim 3 in which $R_{13}$ is hydrogen and $R_{11}$ and $R_{12}$ are other than hydrogen.

5. A compound according to claim 3 in which $R_{11}$ and $R_{13}$ are hydrogen.

6. A compound according to claim 3 in which $R_{12}$ and $R_{13}$ are hydrogen.

7. A compound according to claim 3 in which $R_{12}$ is a $C_1$-$C_2$ polyhaloalkoxy group containing at least one fluorine atom and $R_{13}$ is hydrogen or halogen.

8. A compound according to claim 7 in which $R_{11}$ is halogen, $C_1$-$C_4$ alkyl, $C_1$-$C_4$ haloalkyl, $C_1$-$C_4$ alkoxy or $C_1$-$C_4$ haloalkoxy, $R_{13}$ is hydrogen and $R_{14}$ is hydrogen.

9. A compound according to claim 8 in which $R_2$ is ethyl, isopropyl, isopropenyl, or dichloromethyl.

10. A compound according to claim 3 in which $R_{11}$ is chloro, $R_{12}$ is trifluoromethoxy, $R_{13}$ is hydrogen and $R_{14}$ is hydrogen.

11. A compound according to claim 10 in which $R_2$ is ethyl, isopropyl, isopropenyl, or dichloromethyl.

12. A compound according to claim 3 in which $R_{11}$ is hydrogen or halogen, $R_{12}$ is hydrogen, halogen, $C_1$-$C_4$ alkyl or $C_1$-$C_4$ haloalkoxy; $R_{13}$ is hydrogen and $R_{14}$ is fluoro.

13. A compound according to claim 12 in which $R_{12}$ is fluoro.

14. A compound according to claim 12 in which $R_{11}$ and $R_{12}$ are fluoro.

15. A compound according to claim 12 in which $R_{12}$ is a $C_1$-$C_2$ polyhaloalkoxy group containing at least one fluorine atom and $R_{13}$ is hydrogen.

16. A compound according to claim 12 in which $R_2$ is ethyl, isopropyl, isopropenyl, or dichloromethyl.

17. A compound according to claim 1 in which $R_2$ is ethyl, isopropyl, secondary butyl, dichloromethyl, trifluoromethyl, pentafluoroethyl, 2-fluoro-2-propyl, isopropenyl, cyclopropyl, mono-methyl-substituted cyclopropyl or tetramethyl-substituted cyclopropyl.

18. A compound according to claim 3 in which $R_2$ is isopropyl, isopropenyl, or dichloromethyl.

19. A compound according to claim 18 in which $R_2$ is isopropyl or isopropenyl.

20. A compound according to claim 1 in which $R_3$ is

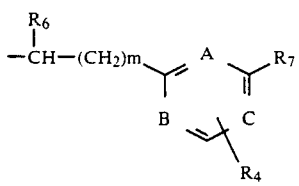

21. A compound according to claim 17 in which $R_3$ is

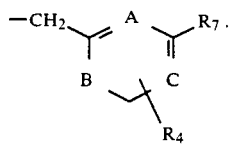

22. A compound according to claim 21 in which $R_3$ is

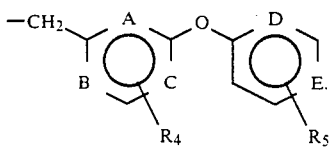

23. A compound according to claim 22 in which $R_3$ is

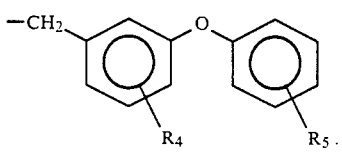

24. A compound according to claim 23 in which $R_4$ is hydrogen.
25. A compound according to claim 23 in which $R_5$ is hydrogen.
26. A compound according to claim 23 in which $R_4$ and $R_5$ are both hydrogen.
27. A compound according to claim 23 in which $R_4$ and $R_5$ are both monohalo.
28. A compound according to claim 27 in which $R_4$ and $R_5$ are both 4-fluoro.
29. A compound according to claim 27 in which $R_4$ is 4-fluoro and $R_5$ is 4-chloro.
30. A compound according to claim 23 in which $R_4$ is 4-fluoro and $R_5$ is difluoro.
31. A compound according to claim 22 in which $R_3$ is

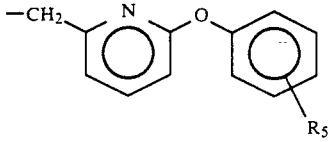

$R_4$ is hydrogen and $R_5$ is hydrogen or 4-halo.

32. A compound according to claim 31 in which $R_5$ is hydrogen.

33. A compound according to claim 31 in which $R_5$ is 4-chloro.
34. A compound according to claim 31 in which $R_5$ is 4-fluoro.
35. A compound according to claim 3 in which $R_3$ is

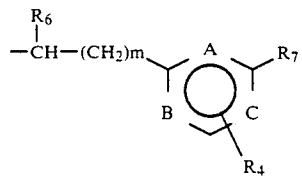

36. A compound according to claim 35 in which $R_3$ is

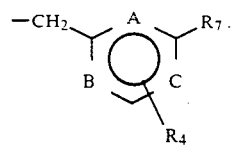

37. A compound according to claim 36 in which $R_3$ is

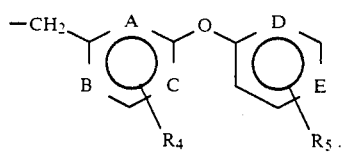

38. A compound according to claim 37 in which $R_3$ is

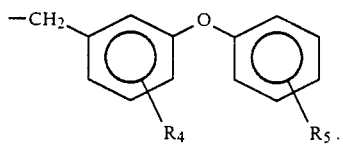

39. A compound according to claim 38 in which $R_4$ is hydrogen.
40. A compound according to claim 38 in which $R_5$ is hydrogen.
41. A compound according to claim 38 in which $R_4$ and $R_5$ are both hydrogen.
42. A compound according to claim 38 in which $R_4$ and $R_5$ are both monohalo.
43. A compound according to claim 42 in which $R_4$ and $R_5$ are both 4-fluoro.
44. A compound according to claim 42 in which $R_4$ is 4-fluoro and $R_5$ is 4-chloro.
45. A compound according to claim 38 in which $R_4$ is 4-fluoro and $R_5$ is difluoro.
46. A compound according to claim 37 in which $R_3$ is

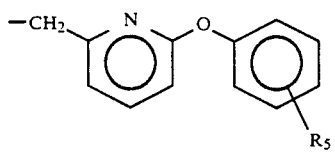

$R_4$ is hydrogen and $R_5$ is hydrogen or 4-halo.

47. A compound according to claim 38 in which $R_4$, $R_5$ and $R_{13}$ are all hydrogen.

48. A compound according to claim 38 in which $R_4$, $R_5$, $R_{12}$ and $R_{13}$ are all hydrogen.

49. A compound according to claim 38 in which $R_4$ is 4-halo and $R_5$ and $R_{13}$ are both hydrogen.

50. A compound according to claim 49 in which $R_4$ is 4-fluoro.

51. A compound according to claim 38 in which $R_5$ is 4-halo and $R_4$ and $R_{13}$ are both hydrogen.

52. A compound according to claim 51 in which $R_5$ is 4-fluoro.

53. A compound according to claim 51 in which $R_5$ is 4-chloro.

54. A compound according to claim 38 in which $R_4$ and $R_5$ are both 4-halo and $R_{13}$ is hydrogen.

55. A compound according to claim 54 in which $R_4$ and $R_5$ are both 4-fluoro.

56. A compound according to claim 54 in which $R_4$ is 4-fluoro and $R_5$ is 4-chloro.

57. A compound according to claim 38 in which $R_{11}$ is chloro, $R_{12}$ is fluoro, and $R_{13}$ is hydrogen.

58. A compound according to claim 37 in which $R_3$ is

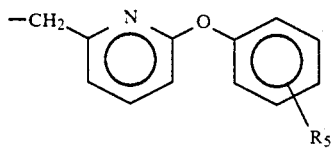

$R_4$ is hydrogen and $R_5$ is hydrogen or 4-halo.

59. A compound according to claim 58 in which $R_5$ is hydrogen.

60. A compound according to claim 58 in which $R_5$ is 4-chloro.

61. A compound according to claim 58 in which $R_5$ is 4-fluoro.

62. A compound according to claim 58 in which $R_{11}$ is chloro, $R_{12}$ is fluoro and $R_{13}$ is hydrogen.

63. A compound according to claim 19 in which $R_3$ is

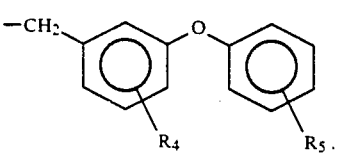

64. A compound according to claim 19 in which $R_3$ is

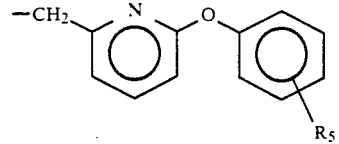

65. A compound according to claim 1 in which $R_3$ is

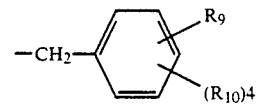

and $R_9$ is 4-propargyl.

66. A compound according to claim 65 in which $R_1$ is 3- or 4-trifluoromethylphenyl.

67. A compound according to claim 1 in which $R_1$ is 3-chlorophenyl, $R_2$ is dichloromethyl and $R_3$ is 3-phenoxybenzyl.

68. A compound according to claim 1 in which $R_1$ is 4-chlorophenyl, $R_2$ is isopropyl and $R_3$ is 3-phenoxybenzyl.

69. A compound according to claim 1 in which $R_1$ is 3-chlorophenyl, $R_2$ is isopropyl and $R_3$ is 3-phenoxybenzyl.

70. A compound according to claim 1 in which $R_1$ is 3,4-dichlorophenyl, $R_2$ is isopropyl and $R_3$ is 3-phenoxybenzyl.

71. A compound according to claim 1 in which $R_1$ is 4-chlorophenyl, $R_2$ is isopropyl and $R_3$ is 3-phenoxy,4-fluorobenzyl.

72. A compound according to claim 1 in which $R_1$ is 3,4-dichlorophenyl, $R_2$ is isopropyl and $R_3$ is 3-(4-fluorophenoxy)benzyl.

73. A compound according to claim 1 in which $R_1$ is pentafluorophenyl, $R_2$ is isopropyl and $R_3$ is 3-phenoxybenzyl.

74. A compound according to claim 1 in which $R_1$ is 3,4-difluorophenyl, $R_2$ is isopropyl and $R_3$ is 3-phenoxybenzyl.

75. A compound according to claim 1 in which $R_1$ is 3-trifluoromethylphenyl, $R_2$ is isopropyl and $R_3$ is 3-phenoxybenzyl.

76. A compound according to claim 1 in which $R_1$ is 3-trifluoromethyl,4-fluorophenyl, $R_2$ is isopropyl and $R_3$ is 3-phenoxybenzyl.

77. A compound according to claim 1 in which $R_1$ is 3-trifluoromethylphenyl, $R_2$ is isopropyl and $R_3$ is 3-phenoxy,4-fluorobenzyl.

78. A compound according to claim 1 in which $R_1$ is 3-chloro,4-fluorophenyl, $R_2$ is isopropyl and $R_3$ is 3-phenoxybenzyl.

79. A compound according to claim 1 in which $R_1$ is 3-chloro,4-fluorophenyl, $R_2$ is isopropyl and $R_3$ is 3-phenoxy,4-fluorobenzyl.

80. A compound according to claim 1 in which $R_1$ is 3-chloro,4-fluorophenyl, $R_2$ is isopropyl and $R_3$ is 3-(4-fluorophenoxy)benzyl.

81. A compound according to claim 1 in which $R_1$ is 3-chloro,4-fluorophenyl, $R_2$ is ethyl and $R_3$ is 3-(4-fluorophenoxy)benzyl.

82. A compound according to claim 1 in which $R_1$ is 3-chloro,4-fluorophenyl, $R_2$ is isopropyl and $R_3$ is 6-(4-fluorophenoxy)-pyrid-2-ylmethyl.

83. A compound according to claim 1 in which $R_1$ is 3-chloro,4-fluorophenyl, $R_2$ is isopropyl and $R_3$ is 6-(4-chlorophenoxy)-pyrid-2-ylmethyl.

84. A compound according to claim 1 in which $R_1$ is 3-chloro,4-fluorophenyl, $R_2$ is secondary butyl and $R_3$ is 3-phenoxybenzyl.

85. A compound according to claim 1 in which $R_1$ is 4-isopropylphenyl, $R_2$ is isopropyl and $R_3$ is 3-phenoxybenzyl.

86. A compound according to claim 1 in which $R_1$ is 4-(tertiary butyl)phenyl, $R_2$ is isopropyl and $R_3$ is 3-phenoxybenzyl.

87. A compound according to claim 1 in which $R_1$ is 4-ethylphenyl, $R_2$ is tertiary butyl and $R_3$ is 3-phenoxybenzyl.

88. A compound according to claim 1 in which $R_1$ is 3,4-methylenedioxyphenyl, $R_2$ is isopropyl and $R_3$ is 3-phenoxybenzyl.

89. A compound according to claim 1 in which $R_1$ is 3,4-methylenedioxyphenyl, $R_2$ is secondary butyl and $R_3$ is 3-phenoxybenzyl.

90. A compound according to claim 1 in which $R_1$ is 4-chlorophenyl, $R_2$ is isopropyl and $R_3$ is 3-(4-fluorophenoxy)benzyl.

91. A compound according to claim 1 in which $R_1$ is 3-chlorophenyl, $R_2$ is isopropyl and $R_3$ is 3-(4-fluorophenoxy)benzyl.

92. A compound according to claim 1 in which $R_1$ is 3-trifluoromethylphenyl, $R_2$ is isopropyl and $R_3$ is 3-(4-fluorophenoxy)benzyl.

93. A compound according to claim 1 in which $R_1$ is 3-chloro,4-fluorophenyl, $R_2$ is isopropyl and $R_3$ is 3-(4-fluorophenoxy),4-fluorobenzyl.

94. A compound according to claim 1 in which $R_1$ is 3-chloro,4-fluorophenyl, $R_2$ is isopropyl and $R_3$ is 3-(3,4-difluorophenoxy)benzyl.

95. A compound according to claim 1 in which $R_1$ is 3-chloro,4-fluorophenyl, $R_2$ is isopropyl and $R_3$ is 3-(4-bromophenoxy)benzyl.

96. A compound according to claim 1 in which $R_1$ is 3-chloro,4-fluorophenyl, $R_2$ is isopropyl and $R_3$ is 3-(4-chlorophenoxy)benzyl.

97. A compound according to claim 1 in which $R_1$ is 5-(2,2-dimethyl-1,3-benzodioxolyl), $R_2$ is isopropyl and $R_3$ is 3-phenoxy,4-fluorobenzyl.

98. A compound according to claim 1 in which $R_1$ is 3,4-(difluoromethylenedioxy)phenyl, $R_2$ is isopropyl and $R_3$ is 3-(4-fluorophenoxy)benzyl.

99. A compound according to claim 1 in which $R_1$ is 3-iodophenyl, $R_2$ is isopropyl and $R_3$ is 3-(4-fluorophenoxy)benzyl.

100. A compound according to claim 1 in which $R_1$ is 3-chloro-4-trifluoromethoxyphenyl, $R_2$ is isopropyl and $R_3$ is 3-(4-fluorophenoxy),4-fluorobenzyl.

101. A compound according to claim 1 in which $R_1$ is 3-trifluoromethylphenyl, $R_2$ is isopropyl and $R_3$ is 2,3,5,6-tetrafluoro-4-propargylbenzyl.

102. A compound according to claim 1 in which $R_1$ is 4-trifluoromethylphenyl, $R_2$ is isopropyl, and $R_3$ is 2,3,5,6-tetrafluoro-4-propargylbenzyl.

103. A method for controlling insects comprising applying to an insect, the locus of an insect or a locus at which insecticidal control is desired, an insecticidally effective amount of a compound according to claim 1.

104. A method for controlling insects according to claim 103 in which the insect is a member of the order Lepidoptera.

105. A method for controlling insects according to claim 103 in which the insect is a member of the other Coleoptera.

106. A method for controlling insects according to claim 103 in which the insect is a member of the order Hemiptera.

107. A method for controlling insects comprising applying to an insect, the locus of an insect, or a locus at which insecticidal control is desired, an insecticidally effective amount of a compound according to claim 3.

108. A method for controlling insects comprising applying to an insect, the locus of an insect or a locus at which insecticidal control is desired, an insecticidally effective amount of a compound according to claim 8.

109. A method for controlling insects comprising applying to an insect, the locus of an insect or a locus at which insecticidal control is desired, an insecticidally effective amount of a compound according to claim 23.

110. A method for controlling insects comprising applying to an insect, the locus of an insect or a locus at which insecticidal control is desired, an insecticidally effective amount of a compound according to claim 38.

111. An insecticidal composition comprising:
(a) an insecticidally effective amount of a compound according to claim 1; and
(b) an insecticidally suitable diluent or carrier.

112. A compound according to claim 1 in which $R_1$ is

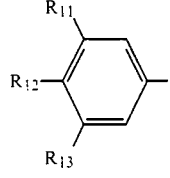

wherein $R_{11}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ carboalkoxy, $C_2$-$C_5$ alkylcarbonyl, nitro or cyano; $R_{12}$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, nitro, cyano, $C_1$-$C_4$ alkylsulfonyl, $C_2$-$C_5$ alkylcarbonyl or $C_2$-$C_5$ carboalkoxy; and $R_{13}$ is hydrogen, halogen, $C_1$-$C_4$ haloalkyl or $C_1$-$C_4$ alkoxy, or $R_{11}$ and $R_{12}$ taken together are $C_2$-$C_4$ alkylene, $C_2$-$C_4$ alkyleneoxy, $C_1$-$C_4$ alkylenedioxy or halo-$C_1$-$C_3$ alkylenedioxy.

113. A compound according to claim 112 in which $R_{13}$ is hydrogen and $R_{11}$ and $R_{12}$ are other than hydrogen.

114. A compound according to claim 112 in which $R_{11}$ and $R_{13}$ are hydrogen.

115. A compound according to claim 112 in which $R_{12}$ and $R_{13}$ are hydrogen.

116. A compound according to claim 112 in which $R_{12}$ is a $C_1$-$C_2$ polyhaloalkoxy group containing at least one fluorine atom and $R_{13}$ is hydrogen or halogen.

117. A compound according to claim 116 in which $R_{11}$ is halogen, $C_1$-$C_4$ alkyl, $C_1$-$C_4$ haloalkyl, $C_1$-$C_4$ alkoxy or $C_1$-$C_4$ haloalkoxy; and $R_{13}$ is hydrogen.

118. A compound according to claim 112 in which $R_{11}$ and $R_{12}$ are both halogen, and $R_{13}$ is hydrogen.

119. A compound according to claim 117 in which $R_2$ is ethyl, isopropyl, isopropenyl or dichloromethyl.

120. A compound according to claim 112 in which $R_{11}$ is halogen; $R_{12}$ is trifluoromethoxy; and $R_{13}$ is hydrogen.

121. A compound according to claim 112 in which R₃ is

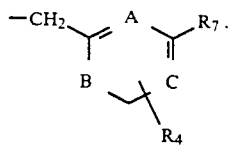

122. A compound according to claim 121 in which R₃ is

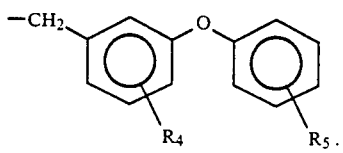

123. A compound according to claim 122 in which R₄ is hydrogen.
124. A compound according to claim 122 in which R₅ is hydrogen.
125. A compound according to claim 122 in which R₄ and R₅ are both hydrogen.
126. A compound according to claim 122 in which R₄ and R₅ are both mono-halo.
127. A compound according to claim 122 in which R₄ and R₅ are both 4-fluoro.
128. A compound according to claim 122 in which R₄ is 4-fluoro and R₅ is 4-chloro.

129. A compound according to claim 121 in which R₃ is

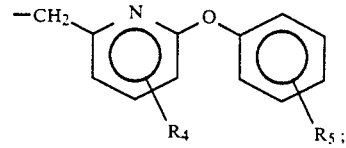

R₄ is hydrogen; and R₅ is hydrogen or 4-halo.

130. A compound according to claim 1 in which R₁ is 3-fluoro-4-trifluoromethoxyphenyl; R₂ is isopropyl; and R₃ is 3-(4-fluorophenoxy),4-fluorobenzyl.

131. A method for controlling insects comprising applying to an insect, the locus of an insect, or a locus in which insecticidal control is desired, an insecticidally effective amount of a compound according to claim 112.

132. A method for controlling insects comprising applying to an insect, the locus of an insect, or a locus in which insecticidal control is desired, an insecticidally effective amount of a compound according to claim 121.

133. An insecticidal composition comprising: (a) an insecticidally effective amount of a compound according to claim 112; and (b) an insecticidally suitable diluent or powder.

134. A compound according to claim 1 in which R₁ is 3,4-dichlorophenyl; R₂ is isopropyl; and R₃ is 3-(4-fluorophenoxy)-4-fluorobenzyl.

* * * * *